(12) United States Patent
Oh et al.

(10) Patent No.: US 12,284,910 B2
(45) Date of Patent: Apr. 22, 2025

(54) ORGANIC ELECTROLUMINESCENT COMPOUND AND ORGANIC ELECTROLUMINESCENT DEVICE COMPRISING THE SAME

(71) Applicant: ROHM AND HAAS ELECTRONIC MATERIALS KOREA LTD., Chungcheongnam-do (KR)

(72) Inventors: Hong-Se Oh, Gyeonggi-do (KR); Ga-Won Lee, Gyeonggi-do (KR); Tae-Jin Lee, Gyeonggi-do (KR)

(73) Assignee: Rohm and Haas Electronic Materials Korea Ltd. (KR)

( * ) Notice: Subject to any disclaimer, the term of this patent is extended or adjusted under 35 U.S.C. 154(b) by 938 days.

(21) Appl. No.: 17/274,761

(22) PCT Filed: Sep. 10, 2019

(86) PCT No.: PCT/KR2019/011745
§ 371 (c)(1),
(2) Date: Mar. 9, 2021

(87) PCT Pub. No.: WO2020/055113
PCT Pub. Date: Mar. 19, 2020

(65) Prior Publication Data
US 2022/0052272 A1    Feb. 17, 2022

(30) Foreign Application Priority Data
Sep. 11, 2018   (KR) .................. 10-2018-0108504
Sep. 5, 2019    (KR) .................. 10-2019-0110256

(51) Int. Cl.
*H10K 85/60*     (2023.01)
*C07D 225/04*    (2006.01)
*C07D 313/20*    (2006.01)
*H10K 50/15*     (2023.01)

(52) U.S. Cl.
CPC ....... *H10K 85/6572* (2023.02); *C07D 225/04* (2013.01); *C07D 313/20* (2013.01); *H10K 85/622* (2023.02); *H10K 85/626* (2023.02); *H10K 85/6574* (2023.02); *H10K 50/15* (2023.02)

(58) Field of Classification Search
CPC ............ H10K 85/6572; H10K 85/622; H10K 85/626; H10K 85/6574; H10K 50/15; C07D 225/04; C07D 313/20; C07D 337/16; C07D 403/04; C07D 403/10; C07D 405/04; C07D 405/10; C07D 409/04; C07D 409/10; C07D 471/06; C07D 491/06; C07D 495/06
USPC ....................................................... 540/476
See application file for complete search history.

(56) References Cited

U.S. PATENT DOCUMENTS

2016/0163998 A1   6/2016   Saito et al.
2020/0235307 A1   7/2020   Cho et al.

FOREIGN PATENT DOCUMENTS

KR    20150121337 A    10/2015

OTHER PUBLICATIONS

Catalytic Double Carbon-Boron Bond 66-2 Formation for the Synthesis of Cyclic Diarylborinic Acids as Versatile Building Blocks for π-Extended Heteroarenes, Angewandte Chemie International Edition (2017), 56(8), 2069-2073.
Pieters, G. et al., "New Chiral Cyclooctatriene-Based Polycyclic Architectures", Org. Lett., 2011, vol. 13, No. 16, pp. 4450-4453 scheme 1.
Li, X. et al., "Palladium-Catalyzed Double Suzuki Reactions: Synthesis of Dibenzo[4,5:6,7]cyclohepta[1,2,3-de] naphthalenes", Asian J. Org. Chem., 2017, vol. 6, pp. 1876-1884.

*Primary Examiner* — Taylor V Oh
(74) *Attorney, Agent, or Firm* — G. Creston Campbell

(57) ABSTRACT

The present disclosure relates to an organic electroluminescent compound represented by formula 1 and an organic electroluminescent device comprising the same. By comprising the organic electroluminescent compound of the present disclosure, an organic electroluminescent device having improved driving voltage and/or luminous efficiency characteristics can be provided.

9 Claims, No Drawings

ORGANIC ELECTROLUMINESCENT COMPOUND AND ORGANIC ELECTROLUMINESCENT DEVICE COMPRISING THE SAME

TECHNICAL FIELD

The present disclosure relates to an organic electroluminescent compound and an organic electroluminescent device comprising the same.

BACKGROUND ART

An electroluminescent device (EL device) is a self-light-emitting device which has advantages in that it provides a wider viewing angle, a greater contrast ratio, and a faster response time. The first organic EL device was developed by Eastman Kodak in 1987, by using small aromatic diamine molecules, and aluminum complexes as materials for forming a light-emitting layer [Appl. Phys. Lett. 51, 913, 1987].

In order to enhance the efficiency and stability of an organic EL device, it has a structure of a multilayer comprising a hole injection layer, a hole transport layer, a light-emitting layer, an electron transport layer, and an electron injection layer. The selection of a compound comprised in the hole transport layer, etc., is known as one of the methods for improving the characteristics of a device such as hole transport efficiency to the light-emitting layer, luminous efficiency, lifespan, etc.

In this regard, copper phthalocyanine (CuPc), 4,4'-bis[N-(1-naphthyl)-N-phenylamino]biphenyl (NPB), N,N'-diphenyl-N,N'-bis(3-methylphenyl)-(1,1'-biphenyl)-4,4'-diamine (TPD), 4,4',4"-tris(3-methylphenylphenylamino)triphenylamine (MTDATA), etc., were used as a hole injection and transport material in an organic EL device. However, an organic EL device using these materials is problematic in quantum efficiency and lifespan. It is because, when an organic EL device is driven under high current, thermal stress occurs between an anode and the hole injection layer. Thermal stress significantly reduces the lifespan of the device. Further, since the organic material used in the hole injection layer has very high hole mobility, the hole-electron charge balance may be broken and quantum yield (cd/A) may decrease.

Therefore, a hole transport material for improving performance of an organic EL device still needs to be developed.

Catalytic Double Carbon-Boron Bond Formation for the Synthesis of Cyclic Diarylborinic Acids as Versatile Building Blocks for π-Extended Heteroarenes, Angewandte Chemie International Edition (2017), 56(8), 2069-2073 discloses a compound of a fused 8-membered ring structure comprising an oxygen atom. However, said reference does not disclose any example using such compound in a hole transport zone of an OLED.

DISCLOSURE OF INVENTION

Technical Problem

The objective of the present disclosure is first to provide an organic electroluminescent compound which is efficient for producing an organic electroluminescent device having improved driving voltage and/or luminous efficiency characteristics, and second to provide an organic electroluminescent device comprising the organic electroluminescent compound.

Solution to Problem

Generally, a thin film which consists of a material having low glass transition temperature may be easily changed due to the heat generated when driving the device, and the performance of the OLED may be deteriorated due to the decrease of the charge mobility within the thin film. Accordingly, a material having high glass transition temperature may be advantageous in an OLED device. Among various methods for increasing the glass transition temperature, a comparatively easy way to do it is to increase the molecular weight by bonding substituents. However, according to this method, there is a limit since the deposition temperature of the organic compound increases. As a result of intense studies, the present inventors found that by having a distorted structure, the organic electroluminescent compound of the present disclosure may provide an excellent thermal stability by having higher glass transition temperature (Tg) (130° C. or higher) compared to other compounds having the same molecular weight, thereby contributing to solving the problem of the present disclosure. Specifically, the present inventors found that the above objective can be achieved by an organic electroluminescent compound represented by the following formula 1:

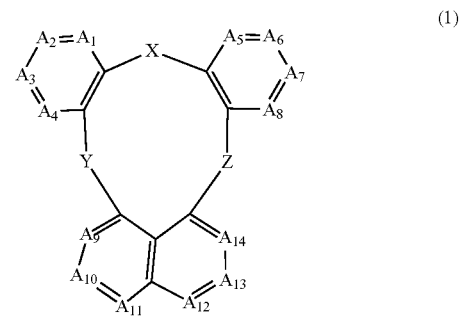

(1)

wherein

X, Y, and Z each independently represent a single bond, O, S, $NR_1$, or $CR_2R_3$, with a proviso that not all of X, Y, and Z are a single bond;

$R_1$ to $R_3$ each independently represent hydrogen, deuterium, a halogen, a substituted or unsubstituted (C1-C30)alkyl, a substituted or unsubstituted (C6-C30)aryl, a substituted or unsubstituted (3- to 30-membered) heteroaryl, a substituted or unsubstituted (C3-C30) cycloalkyl, a substituted or unsubstituted (C1-C30) alkoxy, a substituted or unsubstituted tri(C1-C30) alkylsilyl, a substituted or unsubstituted di(C1-C30) alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl (C6-C30)arylamino; or $R_2$ and $R_3$ may be linked to each other to form a ring(s), where if a plurality of $R_1$ to $R_3$ is present, each of $R_1$, each of $R_2$, and each of $R_3$ may be the same or different;

$A_1$ to $A_{14}$ each independently represent $CR_4$ or N; and $R_4$ each independently represents hydrogen, deuterium, a halogen, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C8-C30)arylamino, or a substituted or unsubstituted (C1-C30)alkyl(C6-C30)arylamino; or two or more adjacent $R_4$'s may be linked to each other to form a ring(s).

Advantageous Effects of Invention

By using the organic electroluminescent compound of the present disclosure, an organic electroluminescent device having improved driving voltage and/or luminous efficiency characteristics can be provided.

MODE FOR THE INVENTION

Hereinafter, the present disclosure will be described in detail. However, the following description is intended to explain the disclosure, and is not meant in any way to restrict the scope of the disclosure.

The term "organic electroluminescent compound" in the present disclosure means a compound that may be used in an organic electroluminescent device, and may be comprised in any layer constituting an organic electroluminescent device, as necessary.

The term "organic electroluminescent material" in the present disclosure means a material that may be used in an organic electroluminescent device, and may comprise at least one compound. The organic electroluminescent material may be comprised in any layer constituting an organic electroluminescent device, as necessary. For example, the organic electroluminescent material may be a hole injection material, a hole transport material, a hole auxiliary material, a light-emitting auxiliary material, an electron blocking material, a light-emitting material, an electron buffer material, a hole blocking material, an electron transport material, or an electron injection material.

The organic electroluminescent material of the present disclosure may comprise at least one compound represented by formula 1. The compound represented by formula 1 may be comprised in at least one layer constituting an organic electroluminescent device, and may be comprised in at least one layer constituting a hole transport zone, but is not limited thereto. When the compound of formula 1 is comprised in a hole transport layer, a hole auxiliary layer, or a light-emitting auxiliary layer, it may be comprised as a hole transport material, a hole auxiliary material, or a light-emitting auxiliary material. In addition, the compound represented by formula 1 may be comprised in a light-emitting layer, but is not limited thereto. When the compound of formula 1 is comprised in a light-emitting layer, it may be comprised as a host.

Herein, "(C1-C30)alkyl" is meant to be a linear or branched alkyl having 1 to 30 carbon atoms constituting the chain, in which the number of carbon atoms is preferably 1 to 20, more preferably 1 to 10, and includes methyl, ethyl, n-propyl, isopropyl, n-butyl, isobutyl, tert-butyl, etc. "(C2-C30)alkenyl" is meant to be a linear or branched alkenyl having 2 to 30 carbon atoms constituting the chain, in which the number of carbon atoms is preferably 2 to 20, more preferably 2 to 10, and includes vinyl, 1-propenyl, 2-propenyl, 1-butenyl, 2-butenyl, 3-butenyl, 2-methylbut-2-enyl, etc. "(C2-C30)alkynyl" is meant to be a linear or branched alkynyl having 2 to 30 carbon atoms constituting the chain, in which the number of carbon atoms is preferably 2 to 20, more preferably 2 to 10, and includes ethynyl, 1-propynyl, 2-propynyl, 1-butynyl, 2-butynyl, 3-butynyl, 1-methylpent-2-ynyl, etc. "(C3-C30)cycloalkyl" is meant to be a mono- or polycyclic hydrocarbon having 3 to 30 ring backbone carbon atoms, in which the number of carbon atoms is preferably 3 to 20, more preferably 3 to 7, and includes cyclopropyl, cyclobutyl, cyclopentyl, cyclohexyl, etc. "(3- to 7-membered)heterocycloalkyl" is meant to be a cycloalkyl having at least one heteroatom selected from the group consisting of B, N, O, S, Si, and P, preferably selected from the group consisting of O, S, and N, and 3 to 7 ring backbone atoms, preferably 5 to 7 ring backbone atoms, and includes tetrahydrofuran, pyrrolidine, thiolan, tetrahydropyran, etc. "(C6-C30)aryl" is meant to be a monocyclic or fused ring radical derived from an aromatic hydrocarbon having 6 to 30 ring backbone carbon atoms and may be partially saturated, in which the number of ring backbone carbon atoms is preferably 6 to 25, more preferably 6 to 18, includes a spiro structure, and includes phenyl, biphenyl, terphenyl, naphthyl, binaphthyl, phenylnaphthyl, naphthylphenyl, phenylterphenyl, fluorenyl, phenylfluorenyl, benzofluorenyl, dibenzofluorenyl, phenanthrenyl, phenylphenanthrenyl, anthracenyl, indenyl, triphenylenyl, pyrenyl, tetracenyl, perylenyl, chrysenyl, naphthacenyl, fluoranthenyl, spirobifluorenyl, spiro[fluorene-benzofluoren]yl, etc. More specifically, the above aryl may include a phenyl group, a 1-naphthyl group, a 2-naphthyl group, a 1-anthryl group, a 2-anthryl group, a 9-anthryl group, a benzanthryl group, a 1-phenanthryl group, a 2-phenanthryl group, a 3-phenanthryl group, a 4-phenanthryl group, a 9-phenanthryl group, a naphthacenyl group, a pyrenyl group, a 1-chrysenyl group, a 2-chrysenyl group, a 3-chrysenyl group, a 4-chrysenyl group, a 5-chrysenyl group, a 6-chrysenyl group, a benzo[c]phenanthryl group, a benzo[g]chrysenyl group, a 1-triphenylenyl group, a 2-triphenylenyl group, a 3-triphenylenyl group, a 4-triphenylenyl group, a 1-fluorenyl group, a 2-fluorenyl group, a 3-fluorenyl group, a 4-fluorenyl group, a 9-fluorenyl group, a benzofluorenyl group, a dibenzofluorenyl group, a 2-biphenylyl group, a 3-biphenylyl group, a 4-biphenylyl group, an o-terphenyl group, an m-terphenyl-4-yl group, an m-terphenyl-3-yl group, an m-terphenyl-2-yl group, a p-terphenyl-4-yl group, a p-terphenyl-3-yl group, a p-terphenyl-2-yl group, an m-quaterphenyl group, a 3-fluoranthenyl group, a 4-fluoranthenyl group, an 8-fluoranthenyl group, a 9-fluoranthenyl group, a benzofluoranthenyl group, an o-tolyl group, an m-tolyl group, a p-tolyl group, a 2,3-xylyl group, a 3,4-xylyl group, a 2,5-xylyl group, a mesityl group, an o-cumenyl group, an m-cumenyl group, a p-cumenyl group, a p-t-butylphenyl group, a p-(2-phenylpropyl)phenyl group, a 4'-methylbiphenylyl group, a 4"-t-butyl-p-terphenyl-4-yl group, a 9,9-dimethyl-1-fluorenyl group, a 9,9-dimethyl-2-fluorenyl group, a 9,9-dimethyl-3-fluorenyl group, a 9,9-dimethyl-4-fluorenyl group, a 9,9-diphenyl-1-fluorenyl group, a 9,9-diphenyl-2-fluorenyl group, a 9,9-diphenyl-3-fluorenyl group, and a 9,9-diphenyl-4-fluorenyl group. "(3- to 30-membered)heteroaryl" is meant to be an aryl group having at least one, preferably 1 to 4 heteroatoms selected from the group consisting of B, N, O, S, Si, and P, and 3 to 30 ring backbone atoms; is a monocyclic ring, or a fused ring condensed with at least one benzene ring; may be partially saturated; may be one formed by linking at least one heteroaryl or aryl group to a heteroaryl group via a single bond(s); includes a spiro structure; and includes a monocyclic ring-type heteroaryl including furyl, thiophenyl, pyrrolyl, imidazolyl, pyrazolyl, thiazolyl, thiadiazolyl, isothiazolyl, isoxazolyl, oxazolyl, oxadiazolyl, triazinyl, tetrazinyl, triazolyl, tetrazolyl, furazanyl, pyridyl, pyrazinyl, pyrimidinyl, pyridazinyl, etc., and a fused ring-type heteroaryl including benzofuranyl, benzothiophenyl, isobenzofuranyl, dibenzofuranyl, dibenzothiophenyl, benzimidazolyl, benzothiazolyl, benzoisothiazolyl, benzoisoxazolyl, benzoxazolyl, isoindolyl, indolyl, benzoindolyl, indazolyl, benzothiadiazolyl, quinolyl, isoquinolyl, cinnolinyl, quinazolinyl, benzoquinazolinyl, quinoxalinyl, benzoquinoxalinyl, naphthyridinyl, carbazolyl, benzocarbazolyl, dibenzocarbazolyl, phenoxazinyl, phenothiazinyl, phenanthridinyl, benzodioxolyl, dihydroacridinyl, etc. More specifically, the above hereroaryl may include a 1-pyrrolyl group, a 2-pyrrolyl group, a 3-pyrrolyl group, a pyrazinyl group, a 2-pyridinyl group, a 2-pyrimidinyl group, a 4-pyrimidinyl group, a 5-pyrimidinyl group, a 6-pyrimidinyl group, a 1,2,3-triazin-4-yl group, a 1,2,4-triazin-3-yl group, a 1,3,5-triazin-2-yl group, a 1-imidazolyl group, a 2-imidazolyl group, a 1-pyrazolyl group, a 1-indolidinyl group, a 2-indolidinyl group, a 3-indolidinyl group, a 5-indolidinyl group, a 6-indolidinyl group, a 7-indolidinyl group, an 8-indolidinyl group, a 2-imidazopyridinyl group, a 3-imidazopyridinyl group, a 5-imidazopyridinyl group, a 6-imidazopyridinyl group, a 7-imidazopyridinyl group, an 8-imidazopyridinyl group, a 3-pyridinyl group, a 4-pyridinyl group, a 1-indolyl group, a 2-indolyl group, a 3-indolyl group, a 4-indolyl group, a 5-indolyl group, a 6-indolyl group, a 7-indolyl group, a 1-isoindolyl group, a 2-isoindolyl group, a 3-isoindolyl group, a 4-isoindolyl group, a 5-isoindolyl group, a 6-isoindolyl group, a 7-isoindolyl group, a 2-furyl group, a 3-furyl group, a 2-benzofuranyl group, a 3-benzofuranyl group, a 4-benzofuranyl group, a 5-benzofuranyl group, a 6-benzofuranyl group, a 7-benzofuranyl group, a 1-isobenzofuranyl group, a 3-isobenzofuranyl group, a 4-isobenzofuranyl group, a 5-isobenzofuranyl group, a 6-isobenzofuranyl group, a 7-isobenzofuranyl group, a 2-quinolyl group, a 3-quinolyl group, a 4-quinolyl group, a 5-quinolyl group, a 6-quinolyl group, a 7-quinolyl group, an 8-quinolyl group, a 1-isoquinolyl group, a 3-isoquinolyl group, a 4-isoquinolyl group, a 5-isoquinolyl group, a 6-isoquinolyl group, a 7-isoquinolyl group, an 8-isoquinolyl group, a 2-quinoxalinyl group, a 3-quinoxalinyl group, a 6-quinoxalinyl group, a 1-carbazolyl group, a 2-carbazolyl group, a 3-carbazolyl group, a 4-carbazolyl group, a 9-carbazolyl group, an azacarbazolyl-1-yl group, an azacarbazolyl-2-yl group, an azacarbazolyl-3-yl group, an azacarbazolyl-4-yl group, an azacarbazolyl-5-yl group, an azacarbazolyl-6-yl group, an azacarbazolyl-7-yl group, an azacarbazolyl-8-yl group, an azacarbazolyl-9-yl group, a 1-phenanthridinyl group, a 2-phenanthridinyl group, a 3-phenanthridinyl group, a 4-phenanthridinyl group, a 6-phenanthridinyl group, a 7-phenanthridinyl group, an 8-phenanthridinyl group, a 9-phenanthridinyl group, a 10-phenanthridinyl group, a 1-acridinyl group, a 2-acridinyl group, a 3-acridinyl group, a 4-acridinyl group, a 9-acridinyl group, a 2-oxazolyl group, a 4-oxazolyl group, a 5-oxazolyl group, a 2-oxadiazolyl group, a 5-oxadiazolyl group, a 3-furazanyl group, a 2-thienyl group, a 3-thienyl group, a 2-methylpyrrol-1-yl group, a 2-methylpyrrol-3-yl group, a 2-methylpyrrol-4-yl group, a 2-methylpyrrol-5-yl group, a 3-methylpyrrol-1-yl group, a 3-methylpyrrol-2-yl group, a 3-methylpyrrol-4-yl group, a 3-methylpyrrol-5-yl group, a 2-t-butylpyrrol-4-yl group, a 3-(2-phenylpropyl)pyrrol-1-yl group, a 2-methyl-1-indolyl group, a 4-methyl-1-indolyl group, a 2-methyl-3-indolyl group, a 4-methyl-3-indolyl group, a 2-t-butyl-1-indolyl group, a 4-t-butyl-1-indolyl group, a 2-t-butyl-3-indolyl group, a 4-t-butyl-3-indolyl group, a 1-dibenzofuranyl group, a 2-dibenzofuranyl group, a 3-dibenzofuranyl group, a 4-dibenzofuranyl group, a 1-dibenzothiophenyl group, a 2-dibenzothiophenyl group, a 3-dibenzothiophenyl group, a 4-dibenzothiophenyl group, a 1-silafluorenyl group, a 2-silafluorenyl group, a 3-silafluorenyl group, a 4-silafluorenyl group, a 1-germafluorenyl group, a 2-germafluorenyl group, a 3-germafluorenyl group, and a 4-germafluorenyl group. "Halogen" includes F, Cl, Br, and I.

In addition, "ortho," "meta," and "para" signify substitution positions of two substituents. The ortho position represents a just neighboring position, and, for example, in the case of benzene, represents 1,2 positions. The meta position represents the position next to the just neighboring position, and, for example, in the case of benzene, represents 1,3 positions. The para position represents the position next to the meta position, and, for example, in the case of benzene, represents 1,4 positions.

Herein, "substituted" in the expression "substituted or unsubstituted" means that a hydrogen atom in a certain functional group is replaced with another atom or functional group, i.e., a substituent. The substituents of the substituted alkyl, the substituted aryl, the substituted heteroaryl, the substituted cycloalkyl, the substituted alkoxy, the substituted trialkylsilyl, the substituted dialkylarylsilyl, the substituted alkyldiarylsilyl, the substituted triarylsilyl, the substituted mono- or di-alkylamino, the substituted mono- or di-arylamino, and the substituted alkylarylamino in $R_1$ to $R_4$ in formula 1 each independently are at least one selected from the group consisting of deuterium; a halogen; a cyano; a carboxyl; a nitro; a hydroxyl; a (C1-C30)alkyl; a halo(C1-C30)alkyl; a (C2-C30)alkenyl; a (C2-C30)alkynyl; a (C1-C30)alkoxy; a (C1-C30)alkylthio; a (C3-C30)cycloalkyl; a (C3-C30)cycloalkenyl; a (3- to 7-membered)heterocycloalkyl; a (C6-C30)aryloxy; a (C6-C30)arylthio; a (3- to 30-membered)heteroaryl unsubstituted or substituted with a (C6-C30)aryl(s); a (C8-C30)aryl unsubstituted or substituted with one or more of a (C1-C30)alkyl(s) and a (3- to 30-membered)heteroaryl(s); a tri(C1-C30)alkylsilyl; a tri(C6-C30)arylsilyl; a di(C1-C30)alkyl(C6-C30)arylsilyl; a (C1-C30)alkyldi(C6-C30)arylsilyl; an amino; a mono- or di-(C1-C30)alkylamino; a mono- or di-(C6-C30)arylamino unsubstituted or substituted with a (C1-C30)alkyl(s); a (C1-C30)alkyl(C6-C30)arylamino; a (C1-C30)alkylcarbonyl; a (C1-C30)alkoxycarbonyl; a (C6-C30)arylcarbonyl; a di(C6-C30)arylboronyl; a di(C1-C30)alkylboronyl; a (C1-C30)alkyl(C6-C30)arylboronyl; a (C6-C30)aryl(C1-C30)alkyl; and a (C1-C30)alkyl(C6-C30)aryl, and preferably each independently are at least one selected from the group consisting of a (C1-C6)alkyl; a (C6-C20)aryl unsubstituted or substituted with a (C1-C6)alkyl(s); a (3- to 30-membered)heteroaryl unsubstituted or substituted with a (C6-C20)aryl(s); and a di(C6-C20)arylamino unsubstituted or substituted with a (C1-C6)alkyl(s). Specifically, the substituent may be at least one of methyl, phenyl, naphthyl, biphenyl, dimethylfluorenyl, dimethylbenzofluorenyl, diphenyltriazinyl, phenylnaphthyltriazinyl, phenylbiphenyltriazinyl, naphthylbiphenyltriazinyl, dibenzothiophenyl, phenyldimethylbenzofluorenylamino, and biphenyldimethylbenzofluorenylamino.

Formula 1 may be represented by the following formula 2 or 3.

(2)
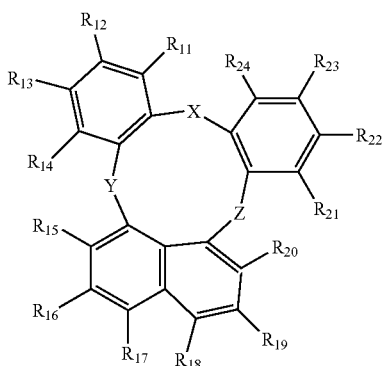
(3)
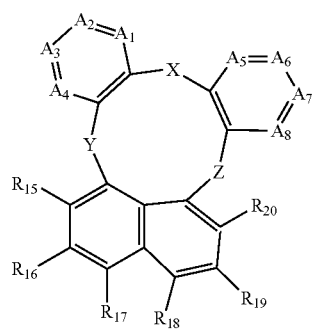
wherein
X, Y, Z, and $A_1$ to $A_8$ are as defined in formula 1, with a proviso that at least one of $A_1$ to $A_8$ is N; and
$R_{11}$ to $R_{24}$ are identical to $R_4$ in formula 1.
Formula 1 may be represented by any one of the following formulas.
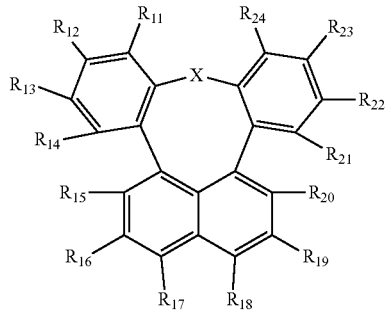
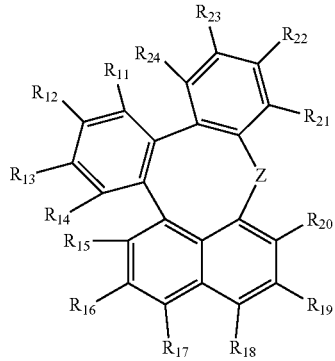
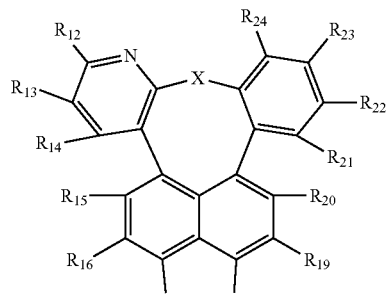
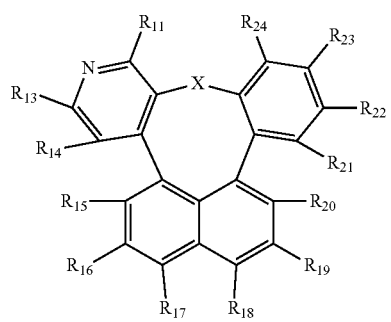
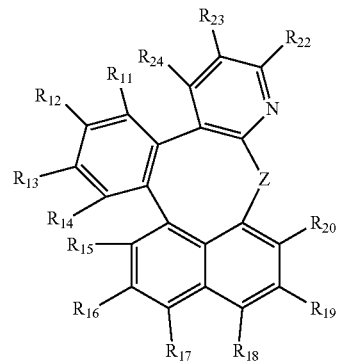
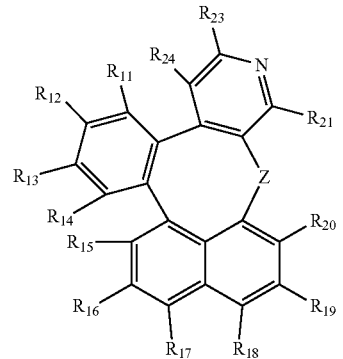
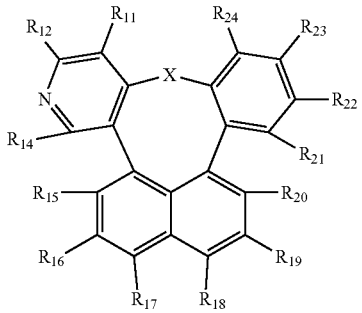

-continued

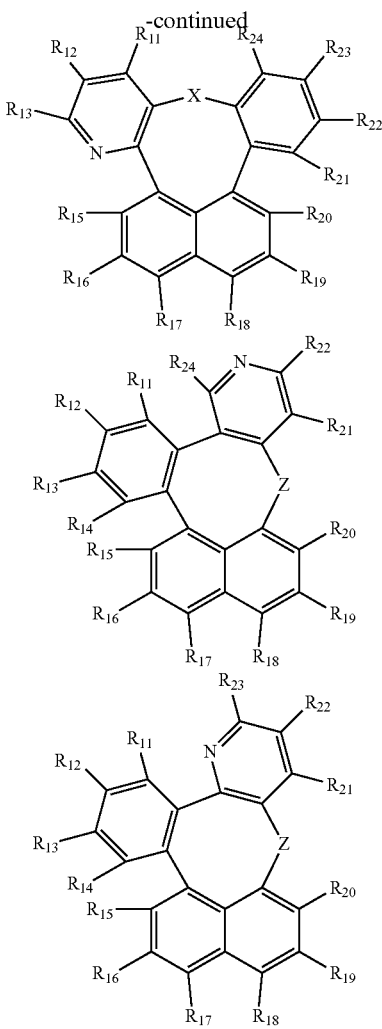

wherein

X and Z each independently represent O, S, NR$_1$, or CR$_2$R$_3$;

R$_1$ to R$_3$ are as defined in formula 1; and

R$_{11}$ to R$_{24}$ are identical to R$_4$ in formula 1.

In formula 1 above, X, Y, and Z each independently represent a single bond, O, S, NR$_1$, or CR$_2$R$_3$, with a proviso that not all of X, Y, and Z are a single bond. According to one embodiment of the present disclosure, X represents a single bond, O, S, NR$_1$, or CR$_2$R$_3$, and Y and Z each independently represent a single bond, O, S, or NR$_1$.

R$_1$ to R$_3$ each independently represent hydrogen, deuterium, a halogen, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino; or R$_2$ and R$_3$ may be linked to each other to form a ring(s), where if a plurality of R$_1$ to R$_3$ is present, each of R$_1$, each of R$_2$, and each of R$_3$ may be the same or different. According to one embodiment of the present disclosure, R$_1$ represents a substituted or unsubstituted (C6-C30)aryl, or a substituted or unsubstituted (5- to 15-membered)heteroaryl, and R$_2$ and R$_3$ each independently represent a substituted or unsubstituted (C1-C6)alkyl, or a substituted or unsubstituted (C6-C12)aryl. According to another embodiment of the present disclosure, R$_1$ represents a (C6-C30)aryl unsubstituted or substituted with one or more of a (C1-C6)alkyl(s), a (C6-C20)aryl(s), a (5- to 15-membered)heteroaryl(s), and a di(C6-C20)arylamino(s); or a (5- to 15-membered)heteroaryl unsubstituted or substituted with a (C6-C12)aryl(s), and R$_2$ and R$_3$ each independently represent an unsubstituted (C1-C6)alkyl, or an unsubstituted (C6-C12)aryl. Specifically, R$_1$ may represent a phenyl, a naphthyl, a biphenyl, a naphthylphenyl, a phenylnaphthyl, a dimethylfluorenyl, a diphenylfluorenyl, a dimethylbenzofluorenyl, a diphenylbenzofluorenyl, a spirobifluorenyl, a spiro[fluorene-benzofluoren]yl, a phenyl substituted with a dimethylbenzofluorenyl, a biphenyl substituted with a dimethylbenzofluorenyl, a phenyl substituted with a diphenyltriazinyl, a phenyl substituted with a phenylnaphthyltriazinyl, a phenyl substituted with a dibenzothiophenyl and a dimethylfluorenyl, a phenyl substituted with a phenyldimethylbenzofluorenylamino, a phenyl substituted with a biphenyldimethylbenzofluorenylamino, a naphthyl substituted with a diphenyltriazinyl, a dimethylfluorenyl substituted with a phenyl, a diphenyltriazinyl, a triazinyl substituted with a phenyl and a naphthyl, a triazinyl substituted with a phenyl and a biphenyl, a triazinyl substituted with a naphthyl and a biphenyl, a dibiphenyltriazinyl, etc., and R$_2$ and R$_3$ may each independently represent a methyl, a phenyl, etc.

A$_1$ to A$_{14}$ each independently represent CR$_4$ or N.

R$_4$ each independently represents hydrogen, deuterium, a halogen, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino; or two or more adjacent R$_4$'s may be linked to each other to form a ring(s). According to one embodiment of the present disclosure, R$_4$ each independently represents hydrogen, a substituted or unsubstituted (C6-C30)aryl, a substituted or unsubstituted (5- to 15-membered)heteroaryl, or a substituted or unsubstituted di(C6-C20)arylamino. According to another embodiment of the present disclosure, R$_4$ each independently represents hydrogen; a (C6-C30)aryl unsubstituted or substituted with one or more of a (C6-C12)aryl(s) and a (5- to 15-membered)heteroaryl(s); a (5- to 15-membered)heteroaryl unsubstituted or substituted with a (C6-C12)aryl(s); or a di(C6-C20)arylamino unsubstituted or substituted with a (C1-C6)alkyl(s). Specifically, R$_4$ may each independently represent hydrogen, an anthracenyl substituted with a phenyl, an anthracenyl substituted with a naphthyl, an anthracenyl substituted with a biphenyl, a phenyl substituted with a diphenyltriazinyl, a phenyl substituted with a phenylbiphenyltriazinyl, a phenyl substituted with a naphthylbiphenyltriazinyl, a diphenyltriazinyl, a triazinyl substituted with a phenyl and a biphenyl, a triazinyl substituted with a naphthyl and a biphenyl, a diphenylamino, a dibiphenylamino, a biphenyldimethylfluorenylamino, a terphenyldimethylfluorenylamino, etc.

According to one embodiment of the present disclosure, in formula 1 above, $R_1$ represents a substituted or unsubstituted (C6-C30)aryl, or a substituted or unsubstituted (5- to 15-membered)heteroaryl; $R_2$ and $R_3$ each independently represent a substituted or unsubstituted (C1-C6)alkyl, or a substituted or unsubstituted (C6-C12)aryl; and $R_4$ each independently represents hydrogen, a substituted or unsubstituted (C6-C30)aryl, a substituted or unsubstituted (5- to 15-membered)heteroaryl, or a substituted or unsubstituted di(C6-C20)arylamino.

According to another embodiment of the present disclosure, in formula 1 above, $R_1$ represents a (C6-C30)aryl unsubstituted or substituted with one or more of a (C1-C6) alkyl(s), a (C6-C20)aryl(s), a (5- to 15-membered)heteroaryl(s), and a di(C6-C20)arylamino(s); or a (5- to 15-membered)heteroaryl unsubstituted or substituted with a (C6-C12)aryl(s), $R_2$ and $R_3$ each independently represent an unsubstituted (C1-C6)alkyl, or an unsubstituted (C6-C12) aryl, and $R_4$ each independently represents hydrogen; a (C6-C30)aryl unsubstituted or substituted with one or more of a (C6-C12)aryl(s) and a (5- to 15-membered)heteroaryl(s); a (5- to 15-membered)heteroaryl unsubstituted or substituted with a (C6-C12)aryl(s); or a di(C6-C20)arylamino unsubstituted or substituted with a (C1-C6)alkyl(s).

In the formulas of the present disclosure, if a substituent is linked to an adjacent substituent to form a ring, the ring, which is formed by linkages of at least two adjacent substituents, may be a substituted or unsubstituted, mono- or polycyclic, alicyclic or aromatic (3- to 30-membered) ring, or the combination thereof, in which the formed ring may contain at least one heteroatom selected from B, N, O, S, Si, and P, preferably, at least one heteroatom selected from N, O, and S. According to one embodiment of the present disclosure, the number of the ring backbone atoms is 5 to 20, and according to another embodiment of the present disclosure, the number of the ring backbone atoms is 5 to 15. For example, the fused ring may be a substituted or unsubstituted dibenzothiophene ring, a substituted or unsubstituted dibenzofuran ring, a substituted or unsubstituted naphthalene ring, a substituted or unsubstituted phenanthrene ring, a substituted or unsubstituted fluorene ring, a substituted or unsubstituted benzothiophene ring, a substituted or unsubstituted benzofuran ring, a substituted or unsubstituted indole ring, a substituted or unsubstituted indene ring, a substituted or unsubstituted benzene ring, or a substituted or unsubstituted carbazole ring.

In the formulas of the present disclosure, the heteroaryl may each independently contain at least one heteroatom selected from B, N, O, S, Si, and P. In addition, the heteroatom may be bonded to at least one selected from the group consisting of hydrogen, deuterium, a halogen, a cyano, a substituted or unsubstituted (C1-C30)alkyl, a substituted or unsubstituted (C6-C30)aryl, a substituted or unsubstituted (5- to 30-membered)heteroaryl, a substituted or unsubstituted (C3-C30)cycloalkyl, a substituted or unsubstituted (C1-C30)alkoxy, a substituted or unsubstituted tri (C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, and a substituted or unsubstituted (C1-C30)alkyl(C6-C30)arylamino.

The compound represented by formula 1 includes the following compounds, but is not limited thereto.

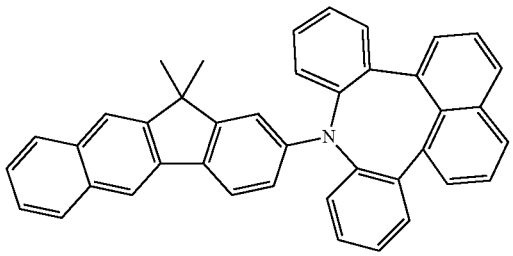

A-1

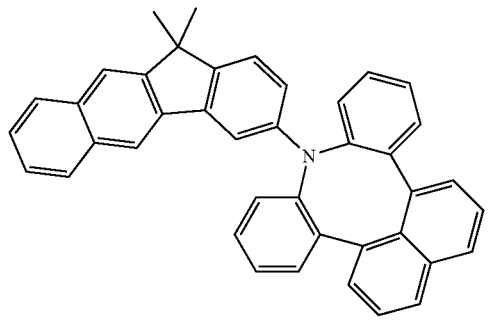

A-2

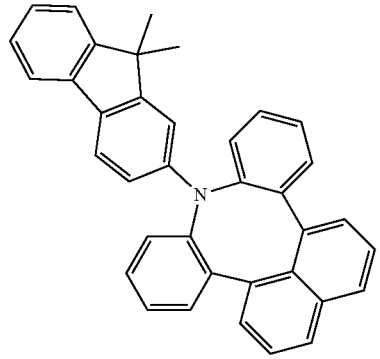

A-3

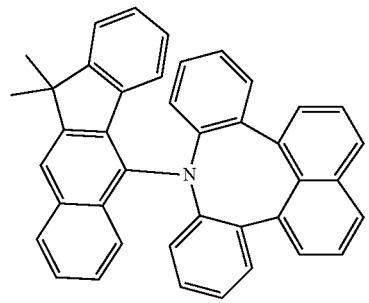

A-4

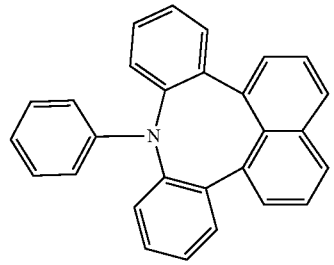

A-5

A-6
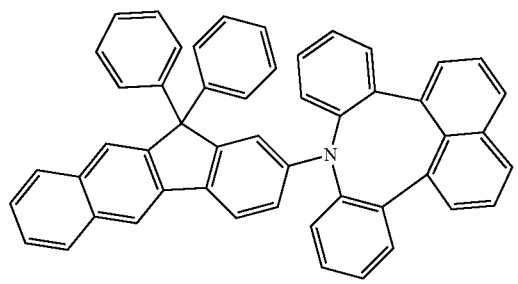
A-7
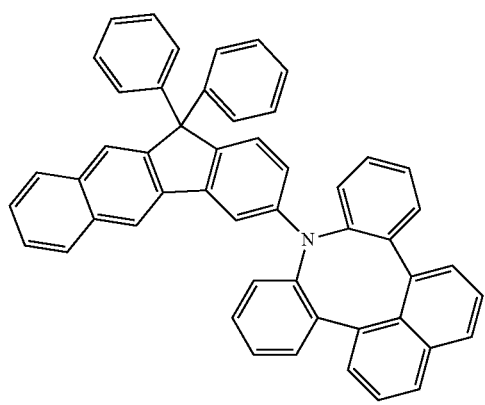
A-8
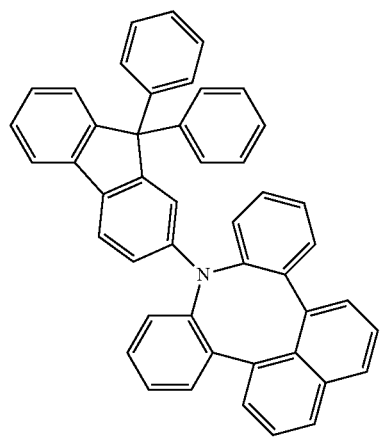
A-9
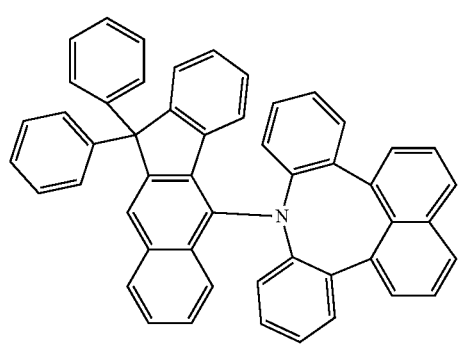
A-10
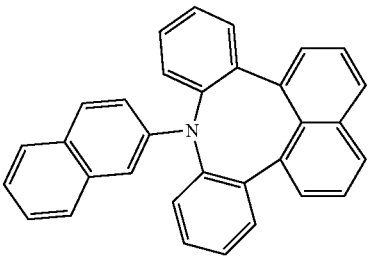
A-11
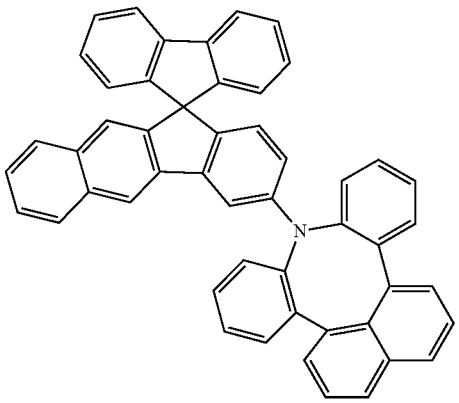
A-12
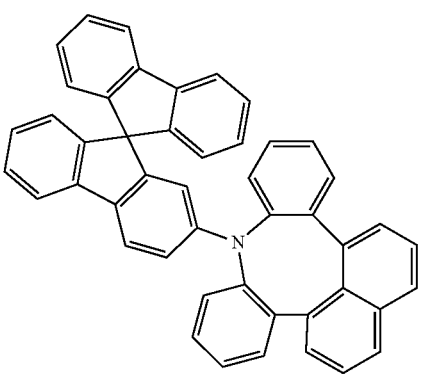
A-13

A-14
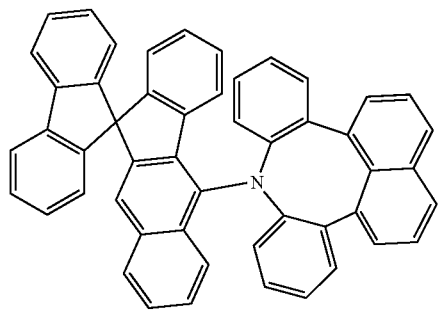
A-15
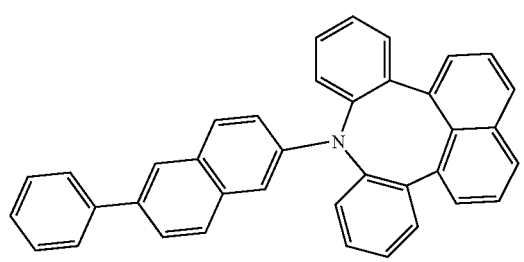
A-16
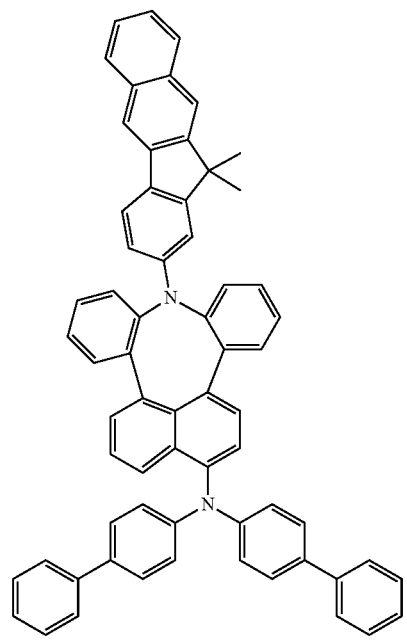
A-17
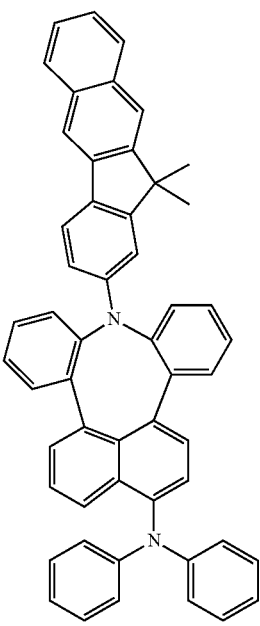
A-18
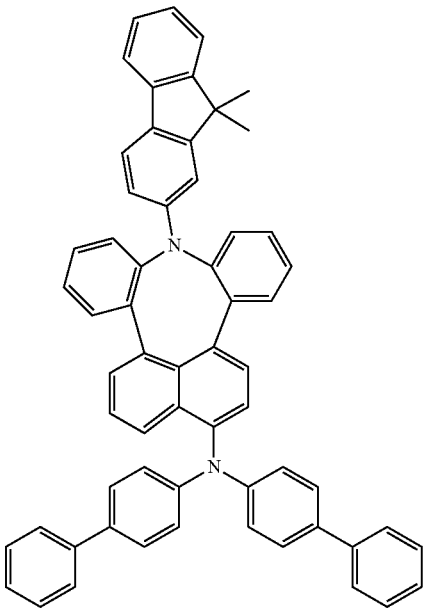

A-19
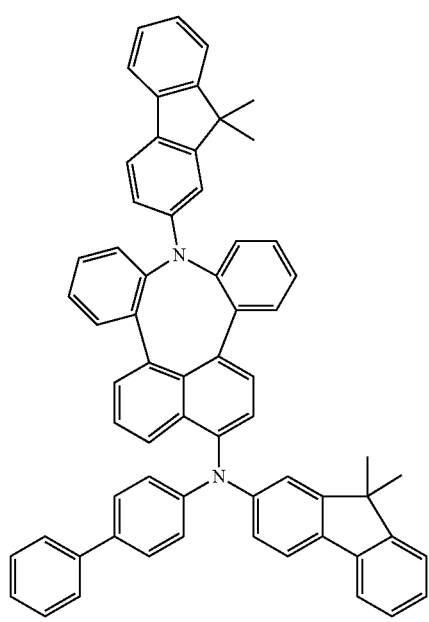
A-20
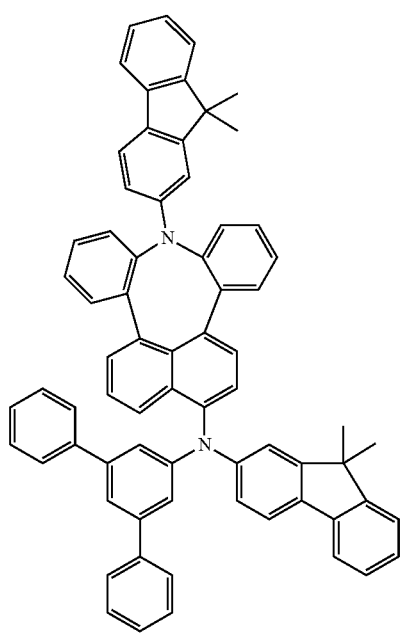
A-21
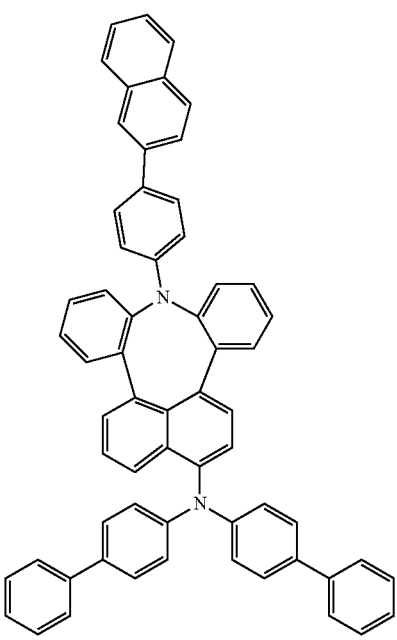
A-22
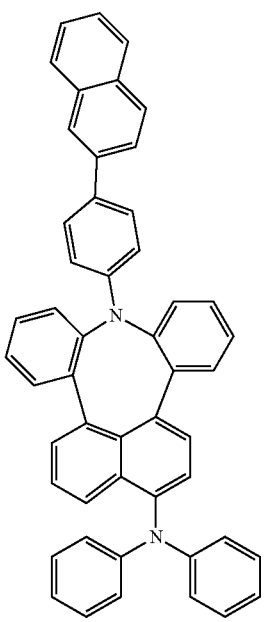

A-23
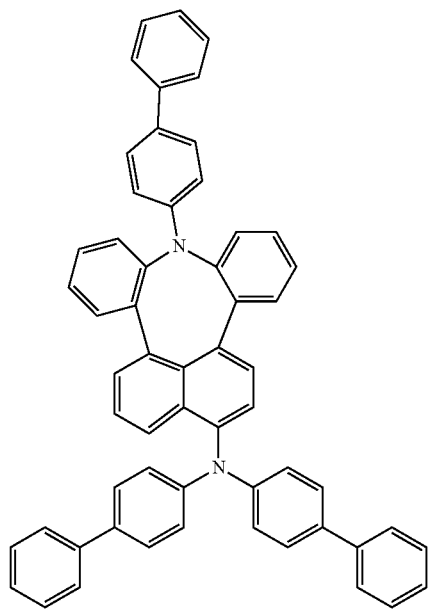
A-24
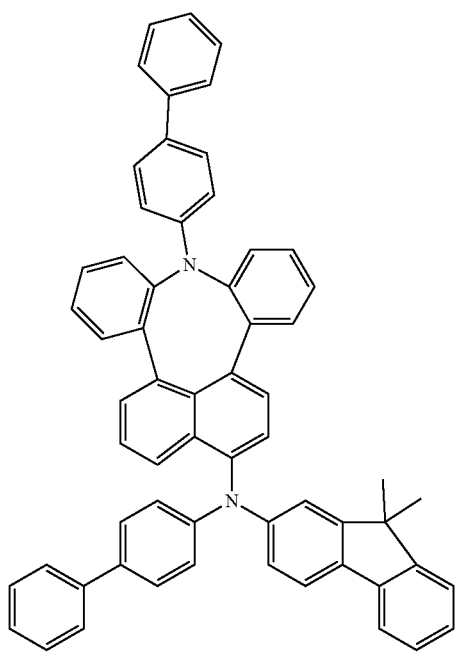
A-25
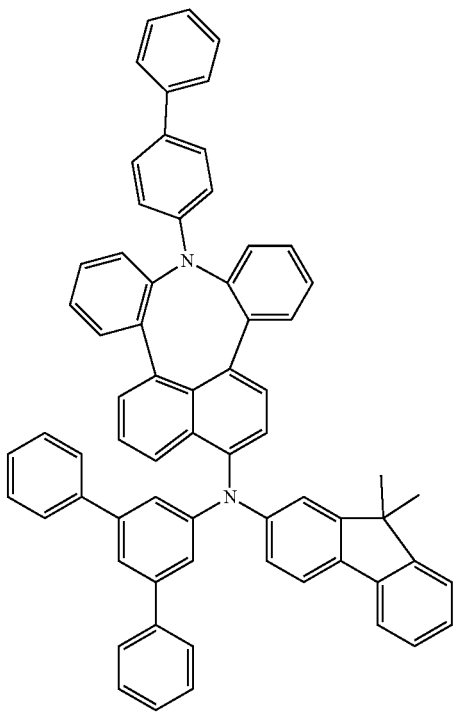
A-26
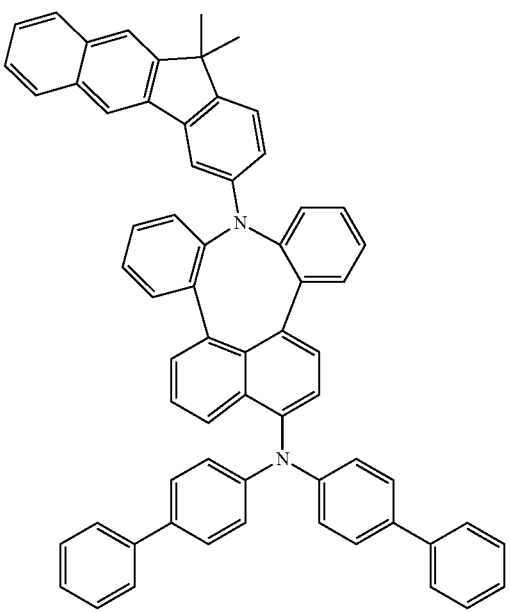

A-27
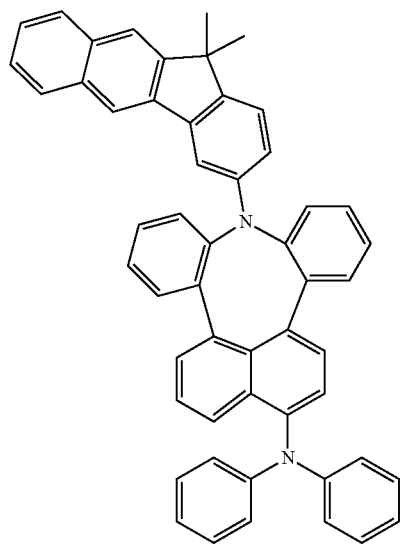
A-28
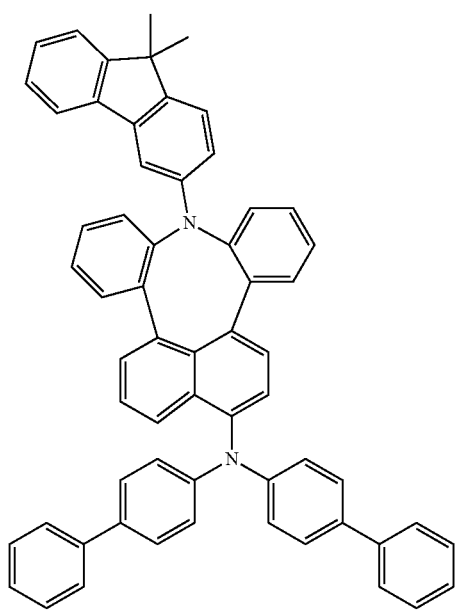
A-29
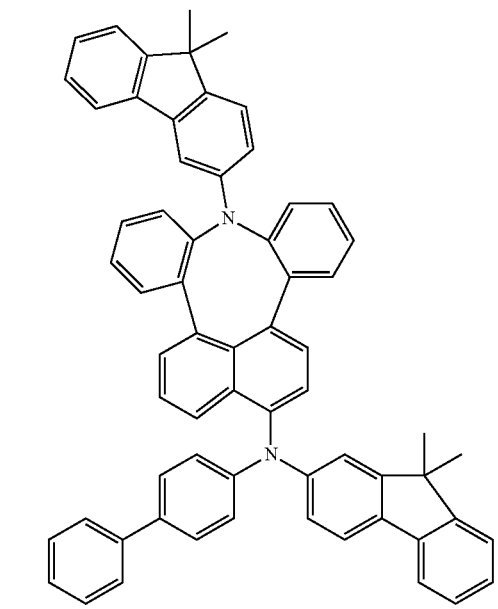
A-30
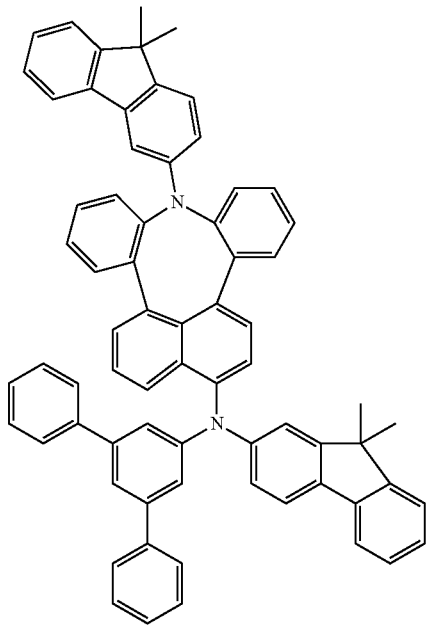

A-31
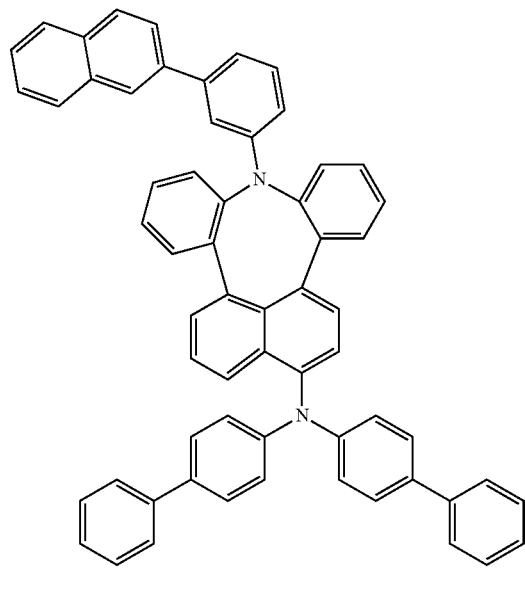
A-33
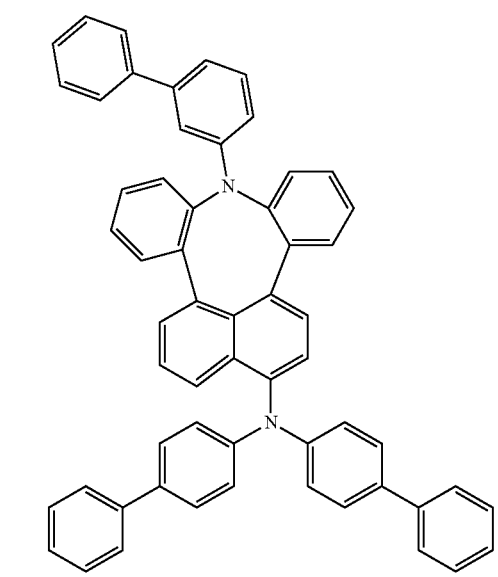
A-32
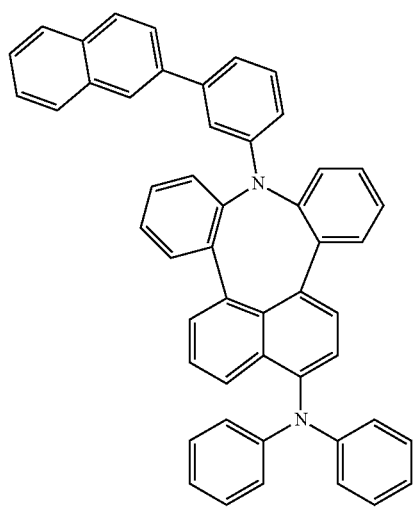
A-34
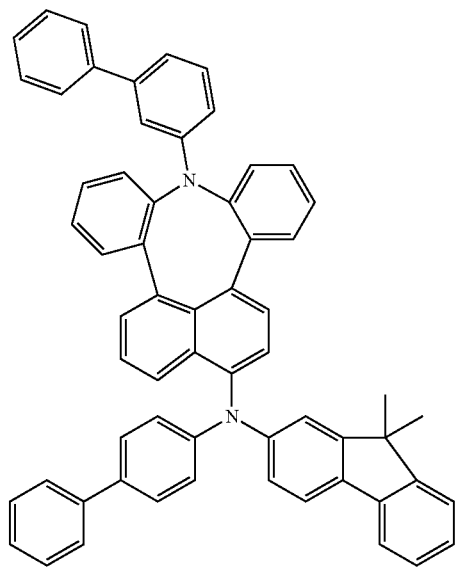

A-35
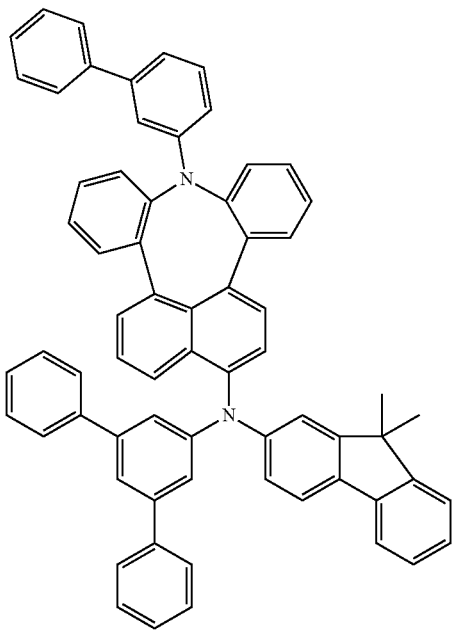
A-36
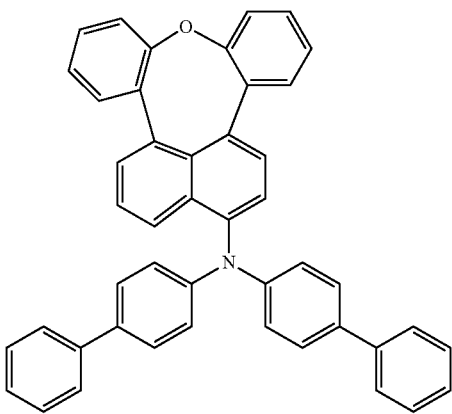
A-37
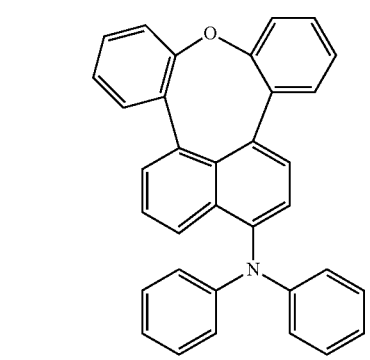
A-38
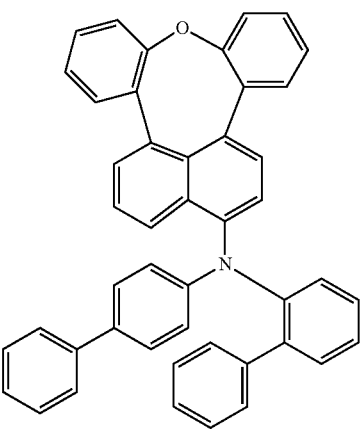
A-39
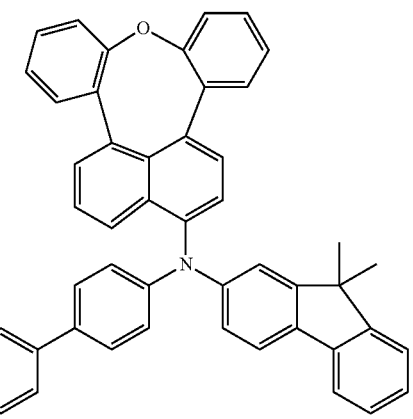
A-40
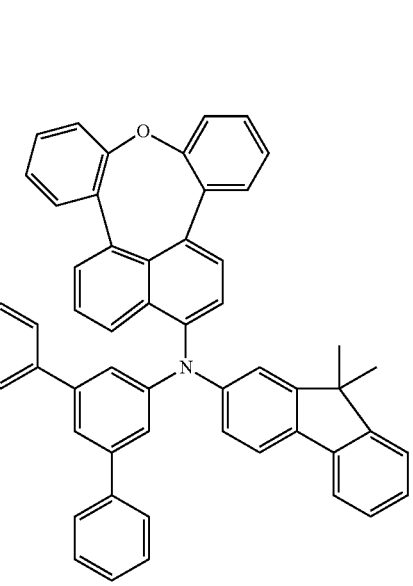

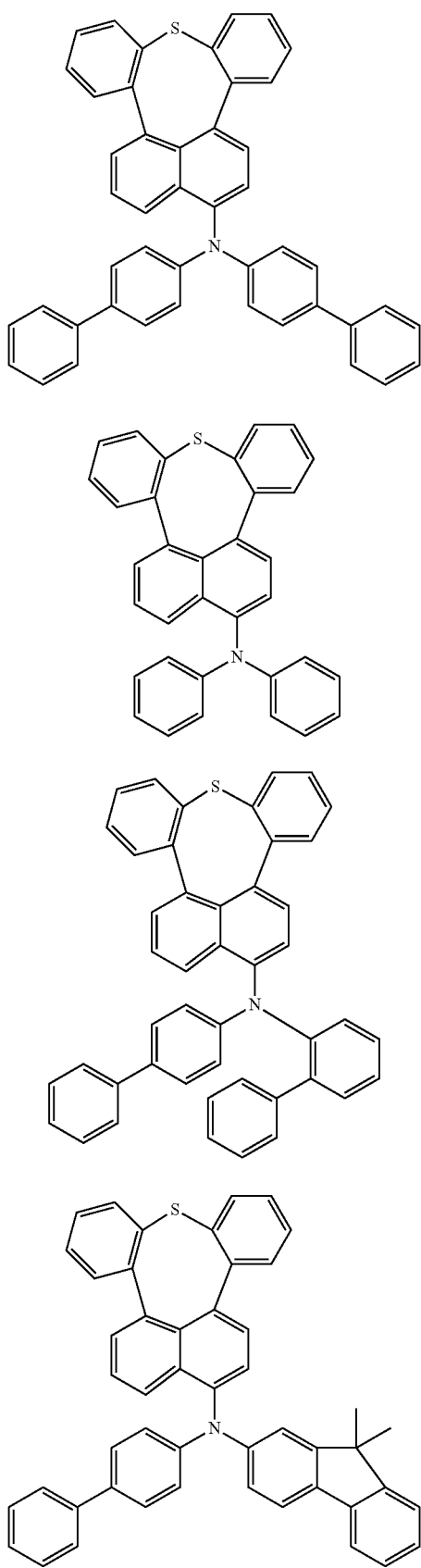
A-41
A-42
A-43
A-44
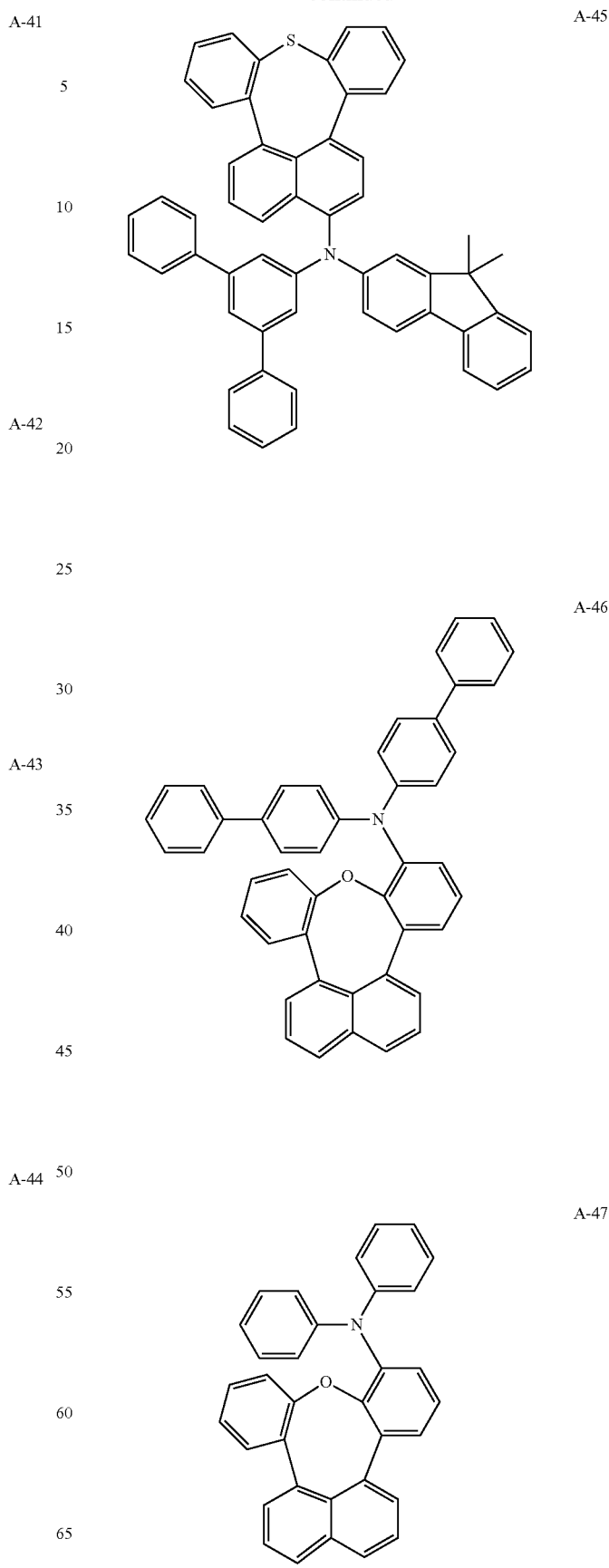
A-45
A-46
A-47

A-48
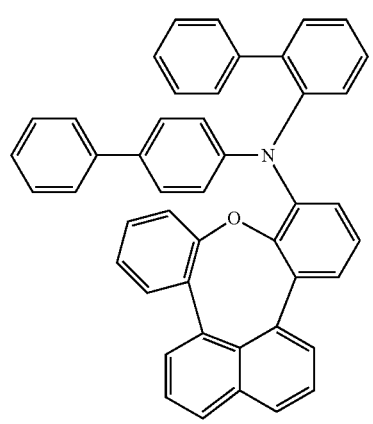
A-49
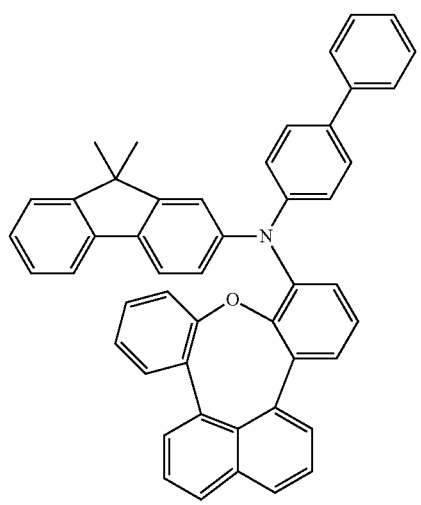
A-50
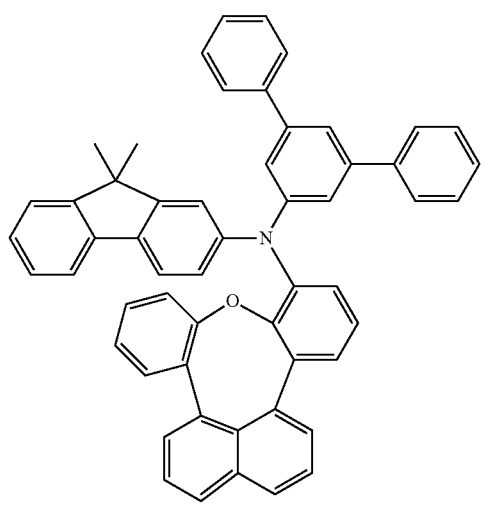
A-51
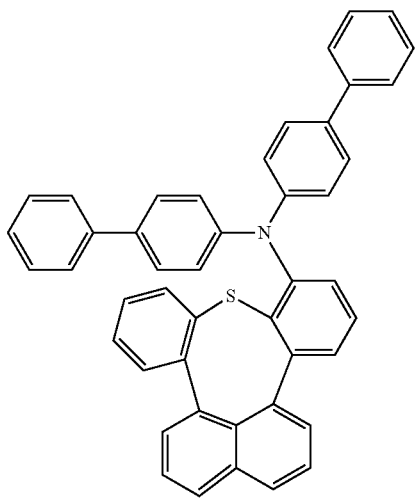
A-52
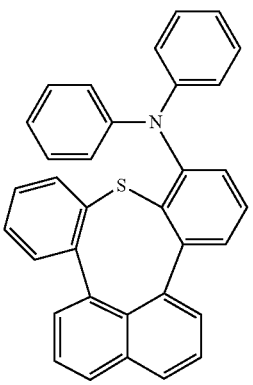
A-53
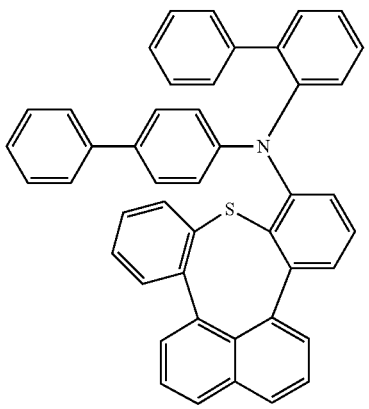

A-54
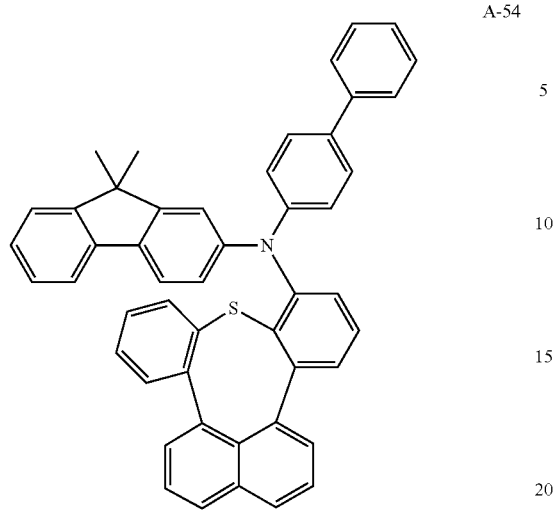
A-57
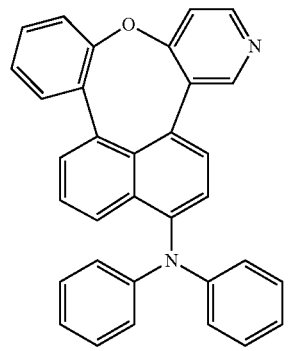
A-55
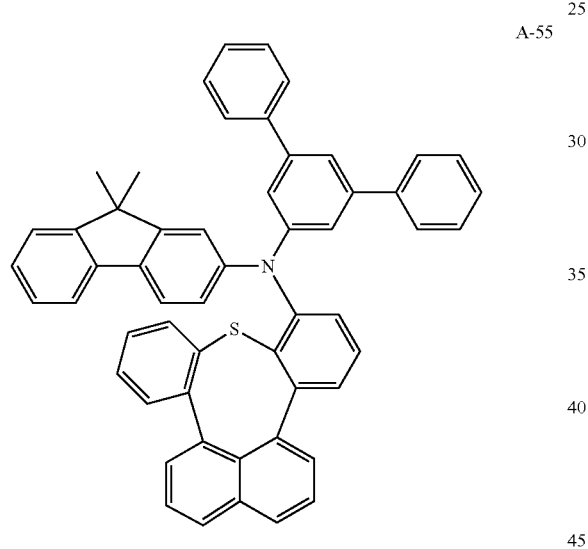
A-58
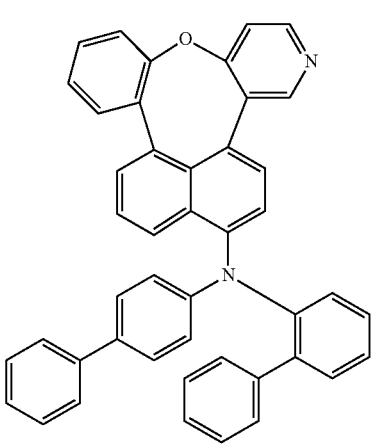
A-56
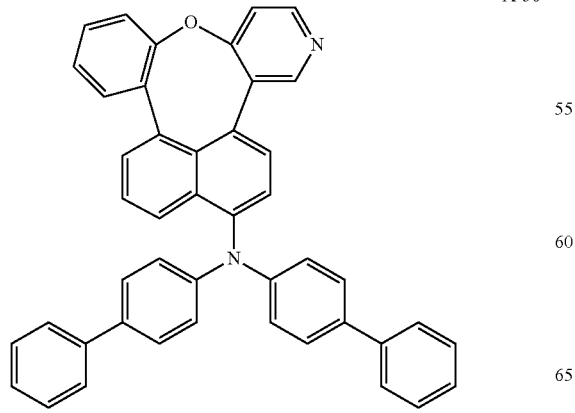
A-59
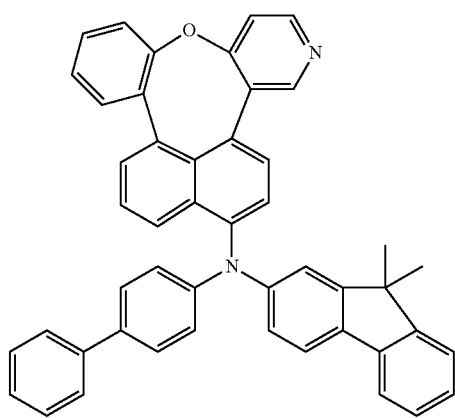

-continued
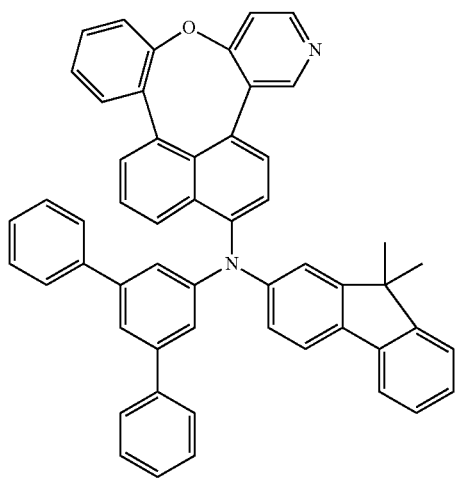
A-60
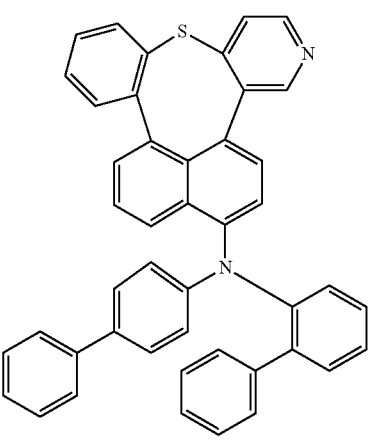
A-63
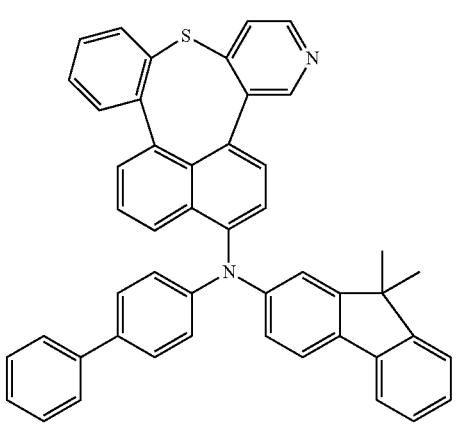
A-64
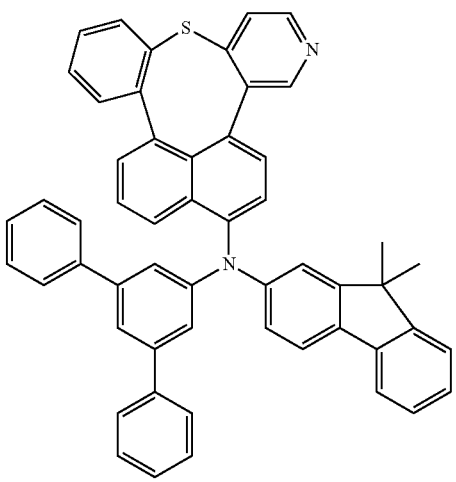
A-65
A-61
A-62

A-66
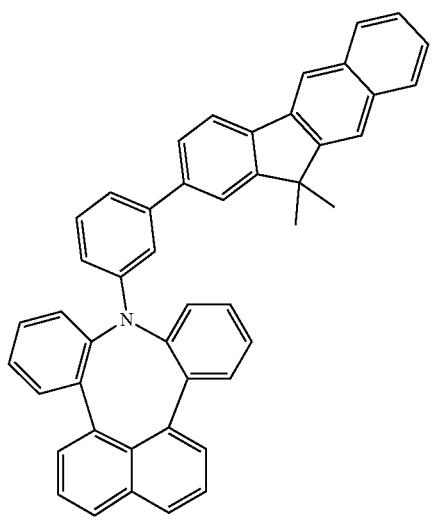
A-69
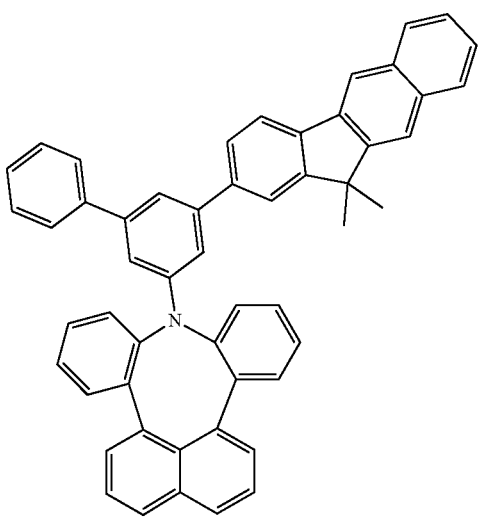
A-67
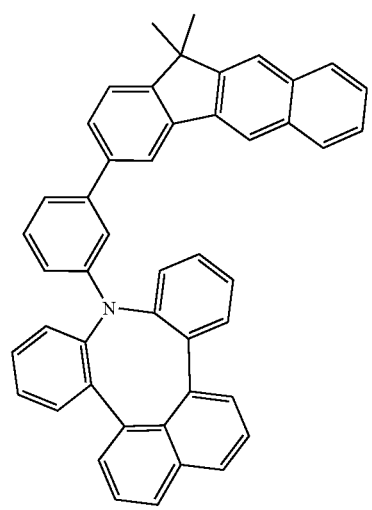
A-70
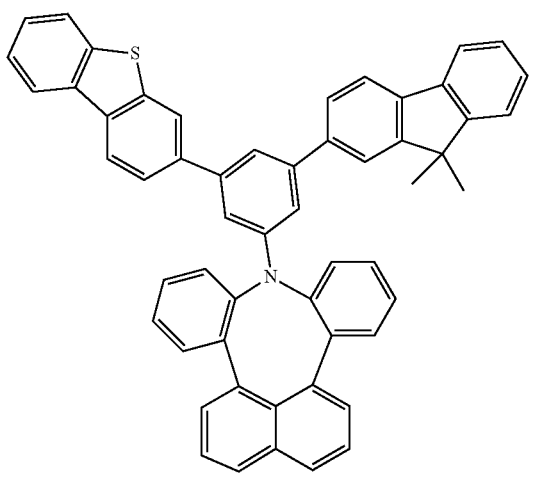
A-68
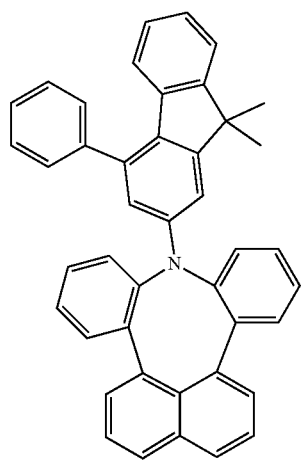
A-71
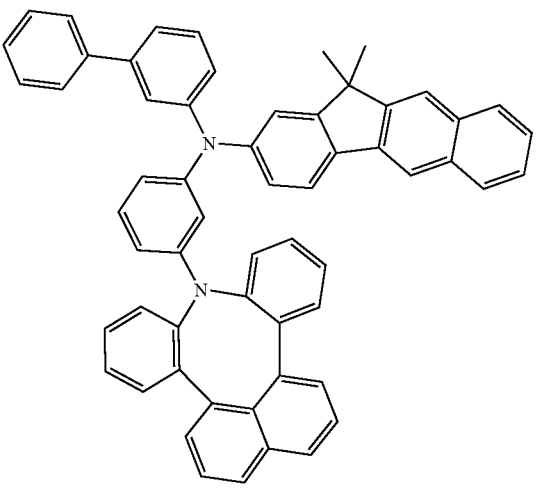

A-72
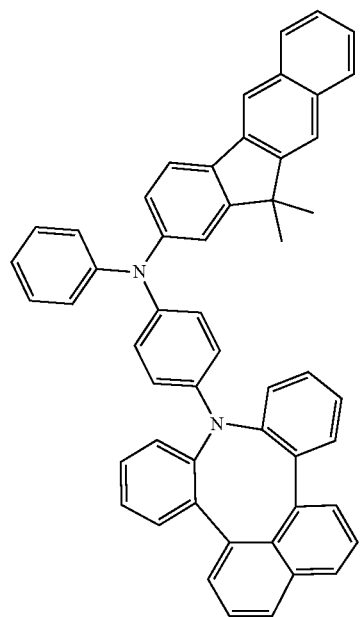
A-73
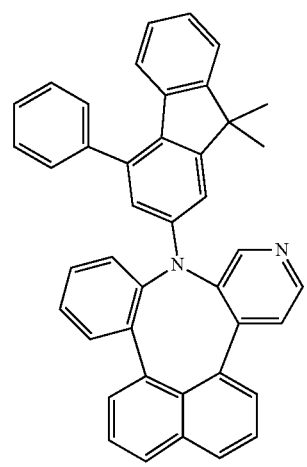
A-74
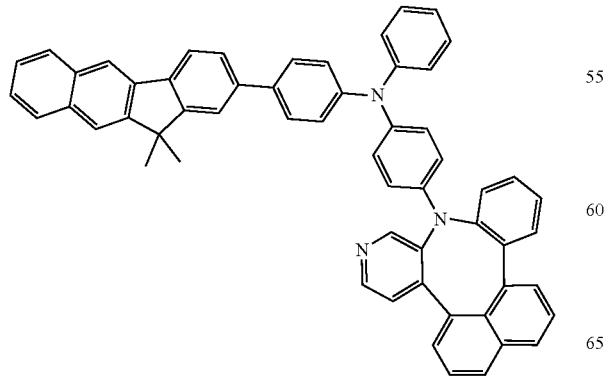
A-75
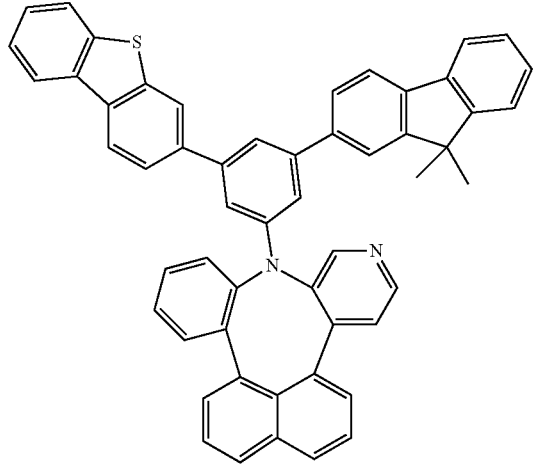
A-76
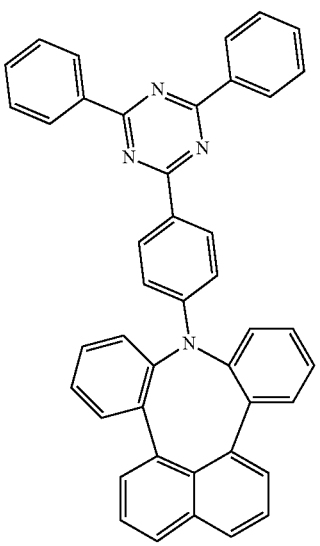
A-77
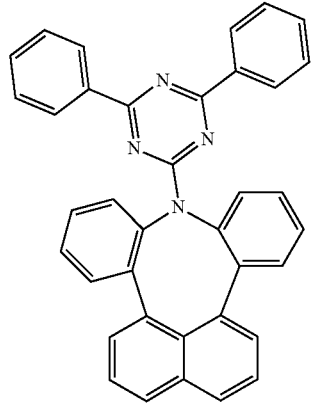

A-78
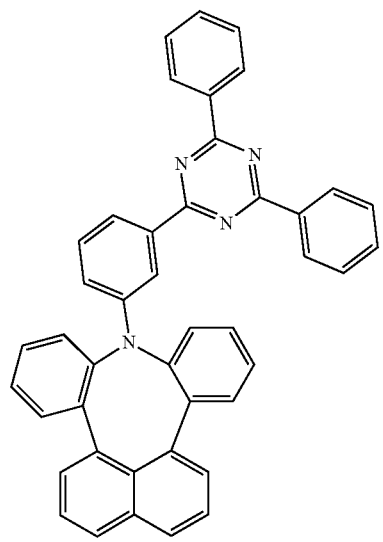
A-79
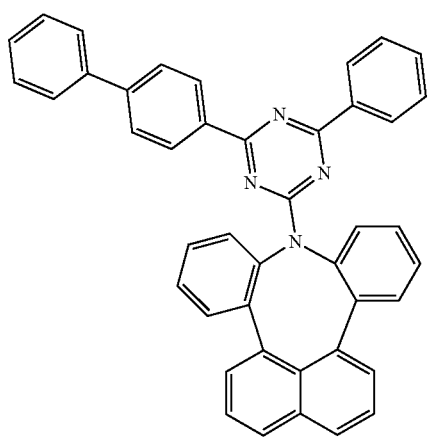
A-80
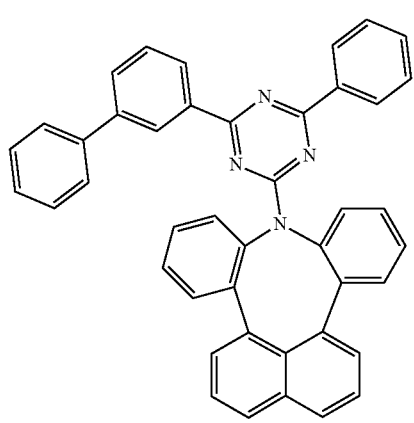
A-81
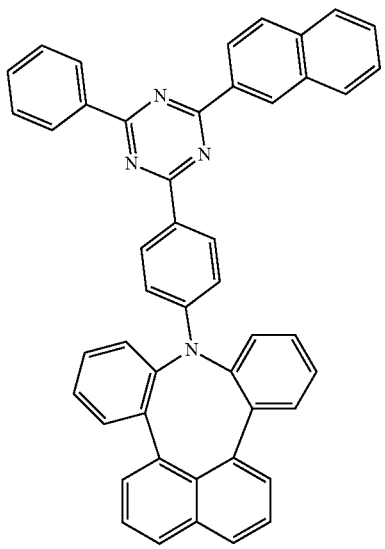
A-82
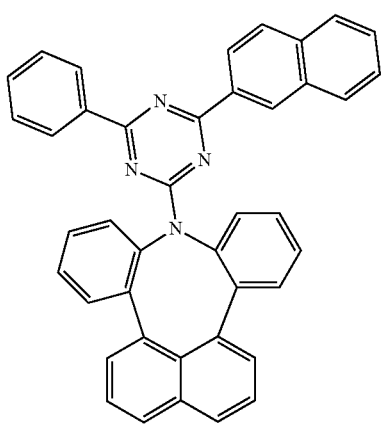
A-83
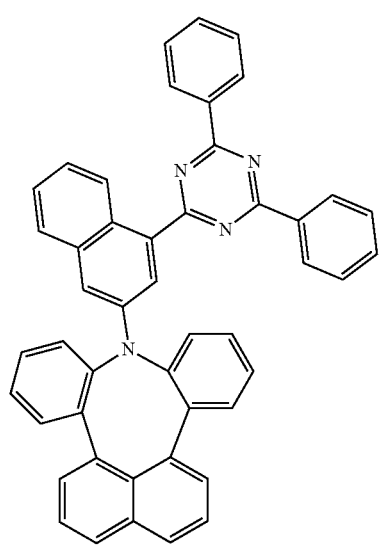

A-84
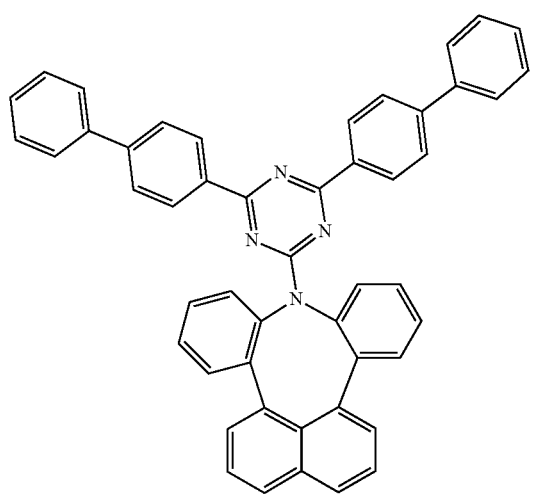
A-85
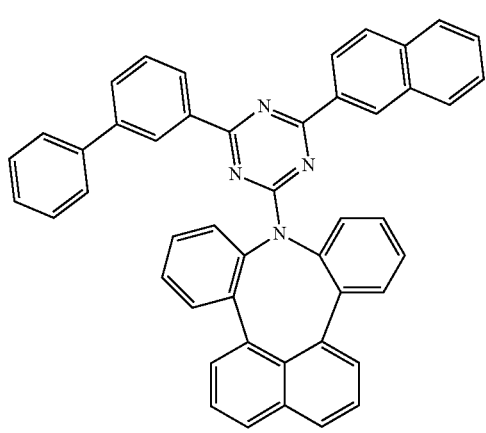
A-86
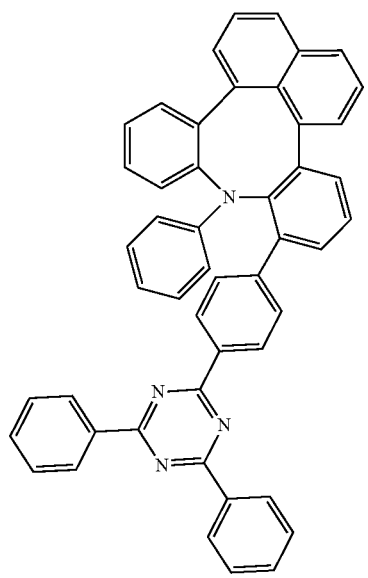
A-87
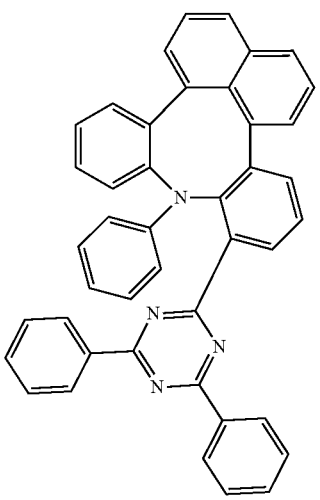
A-88
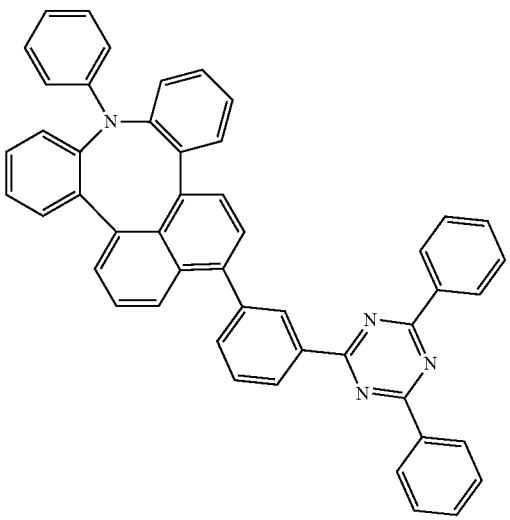
A-89
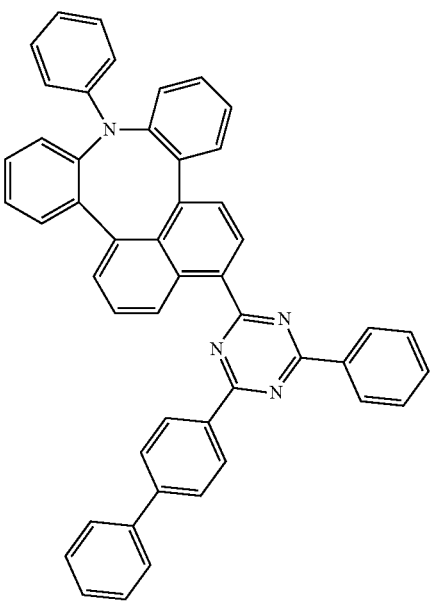

A-90
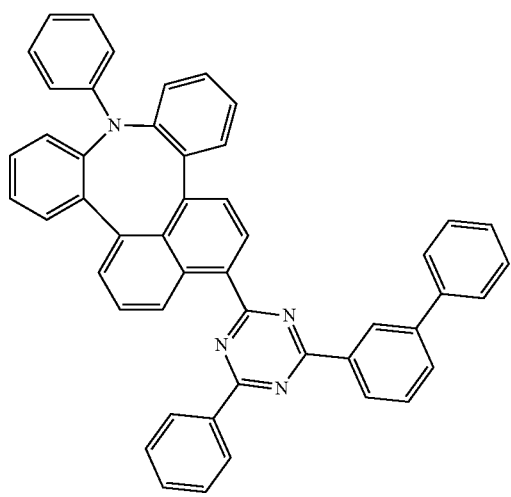
A-91
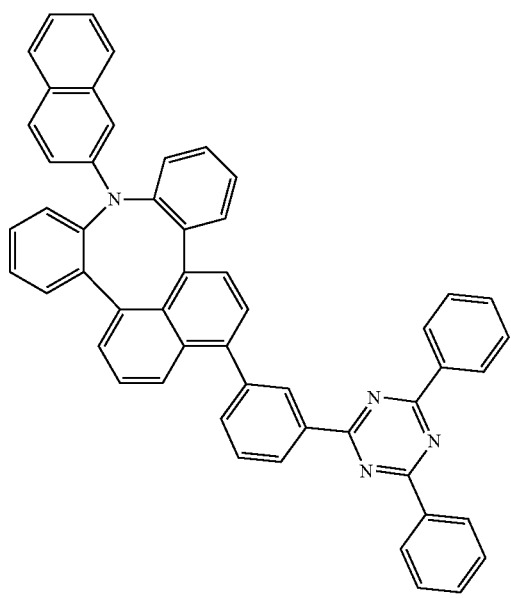
A-92
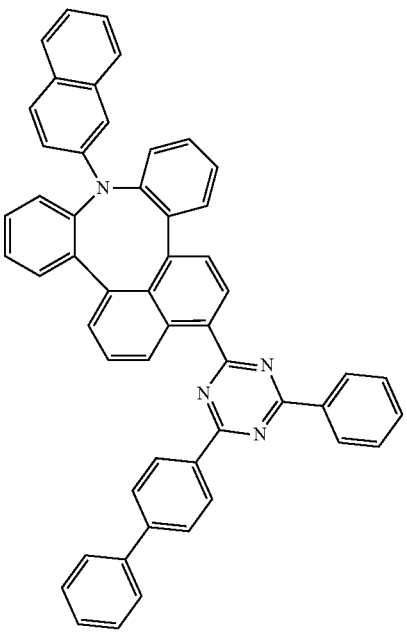
A-93
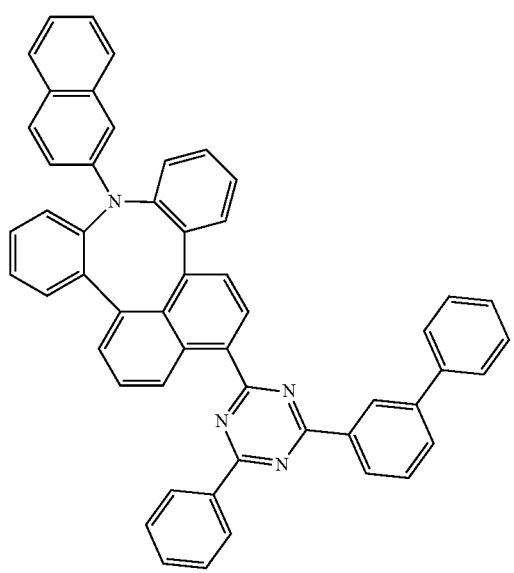

A-94
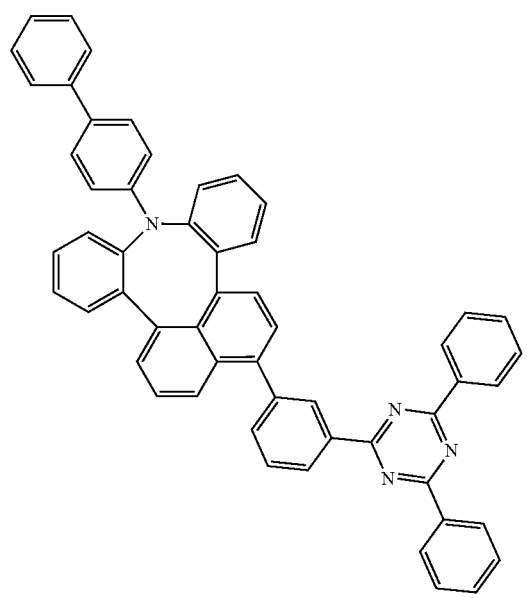
A-95
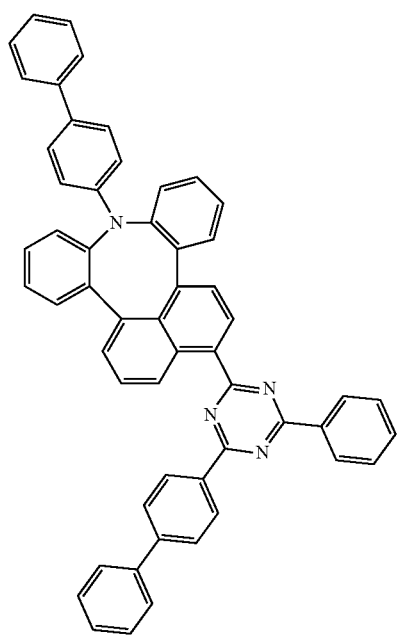
A-96
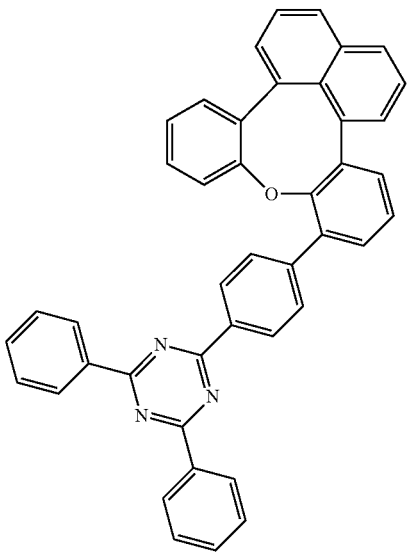
A-97
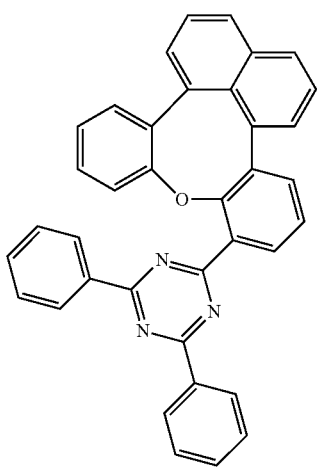
A-98
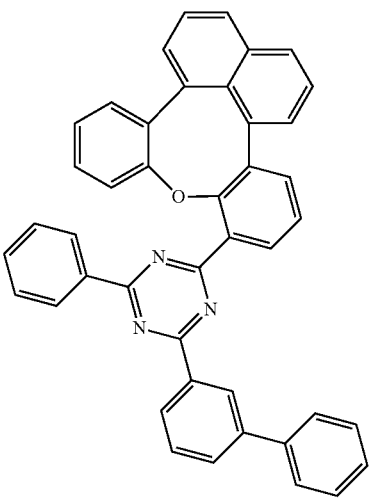

A-99
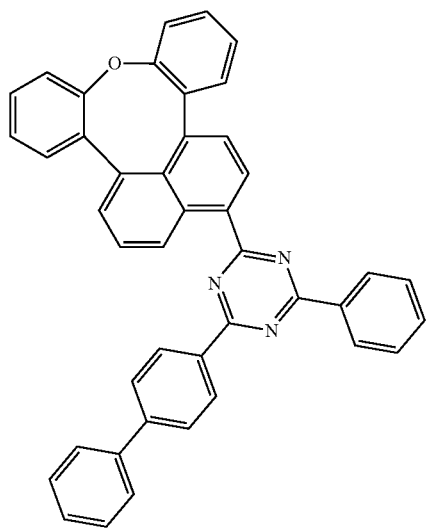
A-100
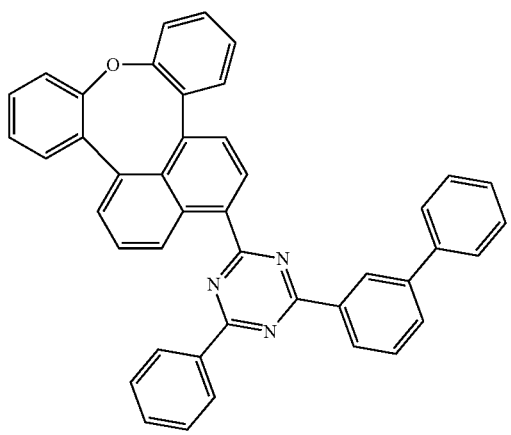
A-101
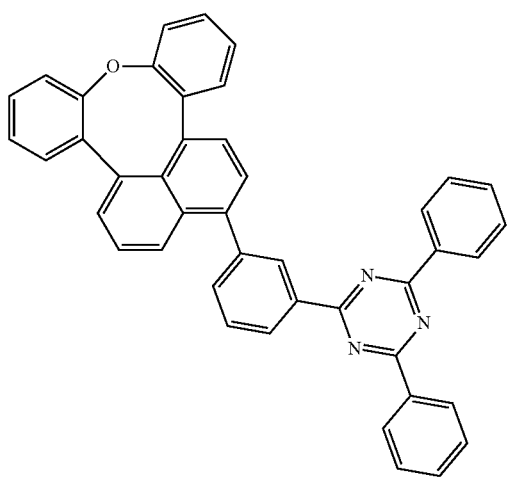
A-102
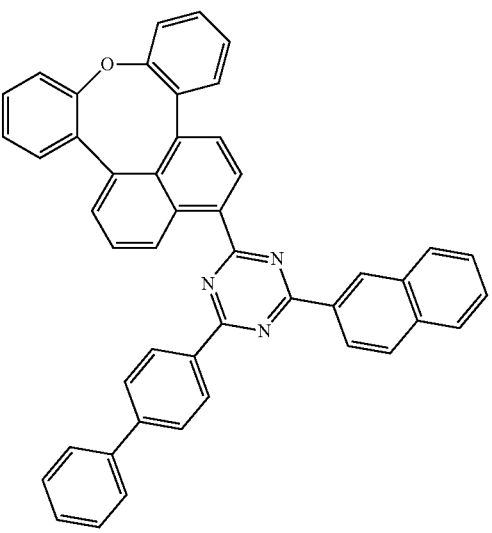
A-103
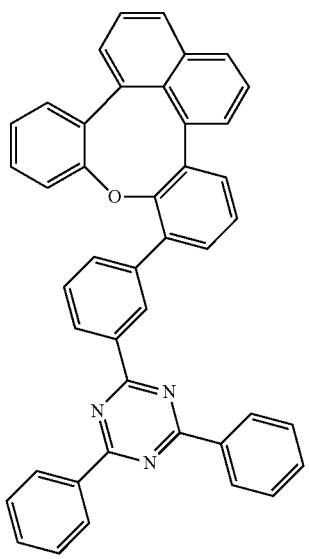
A-104
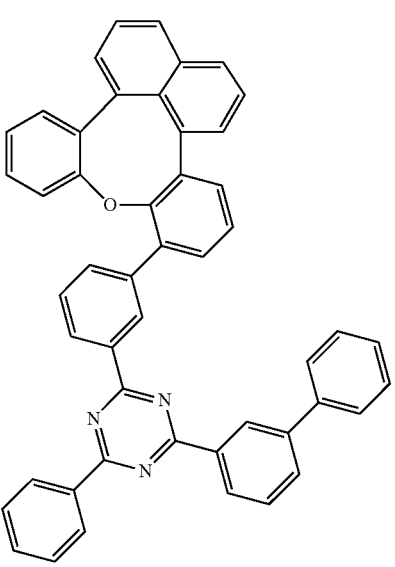

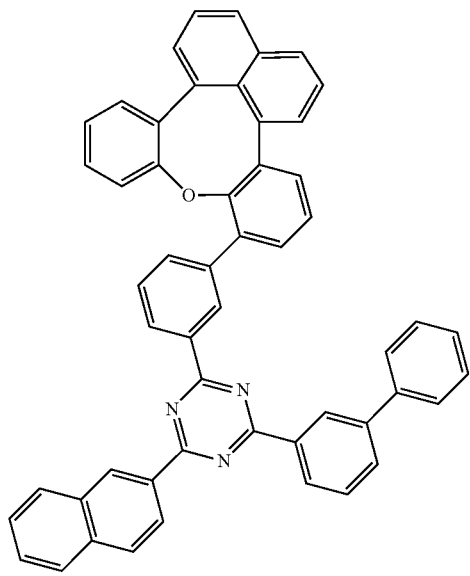
A-105
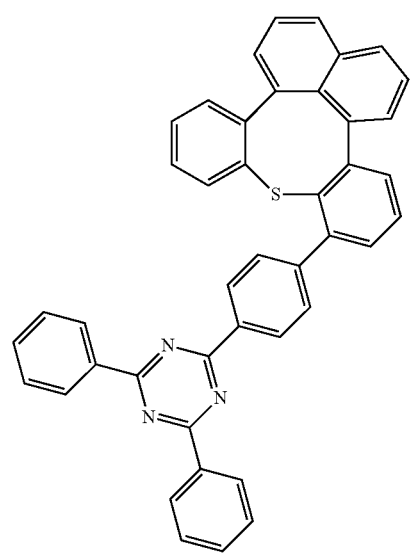
A-106
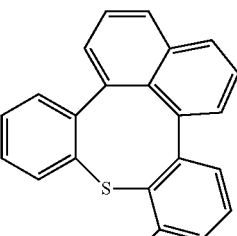
A-107
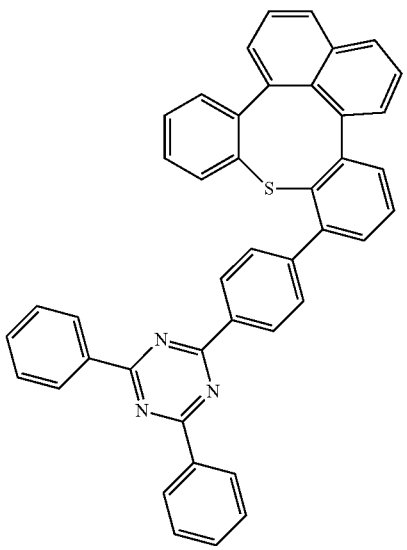
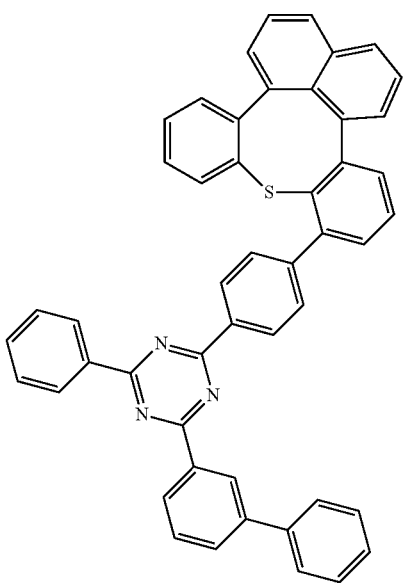
A-108
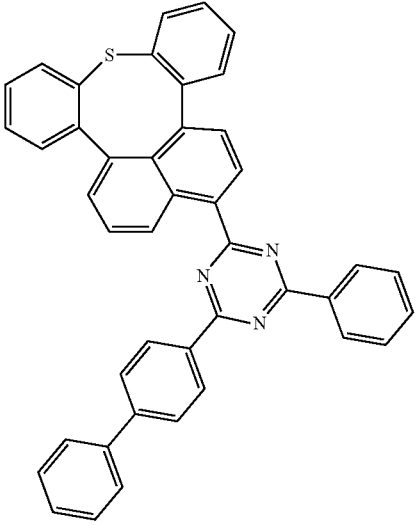
A-109

A-110
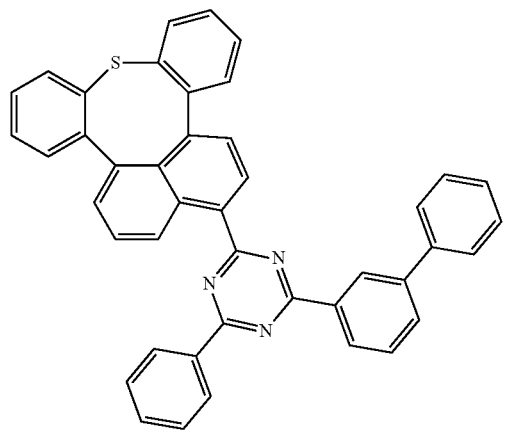
A-111
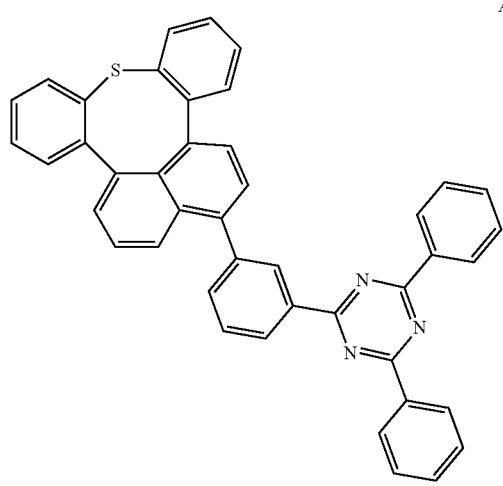
A-112
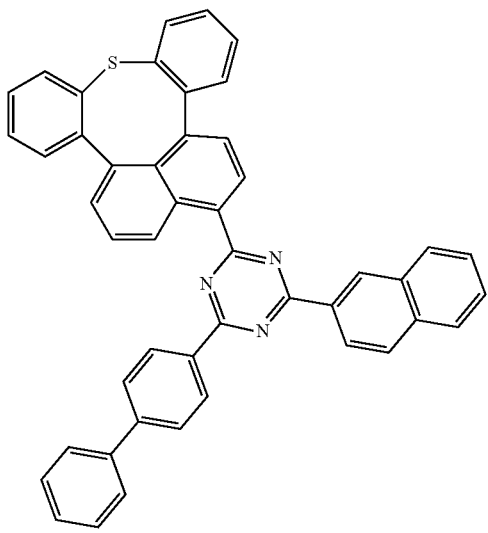
A-113
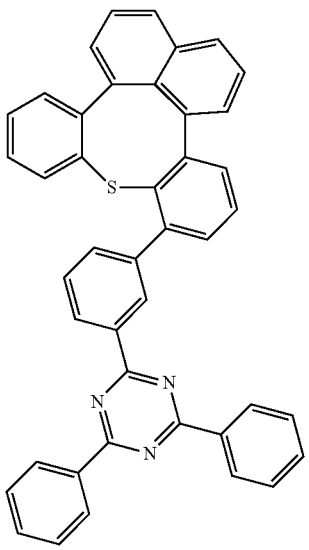
A-114
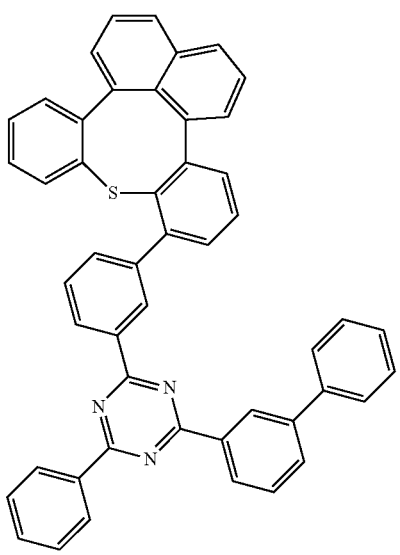
A-115
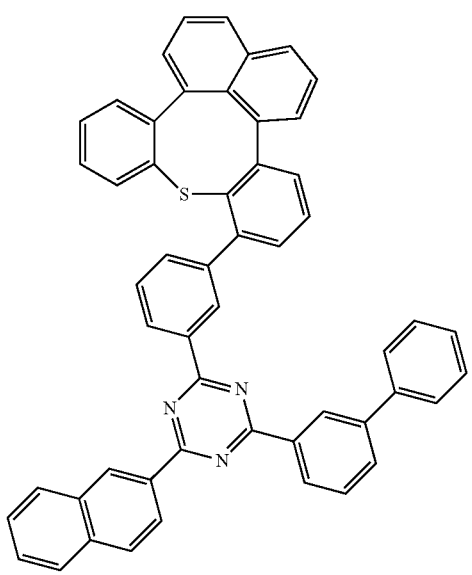

-continued
A-116
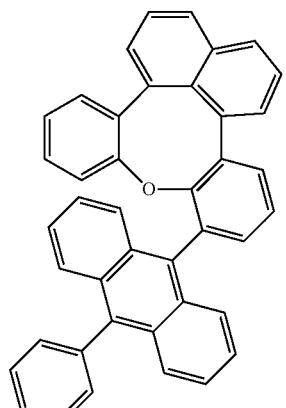
A-117
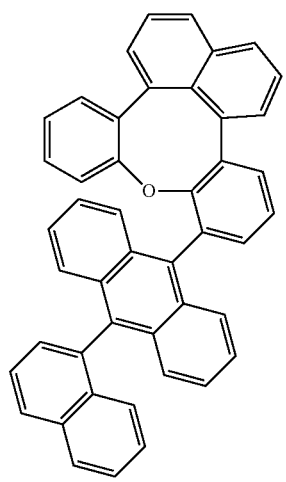
A-118
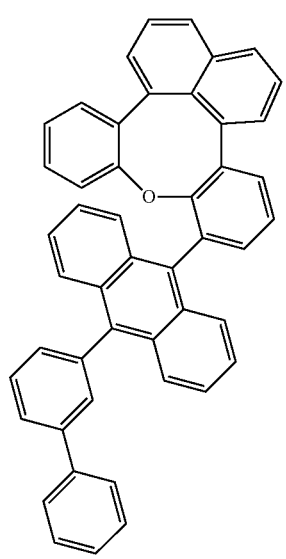
-continued
A-119
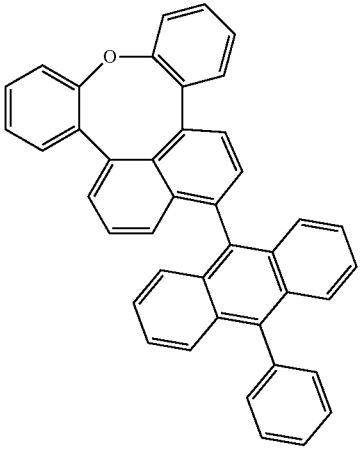
A-120
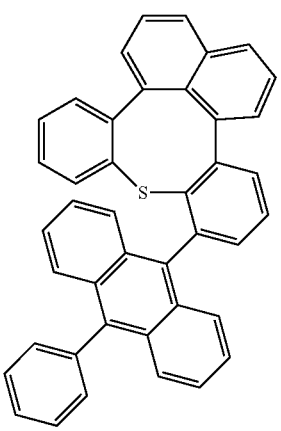
A-121

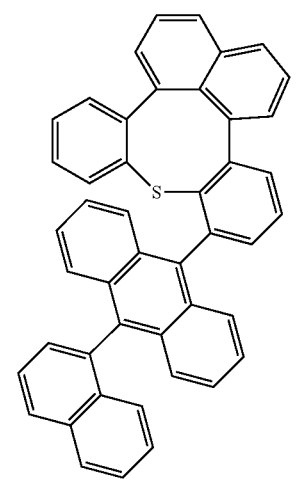
A-122
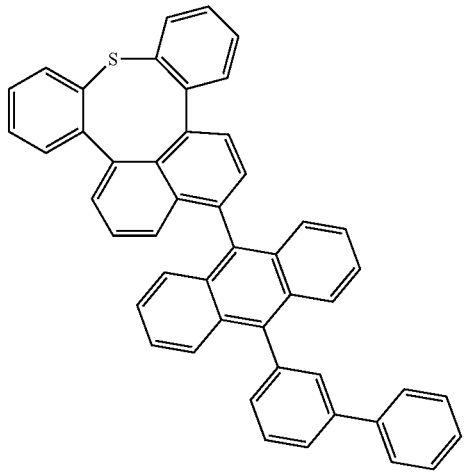
A-125
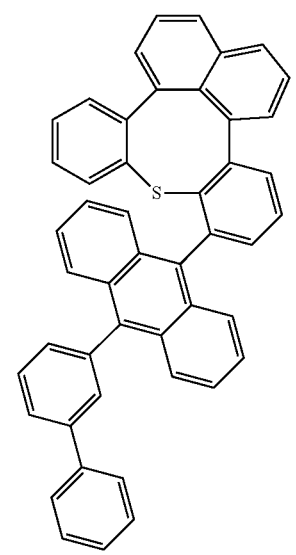
A-123
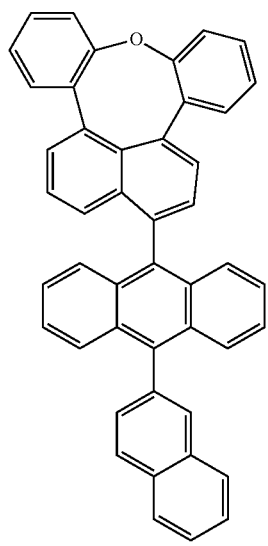
A-126
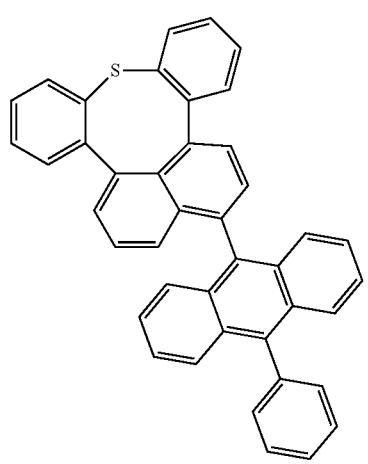
A-124
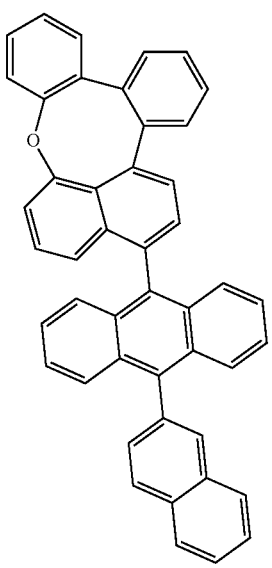
A-127

A-128
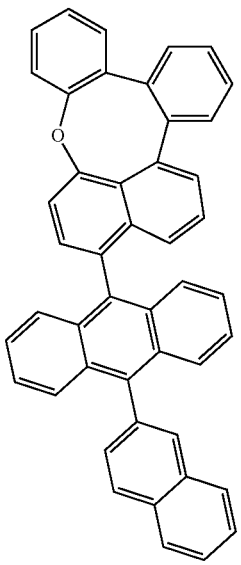
A-129
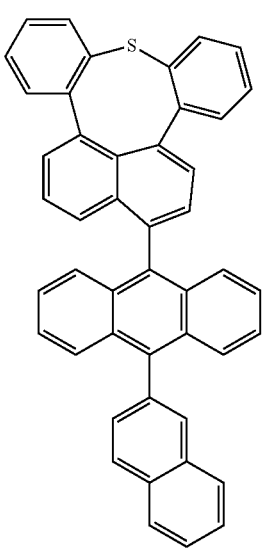
A-130
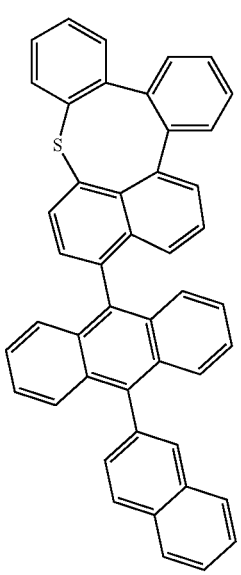
A-131
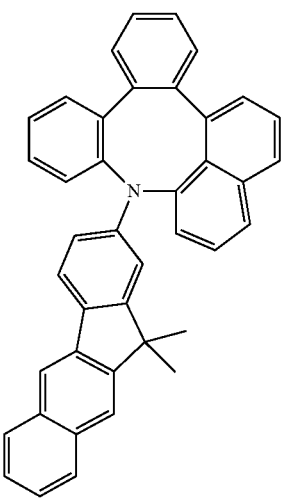
A-132
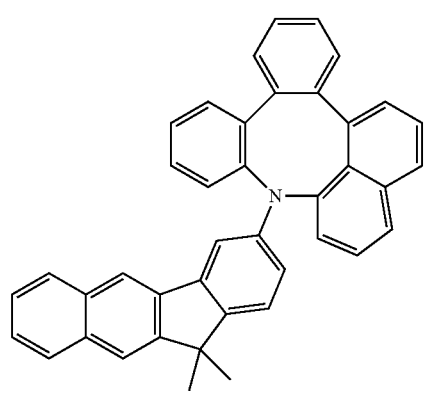
A-133
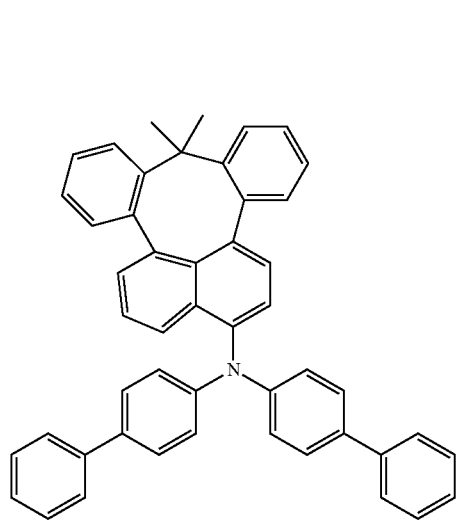

A-134
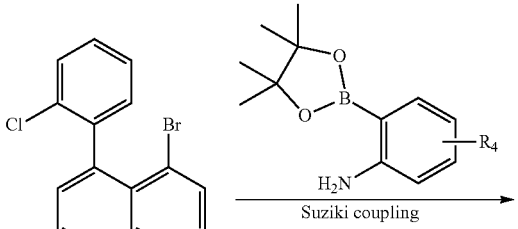
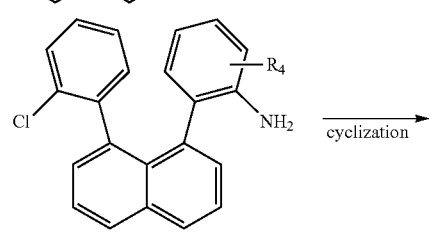
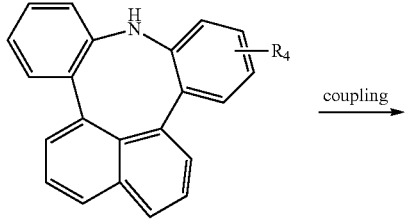
A-135
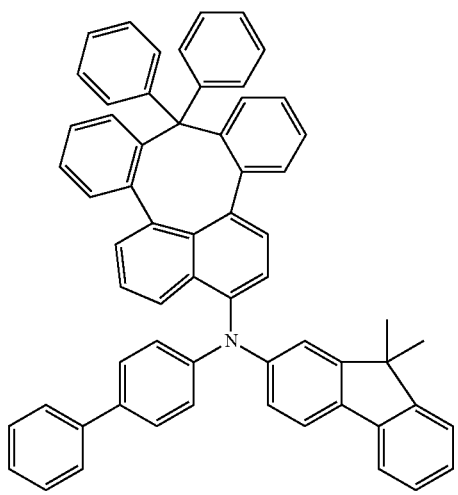
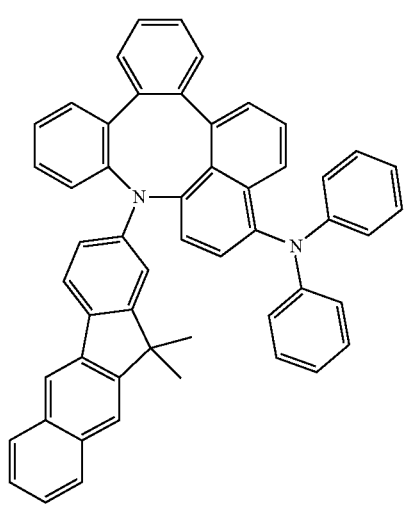
The compound of formula 1 according to the present disclosure can be prepared by a synthetic method known to a person skilled in the art. For example, it can be prepared according to the following reaction schemes, but is not limited thereto.
[Reaction Scheme 1]
[Reaction Scheme 2]
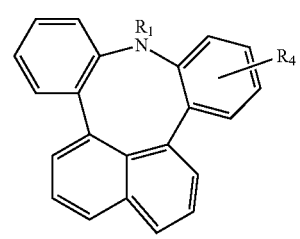
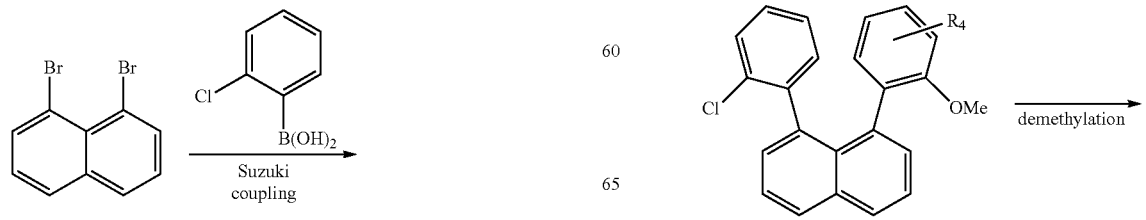

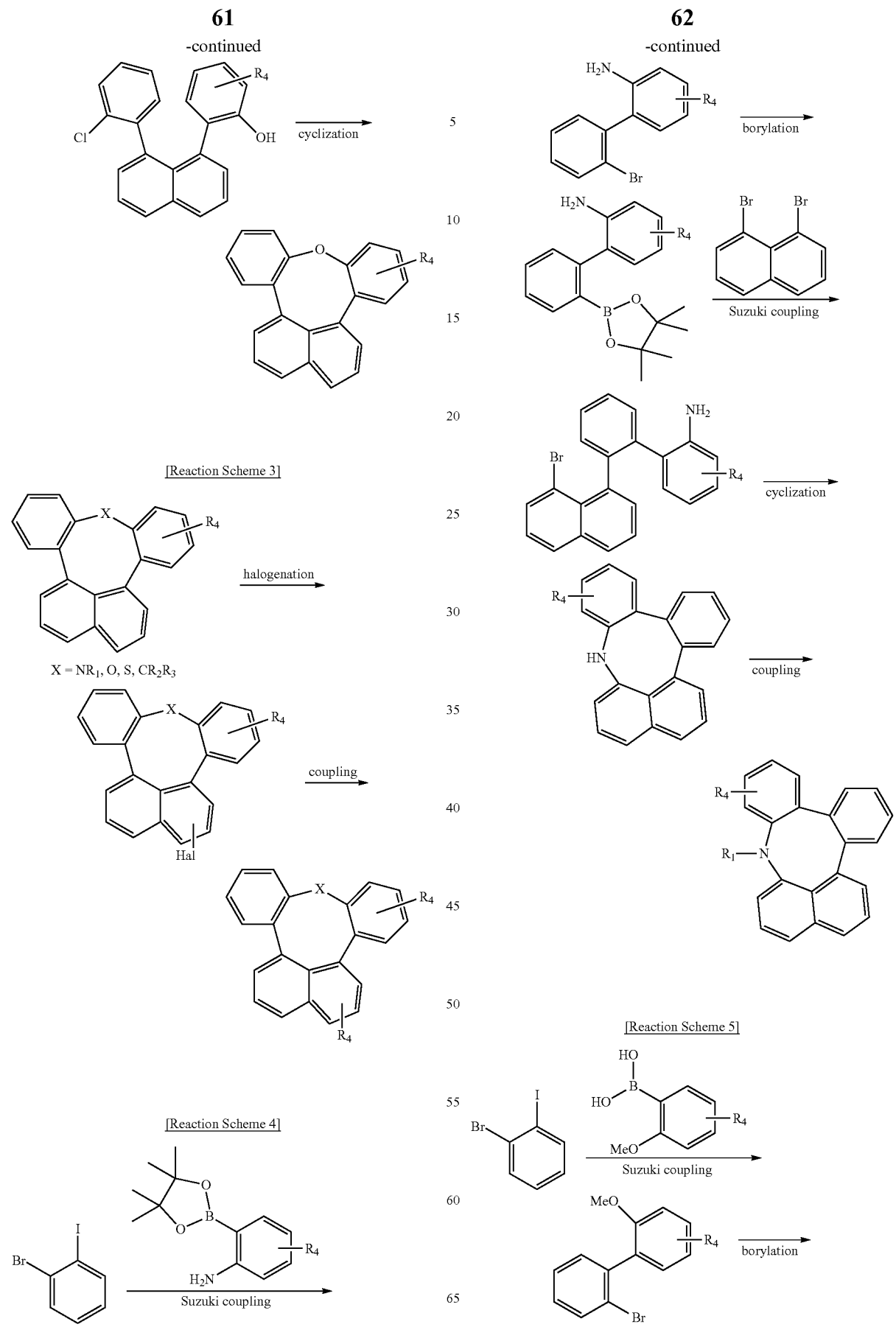

-continued

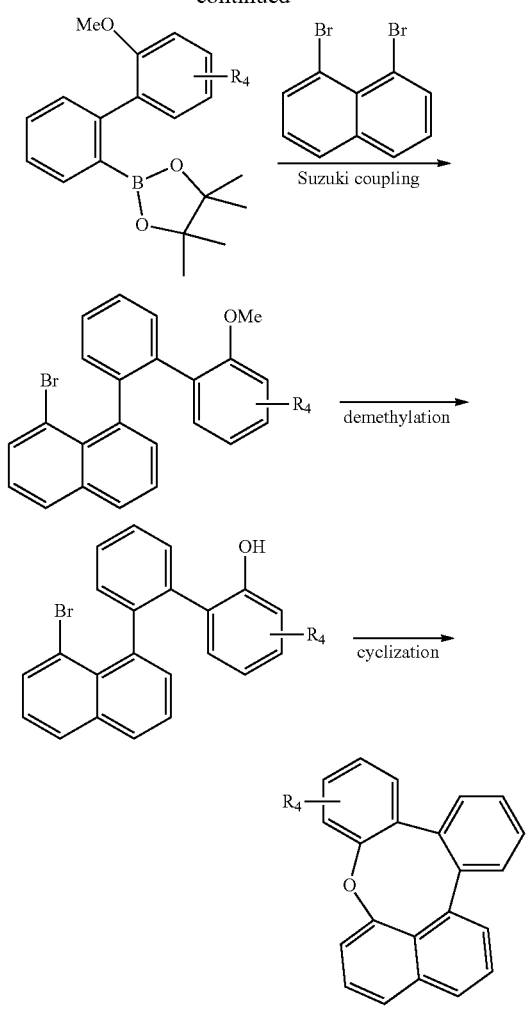

[Reaction Scheme 6]

X = NR₁, O, S, CR₂R₃

-continued wherein $R_1$ to $R_4$ are as defined in formula 1.

Although illustrative synthesis examples of the compound represented by formula 1 were described above, one skilled in the art will be able to readily understand that all of them are based on a Buchwald-Hartwig cross-coupling reaction, an N-arylation reaction, an H-mont-mediated etherification reaction, a Miyaura borylation reaction, a Suzuki cross-coupling reaction, an Intramolecular acid-induced cyclization reaction, a Pd(II)-catalyzed oxidative cyclization reaction, a Grignard reaction, a Heck reaction, a Cyclic Dehydration reaction, an $SN_1$ substitution reaction, an $SN_2$ substitution reaction, a Phosphine-mediated reductive cyclization reaction, etc., and the above reactions proceed even when substituents, which are defined in formula 1 above but are not specified in the specific synthesis examples, are bonded.

The hole transport zone of the present disclosure may be composed of one or more layers selected from the group consisting of a hole transport layer, a hole injection layer, an electron blocking layer, and a hole auxiliary layer. Each layer may consist of one or more layers.

According to one embodiment of the present disclosure, the hole transport zone comprises a hole transport layer. In addition, the hole transport zone may comprise a hole transport layer and further comprise one or more layers of a hole injection layer, an electron blocking layer, and a hole auxiliary layer.

In addition, the present disclosure provides an organic electroluminescent material comprising the organic electroluminescent compound of formula 1, and an organic electroluminescent device comprising the material.

The above material may be a hole transport material, a hole auxiliary material, or a light-emitting auxiliary material, specifically a hole transport material, a hole auxiliary material, or a light-emitting auxiliary material of an organic electroluminescent device emitting red light. When there are two or more hole transport layers, the material may be a hole transport material (hole auxiliary material) comprised in the hole transport layer adjacent to the light-emitting layer.

The above material may consist of the organic electroluminescent compound according to the present disclosure alone, or can further include conventional materials generally used in organic electroluminescent materials.

The organic electroluminescent device according to the present disclosure comprises a first electrode; a second electrode; and at least one organic layer between the first and second electrodes. The organic layer may comprise at least one organic electroluminescent compound of formula 1.

One of the first and second electrodes may be an anode, and the other may be a cathode. The organic layer may comprise a light-emitting layer, and may further comprise at least one layer selected from a hole injection layer, a hole transport layer, a hole auxiliary layer, a light-emitting auxiliary layer, an electron transport layer, an electron buffer layer, an electron injection layer, an interlayer, a hole blocking layer, and an electron blocking layer.

The first electrode and the second electrode may each be formed with a transmissive conductive material, a transflective conductive material, or a reflective conductive material. The organic electroluminescent device may be a top emission type, a bottom emission type, or both-sides emission type according to the kinds of the material forming the first electrode and the second electrode. In addition, the hole injection layer may be further doped with a p-dopant, and the electron injection layer may be further doped with an n-dopant.

According to one embodiment of the present disclosure, the organic electroluminescent device of the present disclosure may further comprise an azine-based compound as one or more of an electron transport material, an electron injection material, an electron buffer material, and a hole blocking material, besides the organic electroluminescent compound of the present disclosure.

The organic electroluminescent compound of formula 1 of the present disclosure may be comprised in at least one layer of the light-emitting layer, the hole injection layer, the hole transport layer, the hole auxiliary layer, the light-emitting auxiliary layer, the electron transport layer, the electron buffer layer, the electron injection layer, the interlayer, the hole blocking layer, and the electron blocking layer, preferably in at least one layer of the hole transport layer, the hole auxiliary layer, the light-emitting auxiliary layer, and the light-emitting layer. When there are two or more hole transport layers, the organic electroluminescent compound can be used in at least one of the layers. For example, when used in the hole transport layer, the organic electroluminescent compound of the present disclosure may be comprised as a hole transport material. In addition, when used in the light-emitting layer, the organic electroluminescent compound of the present disclosure may be comprised as a host material.

The light-emitting layer may comprise one or more hosts and one or more dopants. If necessary, the light-emitting layer may comprise a co-host material, i.e., a plurality of host materials of two or more. The organic electroluminescent compound of the present disclosure can be used as a co-host material.

The host used in the present disclosure may be a phosphorescent host compound or a fluorescent host compound, and the host compounds are not particularly limited.

The dopant comprised in the organic electroluminescent device according to the present disclosure may be at least one phosphorescent or fluorescent dopant, preferably at least one phosphorescent dopant. The phosphorescent dopant materials applied to the organic electroluminescent device according to the present disclosure are not particularly limited, but may be selected from metallated complex compounds of iridium (Ir), osmium (Os), copper (Cu), and platinum (Pt), may be preferably selected from ortho-metallated complex compounds of iridium (Ir), osmium (Os), copper (Cu), and platinum (Pt), and may be more preferably an ortho-metallated iridium complex compound.

The dopant comprised in the organic electroluminescent device of the present disclosure may include the compound represented by the following formula 101, but is not limited thereto.

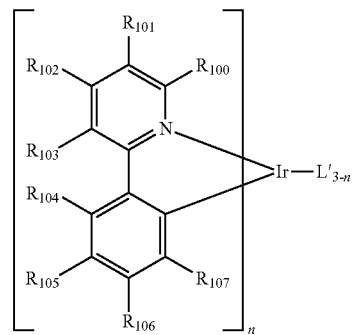

(101)

In formula 101, L is selected from the following structures 1 and 2:

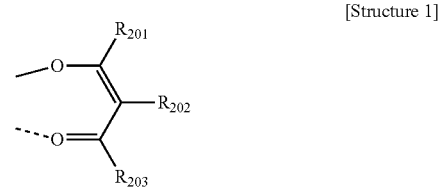

[Structure 1]

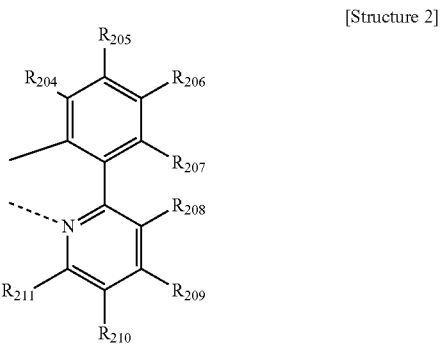

[Structure 2]

$R_{100}$ to $R_{103}$, each independently, represent hydrogen, deuterium, a halogen, a (C1-C30)alkyl unsubstituted or substituted with a halogen(s), a substituted or unsubstituted (C3-C30)cycloalkyl, a substituted or unsubstituted (C6-C30)aryl, a cyano, a substituted or unsubstituted (3- to 30-membered)heteroaryl, or a substituted or unsubstituted (C1-C30)alkoxy; or may be linked to an adjacent substituent to form a ring(s), e.g., a substituted or unsubstituted, quinoline, isoquinoline, benzofuropyridine, benzothienopyridine, indenopyridine, benzofuroquinoline, benzothienoquinoline, or indenoquinoline ring, together with pyridine;

$R_{104}$ to $R_{107}$, each independently, represent hydrogen, deuterium, a halogen, a (C1-C30)alkyl unsubstituted or substituted with a halogen(s), a substituted or unsubstituted (C3-C30)cycloalkyl, a substituted or unsubstituted (C6-C30)aryl, a substituted or unsubstituted (3- to 30-membered)heteroaryl, a cyano, or a substituted or unsubstituted (C1-C30)alkoxy; or may be linked to an adjacent substituent to form a ring(s), e.g., a substituted or unsubstituted, naphthalene, fluorene, dibenzothiophene, dibenzofuran, indenopyridine, benzofuropyridine, or benzothienopyridine ring, together with benzene;

$R_{201}$ to $R_{211}$, each independently, represent hydrogen, deuterium, a halogen, a (C1-C30)alkyl unsubstituted or substituted with a halogen(s), a substituted or unsubstituted (C3-C30)cycloalkyl, or a substituted or unsubstituted (C6-C30)aryl; or may be linked to an adjacent substituent to form a ring; and
n represents an integer of 1 to 3.
The specific examples of the dopant compound are as follows, but are not limited thereto.
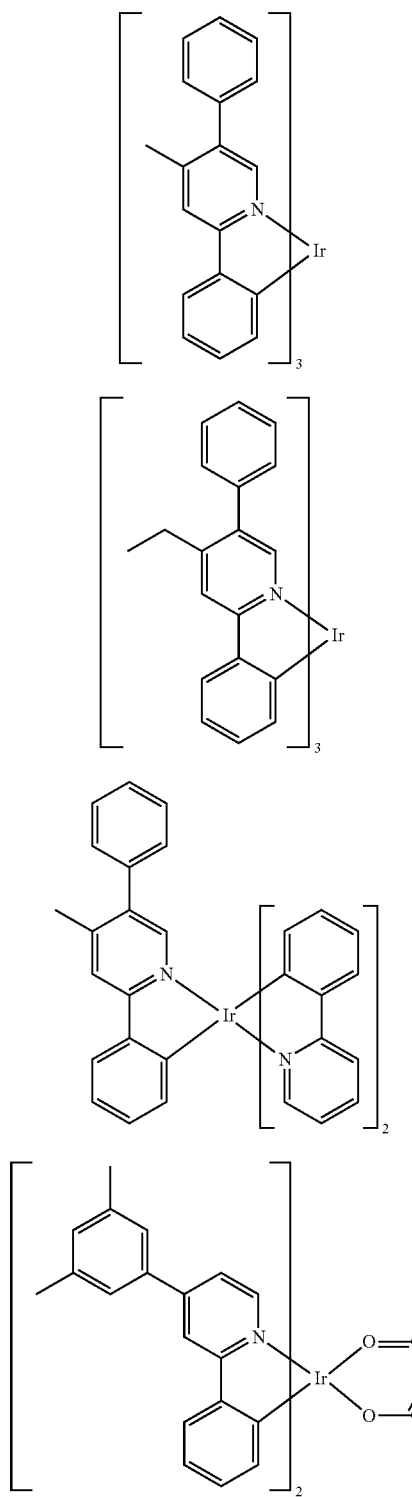
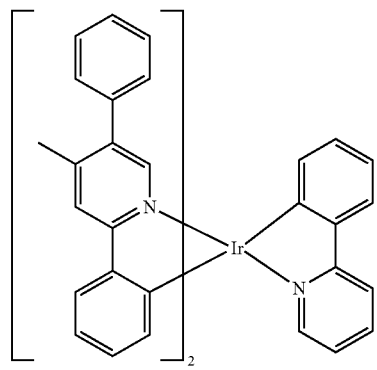
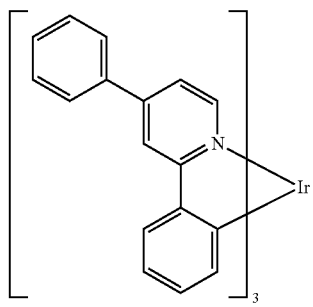
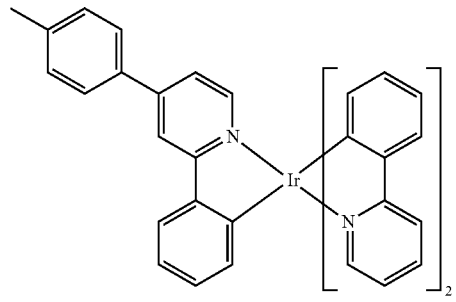
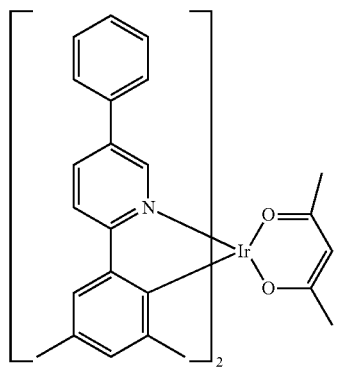

D-9
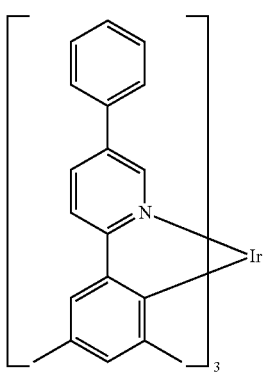
D-10
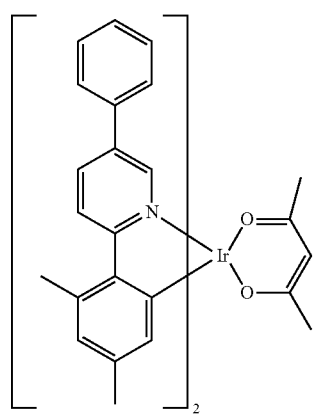
D-11
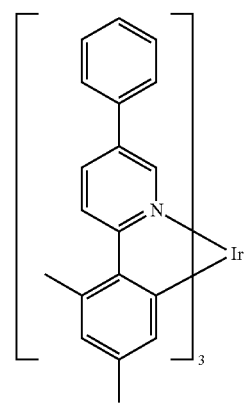
D-12
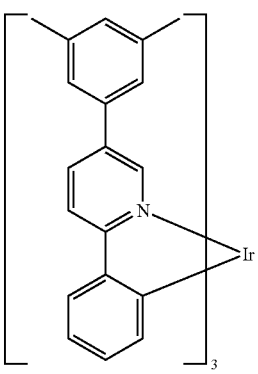
D-13
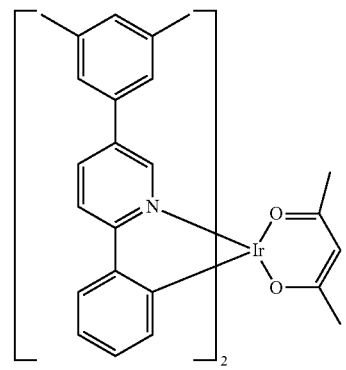
D-14
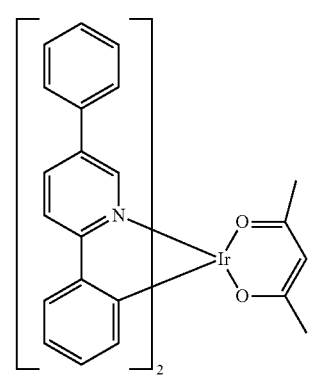
D-15
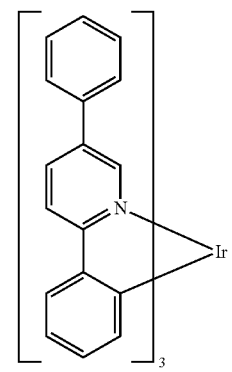
D-16
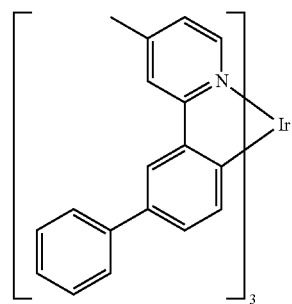

-continued
D-17
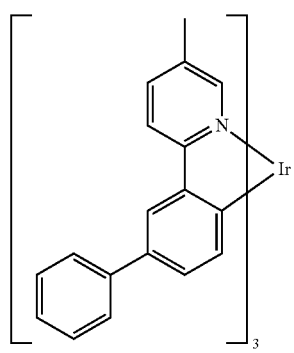
D-18
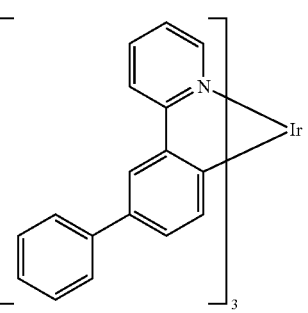
D-19
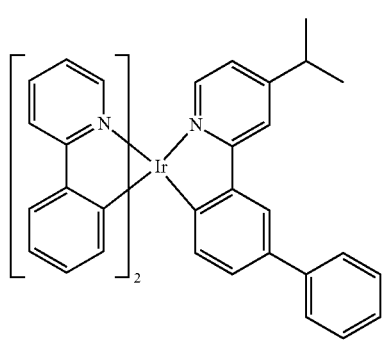
D-20
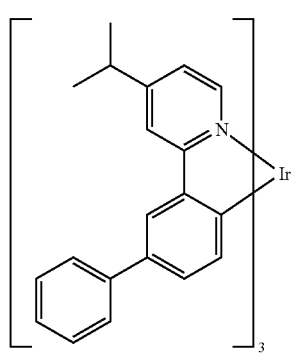
-continued
D-21
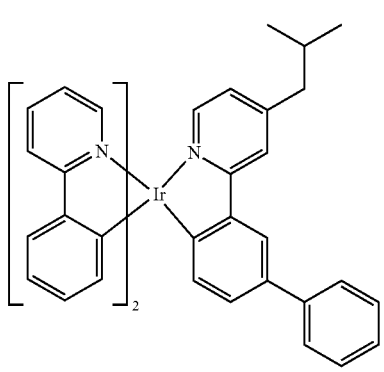
D-22
D-23
D-24
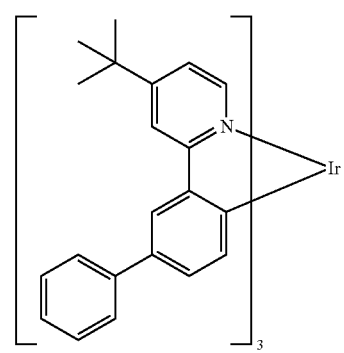

D-25 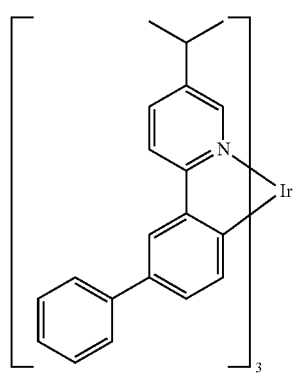
D-26 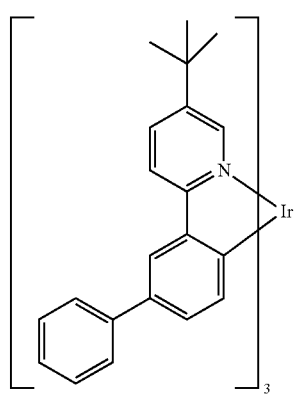
D-27 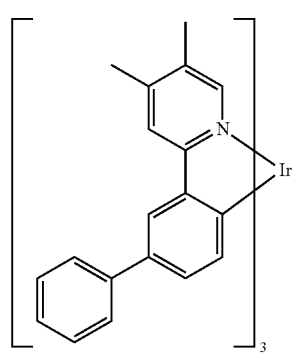
D-28 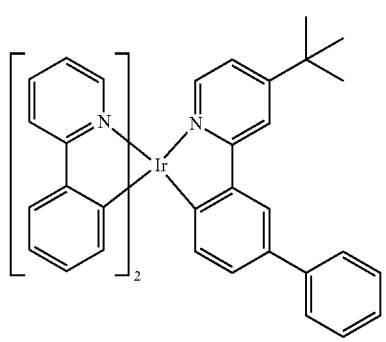
D-29 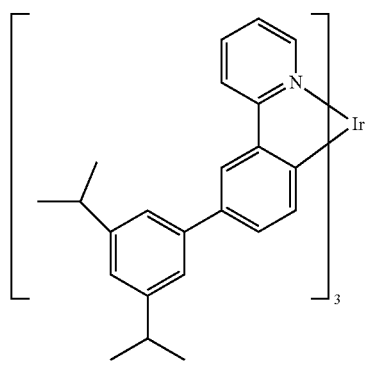
D-30 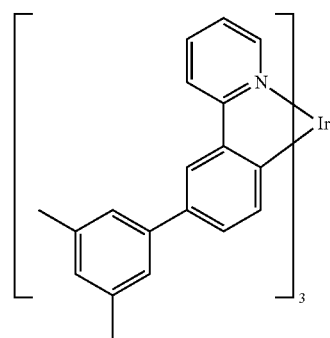
D-31 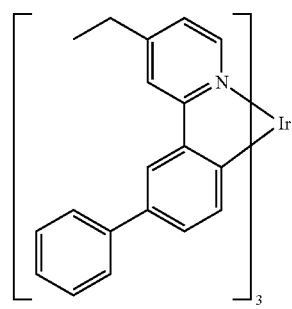
D-32 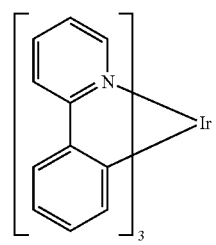
D-33 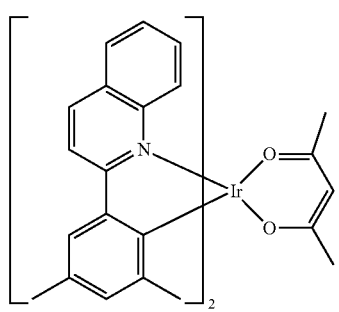

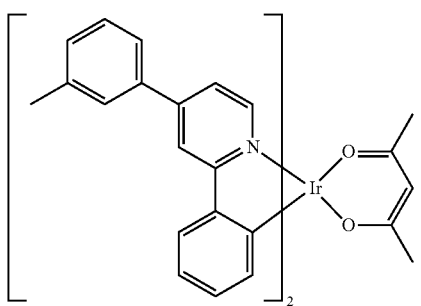
D-34
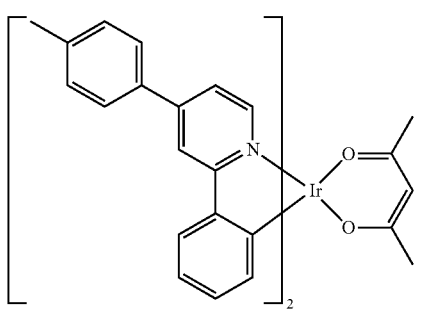
D-35
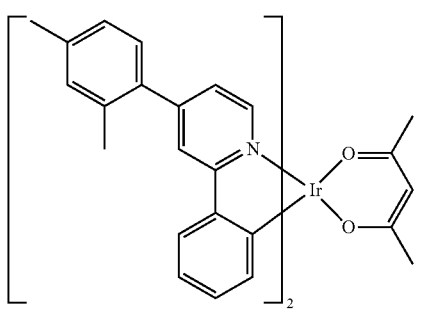
D-36
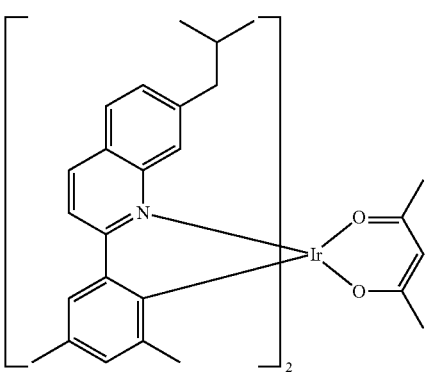
D-37
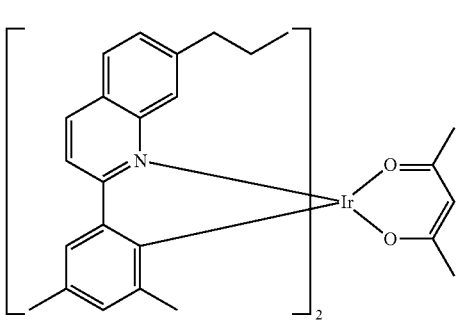
D-38
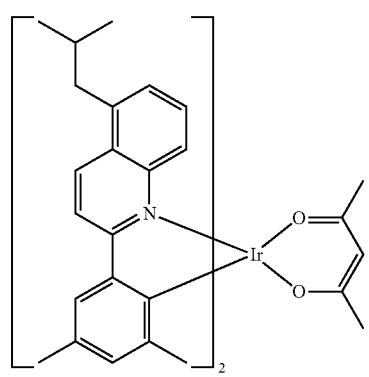
D-39
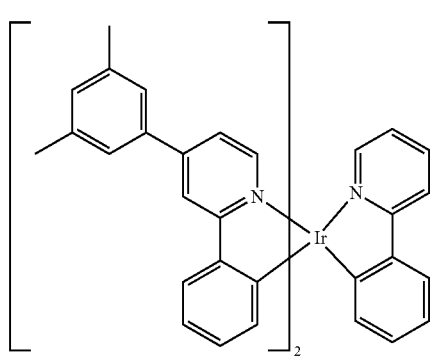
D-40
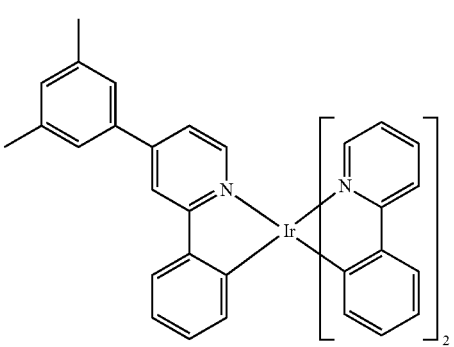
D-41
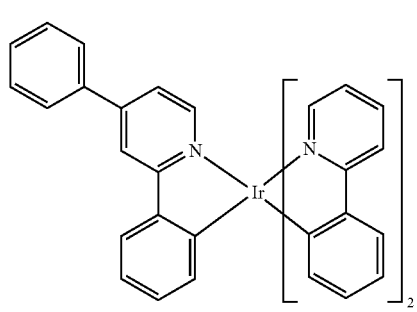
D-42

D-43 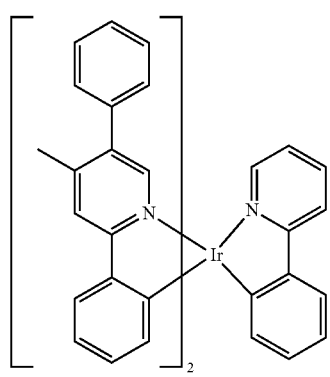
D-44 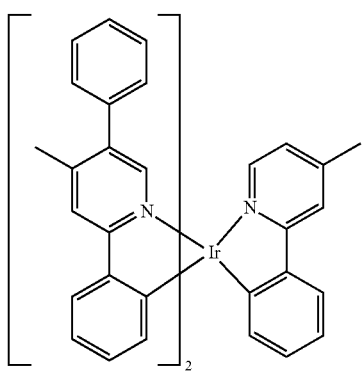
D-45 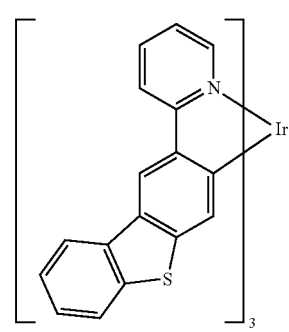
D-46 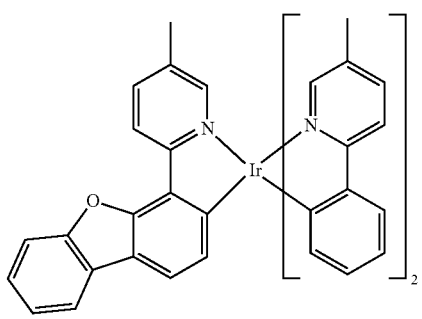
D-47 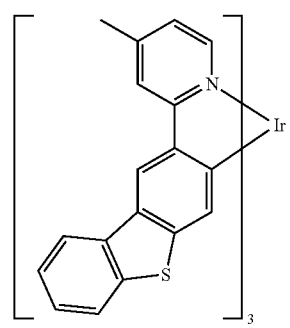
D-48 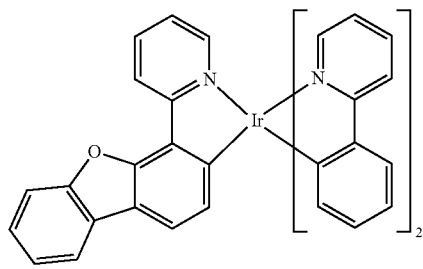
D-49 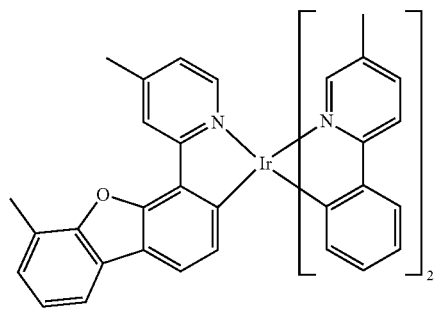
D-50 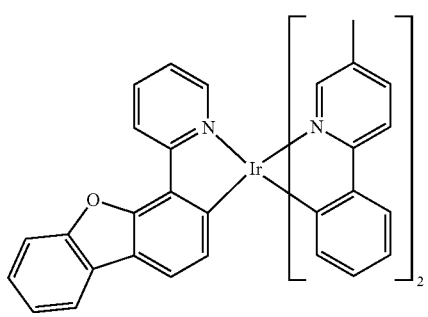
D-51 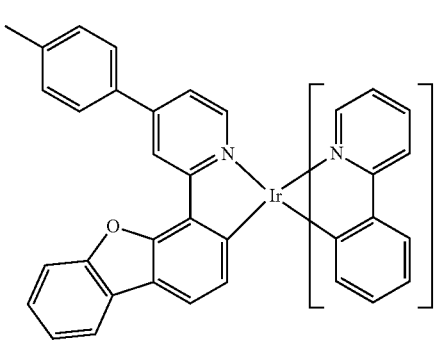

-continued
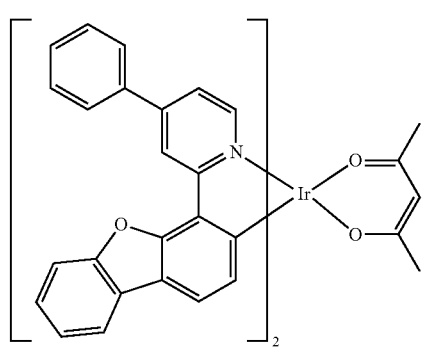
D-52
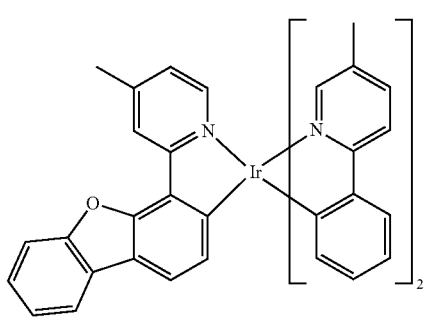
D-53
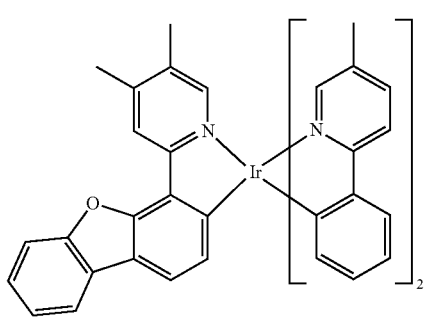
D-54
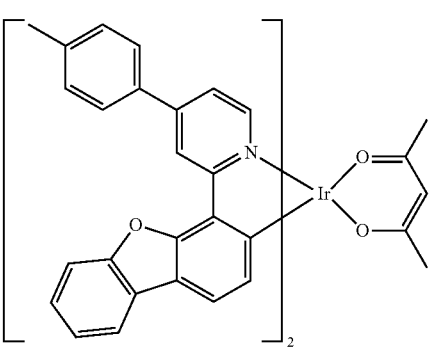
D-55
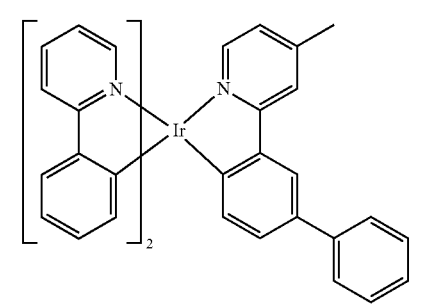
D-56
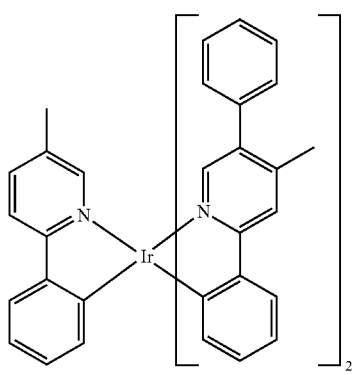
D-57
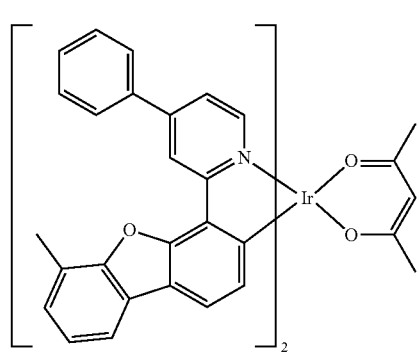
D-58
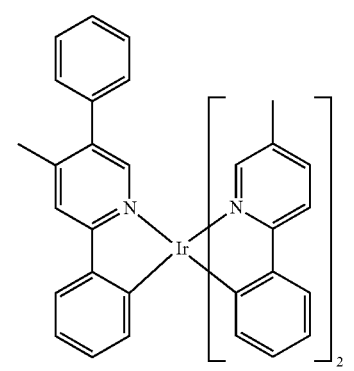
D-59
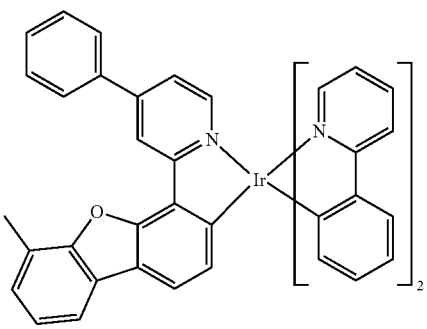
D-60

-continued
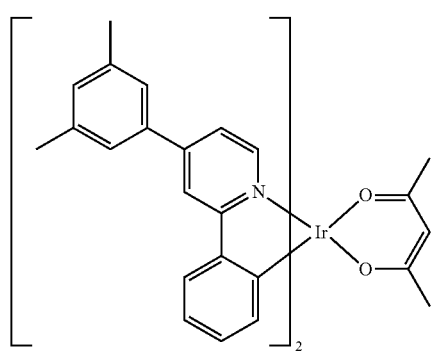
D-61
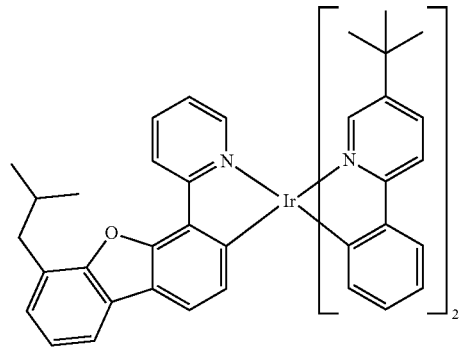
D-65
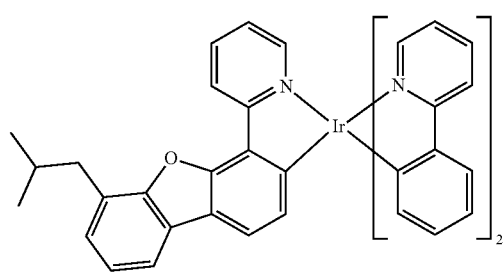
D-62
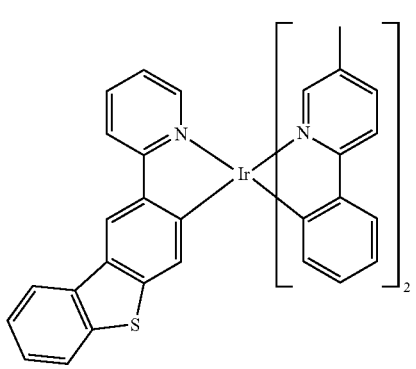
D-66
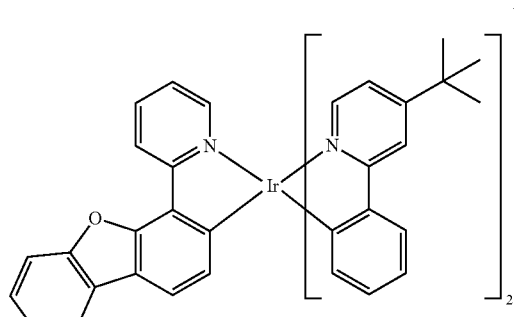
D-63
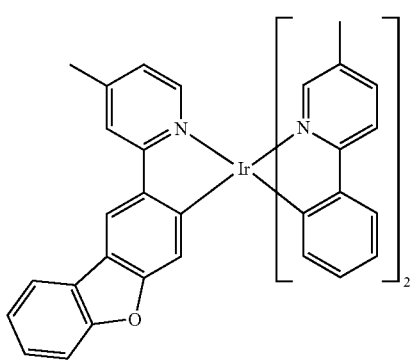
D-67
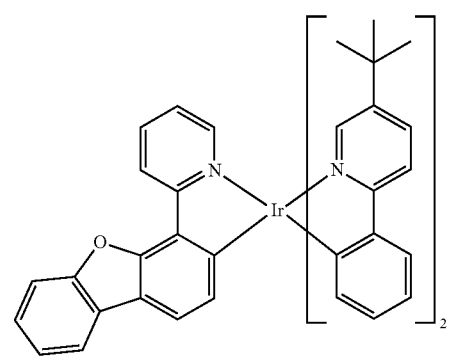
D-64
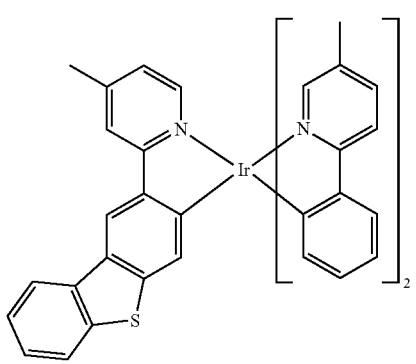
D-68

-continued
D-69
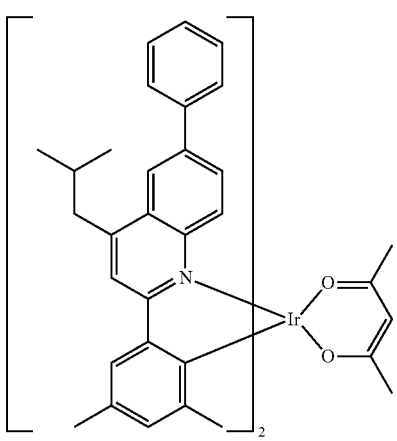
D-70
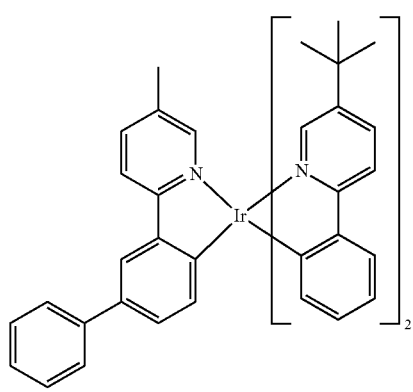
D-71
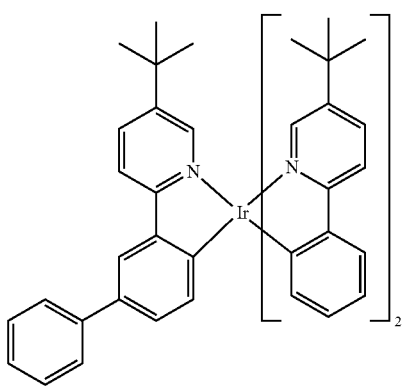
D-72
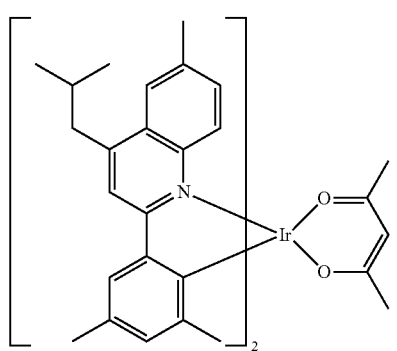
-continued
D-73
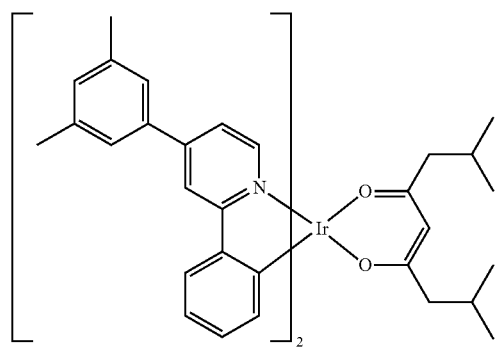
D-74
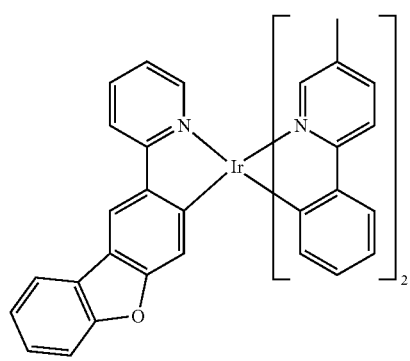
D-75
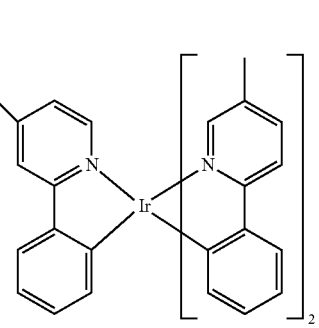
D-76
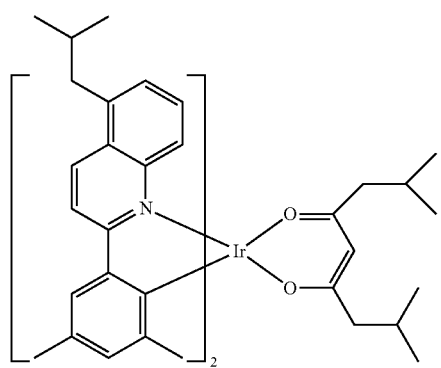

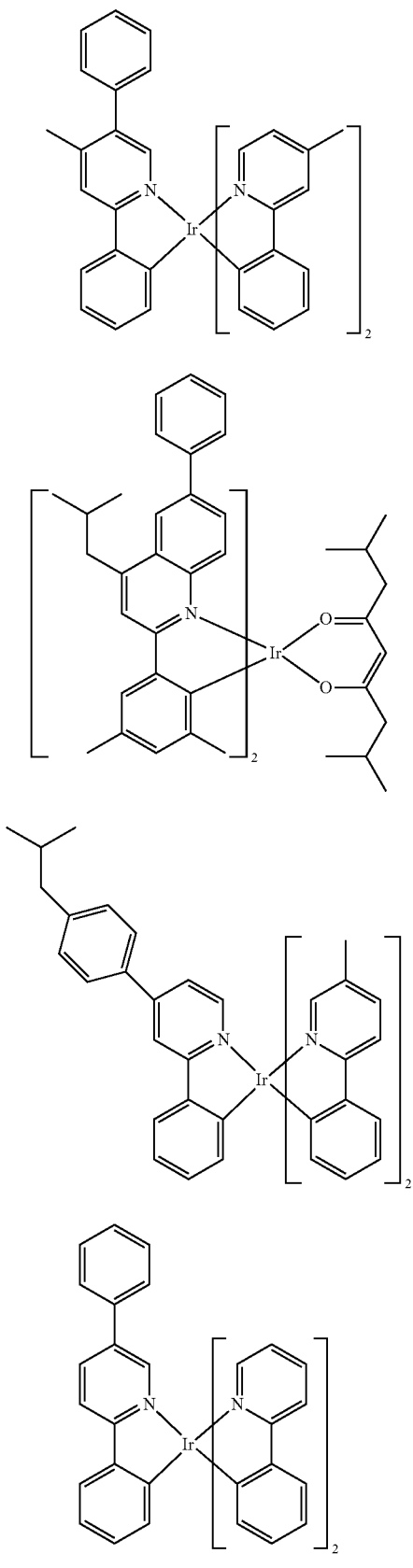
D-77
D-78
D-79
D-80
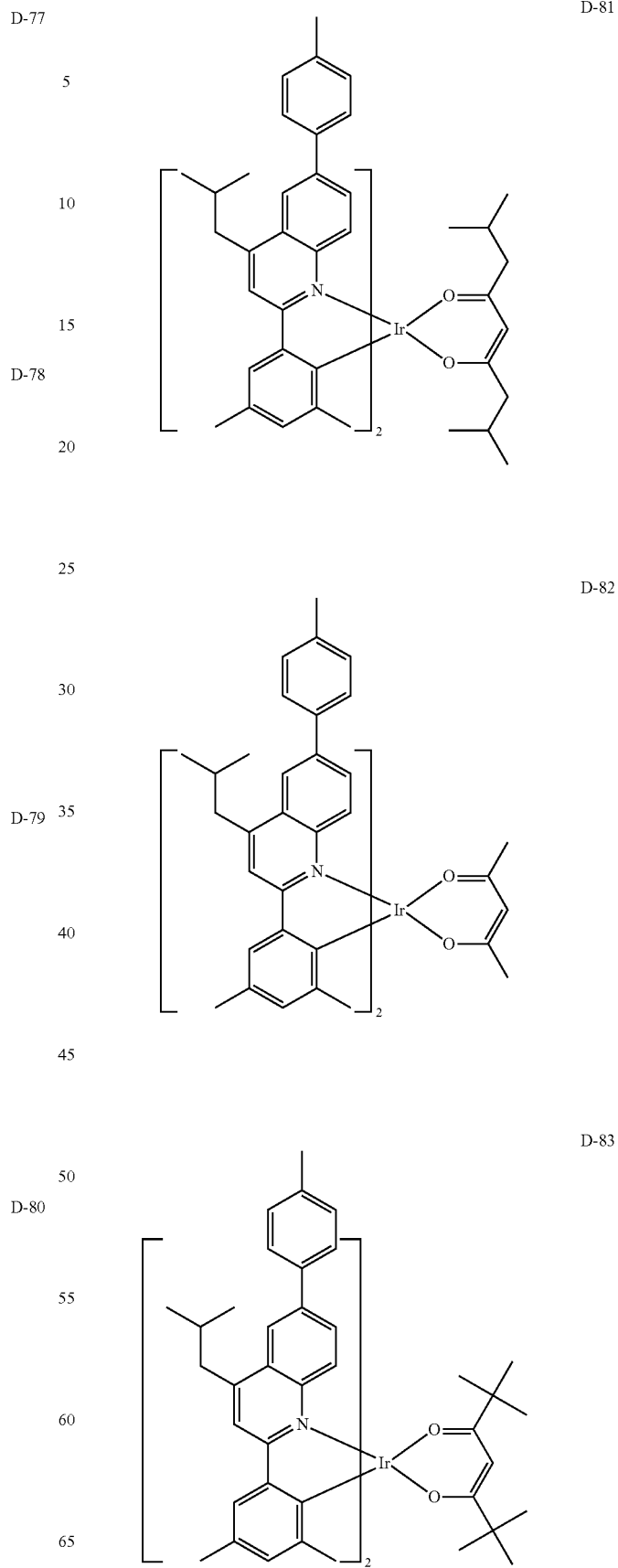
D-81
D-82
D-83

D-84
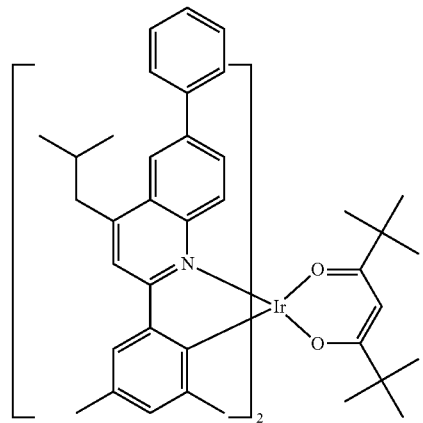
D-85
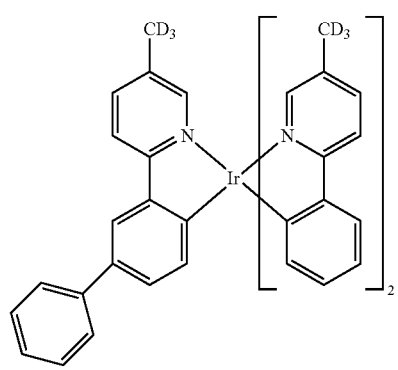
D-86
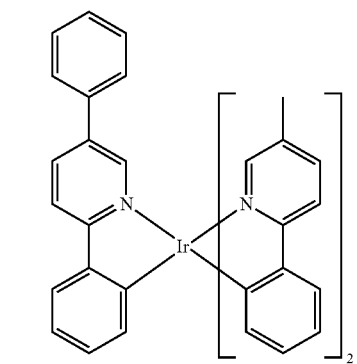
D-87
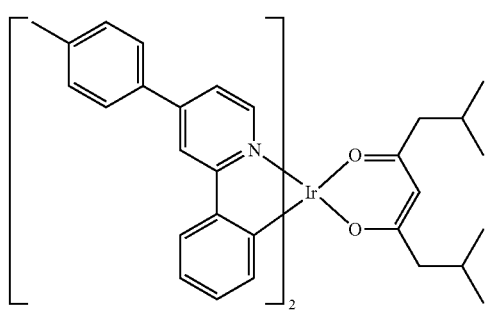
D-88
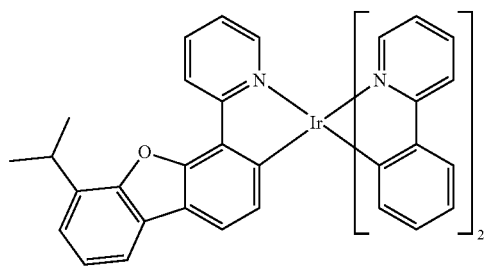
D-89
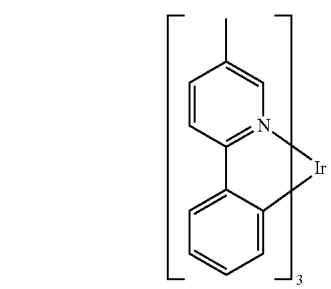
D-90
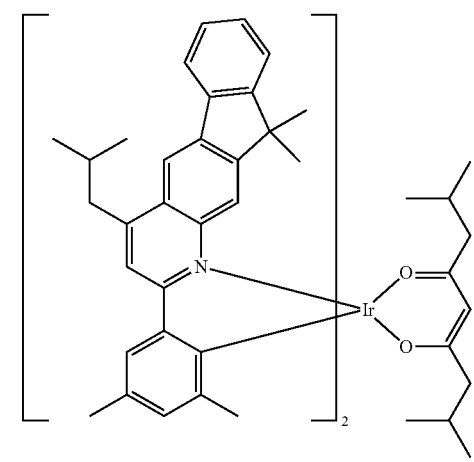
D-91
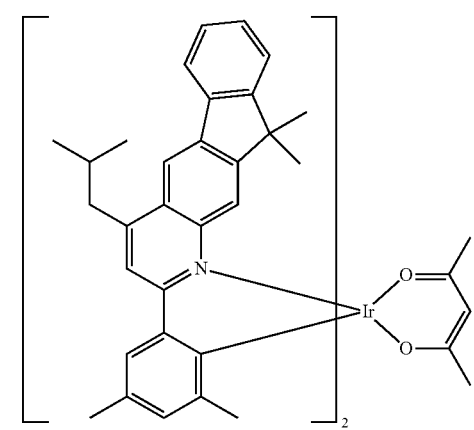

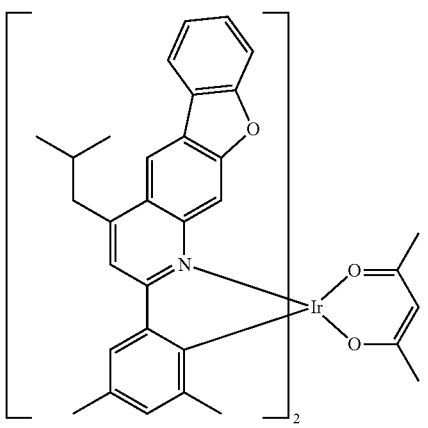
D-92
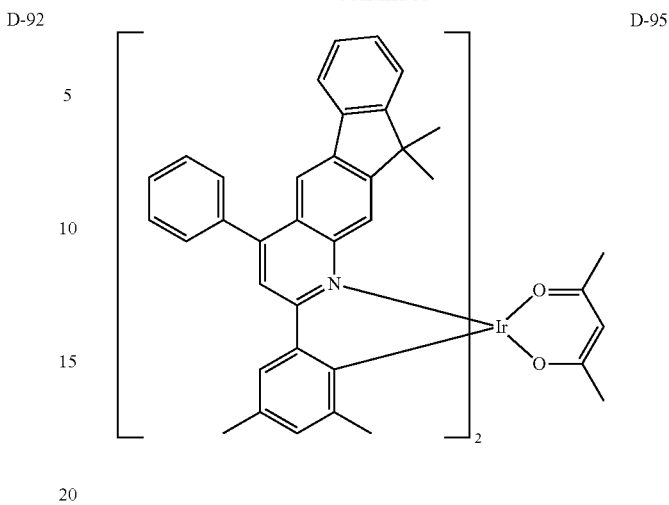
D-95
D-96
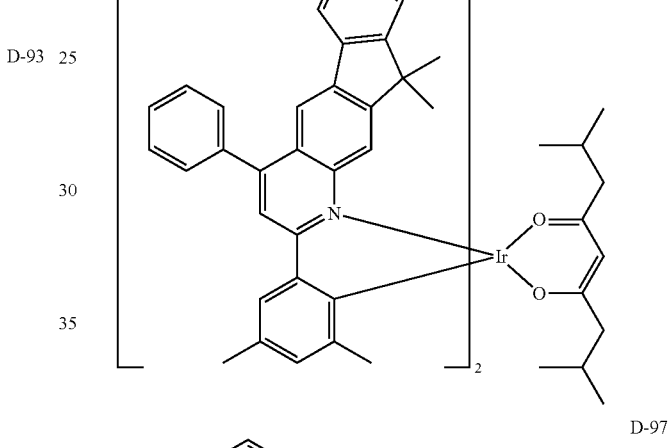
D-93
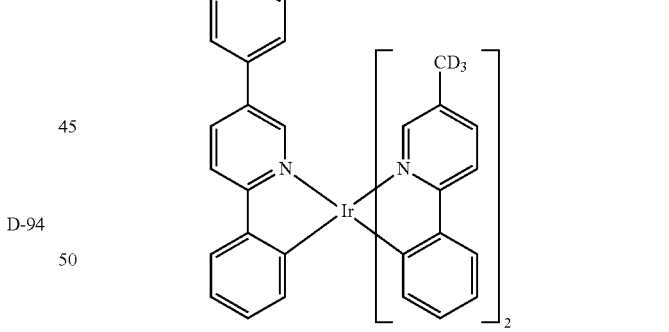
D-97
D-94
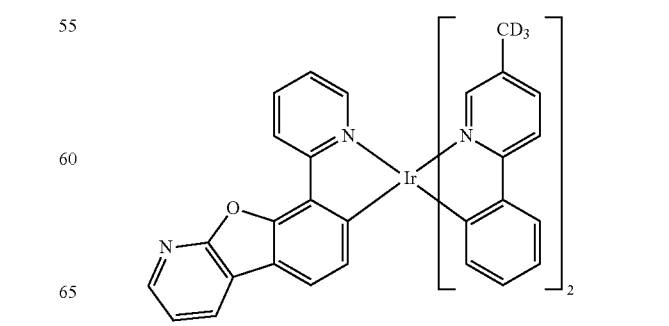
D-98

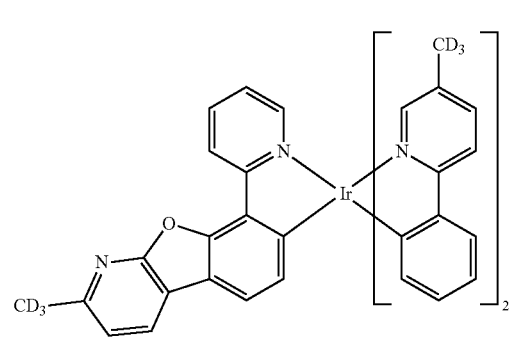
D-99
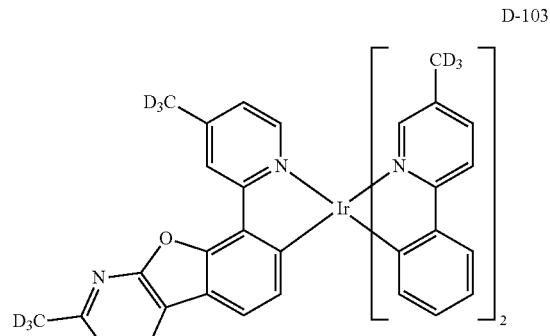
D-103
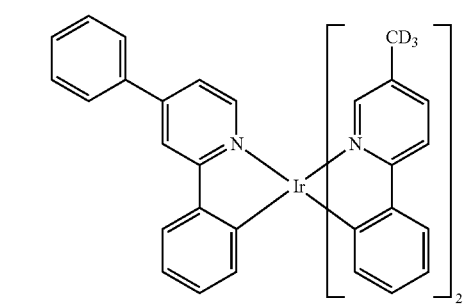
D-100
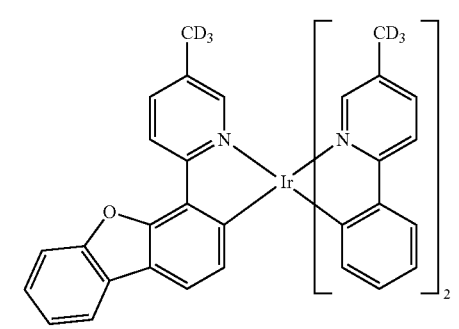
D-104
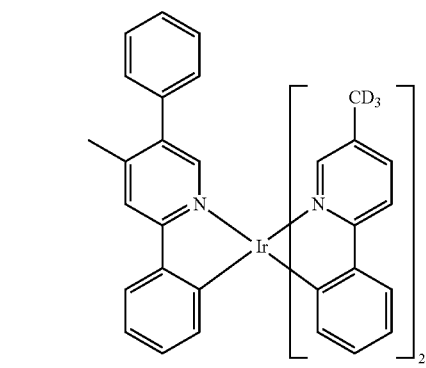
D-101
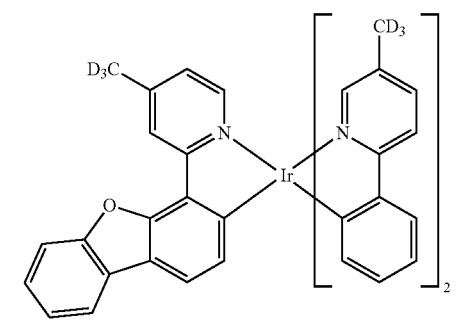
D-105
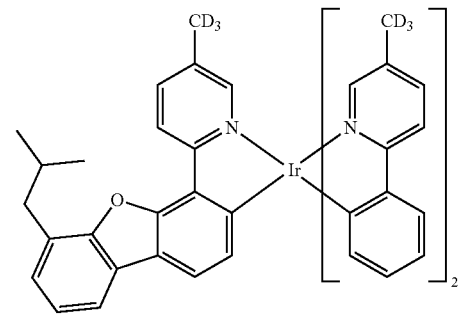
D-106
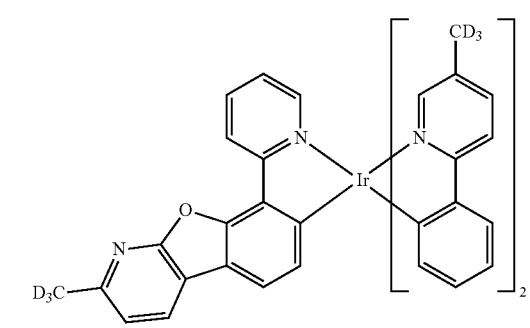
D-102
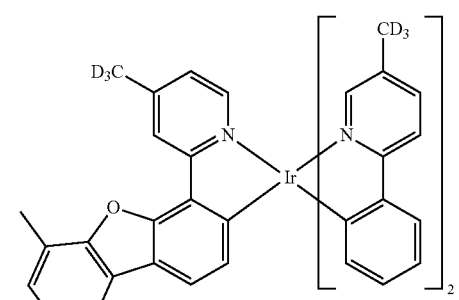
D-107

-continued
D-108
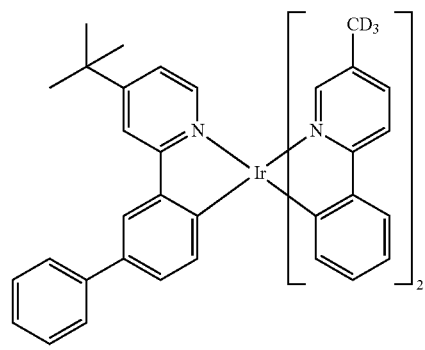
D-109
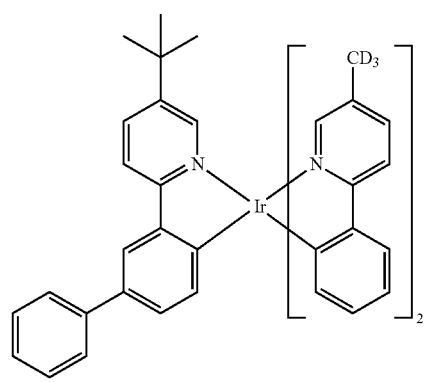
D-110
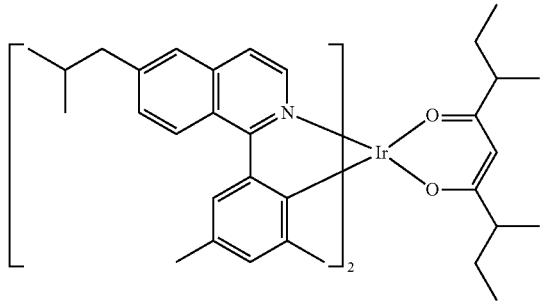
D-111
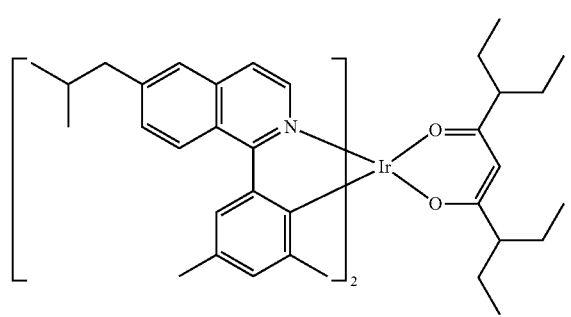
-continued
D-112
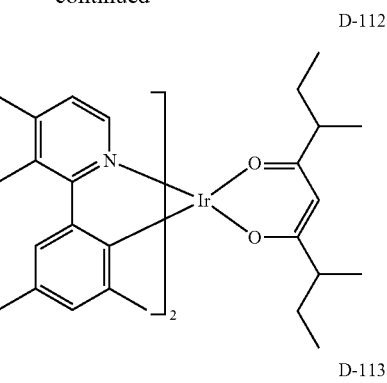
D-113
D-114
D-115
D-116
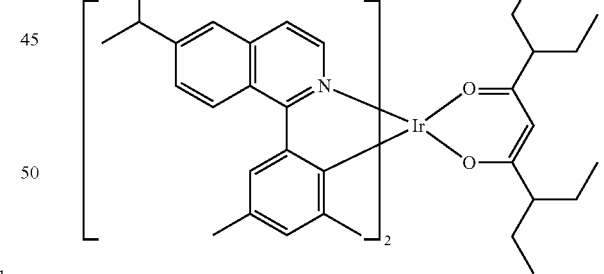

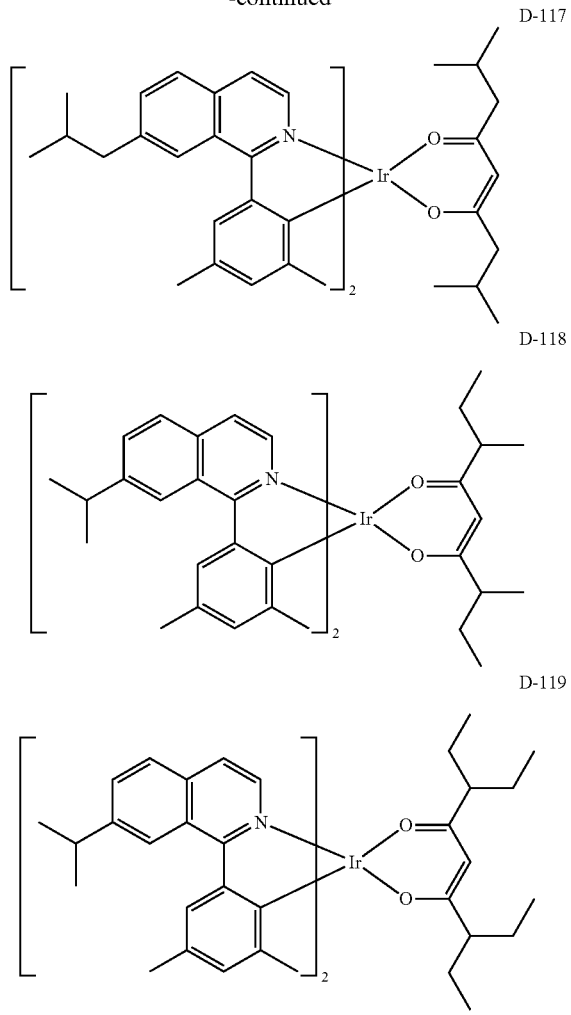

D-117

D-118

D-119

In another embodiment of the present disclosure, a composition for preparing an organic electroluminescent device is provided. The composition is preferably for preparing a hole transport layer, a hole auxiliary layer, or a light-emitting auxiliary layer of an organic electroluminescent device and comprises the compound of the present disclosure. When there are two or more hole transport layers, the compound of the present disclosure may be comprised in the composition for preparing a hole transport layer (hole auxiliary layer) adjacent to the light-emitting layer.

In addition, the organic electroluminescent device according to the present disclosure comprises a first electrode; a second electrode; and at least one organic layer between the first and second electrodes. The organic layer comprises a hole transport layer, a hole auxiliary layer, or a light-emitting auxiliary layer, and the hole transport layer, the hole auxiliary layer, or the light-emitting auxiliary layer may comprise the composition for preparing the organic electroluminescent device according to the present disclosure.

The organic electroluminescent device according to the present disclosure may further comprise, in addition to the organic electroluminescent compound represented by formula 1, at least one compound selected from the group consisting of arylamine-based compounds and styrylarylamine-based compounds.

In the organic electroluminescent device of the present disclosure, the organic layer may further comprise, besides the organic electroluminescent compound of formula 1, at least one metal selected from the group consisting of metals of Group 1, metals of Group 2, transition metals of the $4^{th}$ period, transition metals of the $5^{th}$ period, lanthanides, and organic metals of the d-transition elements of the Periodic Table, or at least one complex compound comprising the metal.

In addition, the organic electroluminescent device of the present disclosure may emit white light by further comprising at least one light-emitting layer, which comprises a blue, a red, or a green electroluminescent compound known in the field, besides the compound of the present disclosure. If necessary, it may further comprise a yellow or an orange light-emitting layer.

In the organic electroluminescent device of the present disclosure, preferably, at least one layer selected from a chalcogenide layer, a metal halide layer, and a metal oxide layer (hereinafter, "a surface layer") may be placed on an inner surface(s) of one or both electrode(s). Specifically, a chalcogenide (including oxides) layer of silicon or aluminum is preferably placed on an anode surface of an electroluminescent medium layer, and a metal halide layer or a metal oxide layer is preferably placed on a cathode surface of an electroluminescent medium layer. Such a surface layer provides operation stability for the organic electroluminescent device. Preferably, the chalcogenide includes $SiO_X$ ($1 \leq X \leq 2$), $AlO_X$ ($1 \leq X \leq 1.5$), SiON, SiAlON, etc.; the metal halide includes LiF, $MgF_2$, $CaF_2$, a rare earth metal fluoride, etc.; and the metal oxide includes $Cs_2O$, $Li_2O$, MgO, SrO, BaO, CaO, etc.

A hole injection layer, a hole transport layer, an electron blocking layer, or a combination thereof can be used between the anode and the light-emitting layer. The hole injection layer may be multi-layers in order to lower the hole injection barrier (or hole injection voltage) from the anode to the hole transport layer or the electron blocking layer, wherein each of the multi-layers may use two compounds simultaneously. The hole transport layer or the electron blocking layer may also be multi-layers.

An electron buffer layer, a hole blocking layer, an electron transport layer, an electron injection layer, or a combination thereof can be used between the light-emitting layer and the cathode. The electron buffer layer may be multi-layers in order to control the injection of the electron and improve the interfacial properties between the light-emitting layer and the electron injection layer, wherein each of the multi-layers may use two compounds simultaneously. The hole blocking layer or the electron transport layer may also be multi-layers, wherein each of the multi-layers may use a plurality of compounds.

Herein, the hole auxiliary layer or the light-emitting auxiliary layer is placed between the hole transport layer and the light-emitting layer, and may be used for controlling the hole transport speed. The hole auxiliary layer or the light-emitting auxiliary layer may provide an effect of improving the efficiency and lifespan of the organic electroluminescent device.

The light-emitting auxiliary layer may be placed between the anode and the light-emitting layer, or between the cathode and the light-emitting layer. When the light-emitting auxiliary layer is placed between the anode and the light-emitting layer, it can be used for promoting the hole injection and/or hole transport, or for preventing the overflow of electrons. When the light-emitting auxiliary layer is placed between the cathode and the light-emitting layer, it can be used for promoting the electron injection and/or electron transport, or for preventing the overflow of holes. Also, the hole auxiliary layer may be placed between the hole transport layer (or hole injection layer) and the light-emitting layer, and may be effective to promote or block the hole transport rate (or hole injection rate), thereby enabling the charge balance to be controlled. Further, the electron blocking layer may be placed between the hole transport layer (or hole injection layer) and the light-emitting layer, and can confine the excitons within the light-emitting layer by blocking the overflow of electrons from the light-emitting layer to prevent a light-emitting leakage. When an organic electroluminescent device includes two or more hole transport layers, the hole transport layer, which is further included, may be used as a hole auxiliary layer or an electron blocking layer. The hole auxiliary layer and the electron blocking layer may have an effect of improving the efficiency and/or the lifespan of the organic electroluminescent device.

Preferably, in the organic electroluminescent device of the present disclosure, a mixed region of an electron transport compound and a reductive dopant, or a mixed region of a hole transport compound and an oxidative dopant may be placed on at least one surface of a pair of electrodes. In this case, the electron transport compound is reduced to an anion, and thus it becomes easier to inject and transport electrons from the mixed region to the light-emitting medium. Furthermore, the hole transport compound is oxidized to a cation, and thus it becomes easier to inject and transport holes from the mixed region to the light-emitting medium. Preferably, the oxidative dopant includes various Lewis acids and acceptor compounds; and the reductive dopant includes alkali metals, alkali metal compounds, alkaline earth metals, rare-earth metals, and mixtures thereof. The reductive dopant layer may be employed as a charge-generating layer to prepare an organic EL device having two or more light-emitting layers and emitting white light.

An organic electroluminescent material according to one embodiment of the present disclosure may be used as light-emitting materials for a white organic light-emitting device. The white organic light-emitting device has been suggested to have various structures such as a parallel side-by-side arrangement method, a stacking arrangement method, or CCM (color conversion material) method, etc., according to the arrangement of R (Red), G (Green) or YG (yellowish green), an B (blue) light-emitting units. In addition, the organic electroluminescent material according to one embodiment of the present disclosure may also be applied to the organic electroluminescent device comprising a QD (quantum dot).

In order to form each layer constituting the organic EL device of the present disclosure, dry film-forming methods such as vacuum deposition, sputtering, plasma, ion plating methods, etc., or wet film-forming methods such as ink jet printing, spin coating, dip coating, flow coating methods, etc., can be used.

When using a wet film-forming method, a thin film is formed by dissolving or dispersing the material constituting each layer in suitable solvents, such as ethanol, chloroform, tetrahydrofuran, dioxane, etc. The solvents are not specifically limited as long as the material constituting each layer is soluble or dispersible in the solvents, which do not cause any problems in forming a layer.

By using the organic electroluminescent device of the present disclosure, a display system, for example, for smartphones, tablets, notebooks, PCs, TVs, or vehicles, or a lighting system, for example, an indoor or outdoor lighting system, can be produced.

Hereinafter, the preparation method of the organic electroluminescent compounds of the present disclosure, the physical properties of the compounds, and the luminous properties of the organic electroluminescent device comprising the compounds will be explained in detail with reference to the representative compounds of the present disclosure. However, the present disclosure is not limited by the following examples.

Example 1: Preparation of Compound A-1

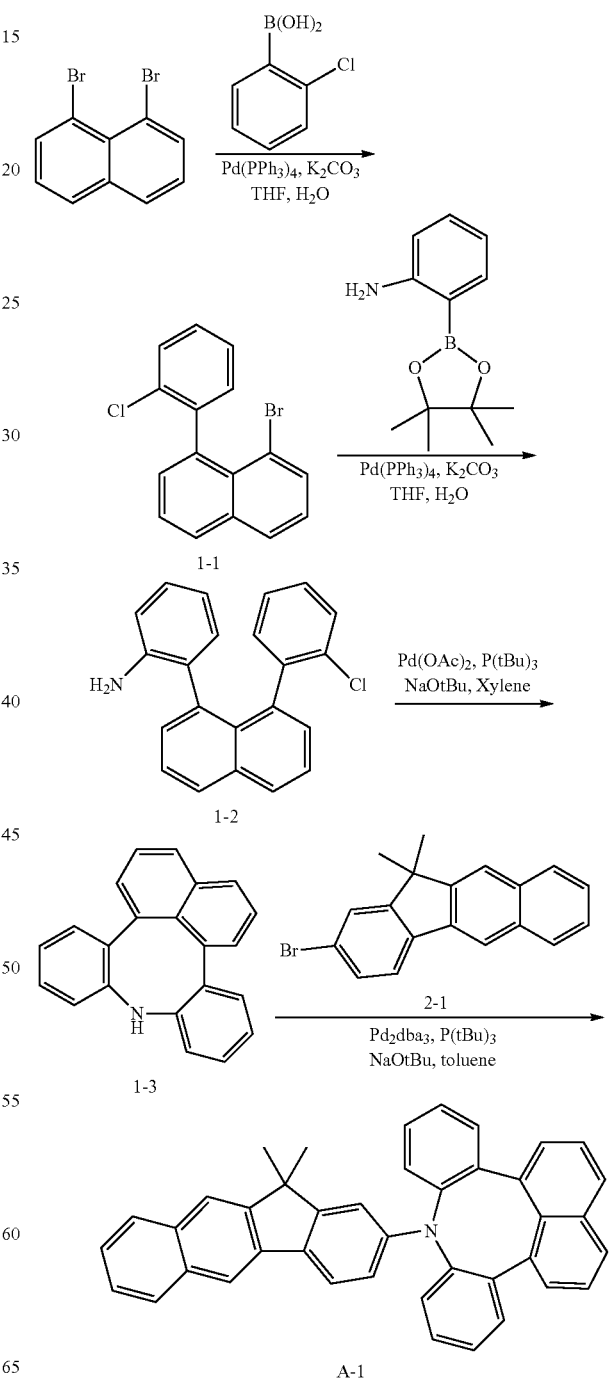

Preparation of Compound 1-1

100 g of 1,8-dibromonaphthalene (349.7 mmol), 82 g of (2-chlorophenyl)boronic acid (524.6 mmol), 20.2 g of tetrakis(triphenylphosphine)palladium(0) (Pd(PPh$_3$)$_4$) (17.5 mmol), and 120.8 g of potassium carbonate (874.5 mmol) were dissolved in 1500 mL of tetrahydrofuran and 400 mL of distilled water in a flask, and the mixture was refluxed at 100° C. for 18 hours. After completion of the reaction, an organic layer was extracted with ethyl acetate and residual moisture was removed using magnesium sulfate. The residue was dried and separated with column chromatography to obtain 78 g of compound 1-1 (yield: 70%).

Preparation of Compound 1-2

31 g of compound 1-1 (98.0 mmol), 27.8 g of 2-(4,4,5,5-tetramethyl-1,3,2-dioxylboren-2-yl)-aniline (127 mmol), 5.64 g of tetrakis(triphenylphosphine)palladium(0) (Pd(PPh$_3$)$_4$) (4.90 mmol), and 33.7 g of potassium carbonate (244 mmol) were dissolved in 520 mL of tetrahydrofuran and 130 mL of distilled water in a flask, and the mixture was refluxed at 100° C. for 18 hours. After completion of the reaction, an organic layer was extracted with ethyl acetate and residual moisture was removed using magnesium sulfate. The residue was dried and separated with column chromatography to obtain 32 g of compound 1-2 (yield: 100%).

Preparation of Compound 1-3

46 g of compound 1-2 (139 mmol), 1.56 g of palladium (II)acetate (Pd(OAc)$_2$) (6.95 mmol), 5.6 mL of tri-t-butylphosphine (13.9 mmol, 50% toluene solution), and 26.8 g of sodium t-butoxide (279 mmol) were dissolved in 700 mL of xylene in a flask, and the mixture was stirred under reflux for 18 hours. After cooling the mixture to room temperature, distilled water was added thereto. Next, an organic layer was extracted with ethyl acetate and dried with magnesium sulfate. The residue was distilled under reduced pressure and separated with column chromatography to obtain 17 g of compound 1-3 (yield: 41%).

Preparation of Compound A-1

7.0 g of compound 1-3 (24 mmol), 7.7 g of compound 2-1 (24 mmol), 1.1 g of tris(dibenzylideneacetone)dipalladium (0) (1.2 mmol), 0.9 mL of tri-t-butylphosphine (2.4 mmol, 50% toluene solution), and 4.6 g of sodium t-butoxide (48 mmol) were dissolved in 120 mL of toluene in a flask, and the mixture was refluxed for 4 hours. After cooling the mixture to room temperature, the solvent was removed with a rotary evaporator. Next, the residue was purified with column chromatography to obtain 2.5 g of white solid compound A-1 (yield: 20%).

M.P.=317° C., Tg=147° C.

Example 2: Preparation of Compound A-2

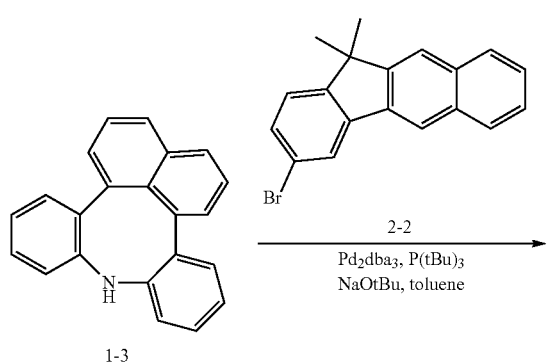

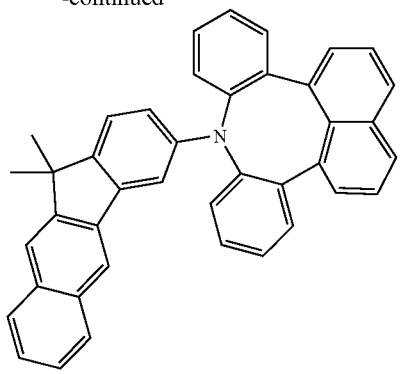

A-2

Preparation of Compound A-2

7.0 g of compound 1-3 (24 mmol), 7.7 g of compound 2-2 (24 mmol), 1.1 g of tris(dibenzylideneacetone)dipalladium (0) (1.2 mmol), 0.9 mL of tri-t-butylphosphine (2.4 mmol, 50% toluene solution), and 4.6 g of sodium t-butoxide (48 mmol) were dissolved in 120 mL of toluene in a flask, and the mixture was refluxed for 4 hours. After cooling the mixture to room temperature, the solvent was removed with a rotary evaporator. Next, the residue was purified with column chromatography to obtain 1.5 g of white solid compound A-2 (yield: 12%).

M.P.=272° C., Tg=161° C.

Example 3: Preparation of Compound A-126

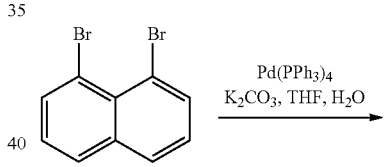

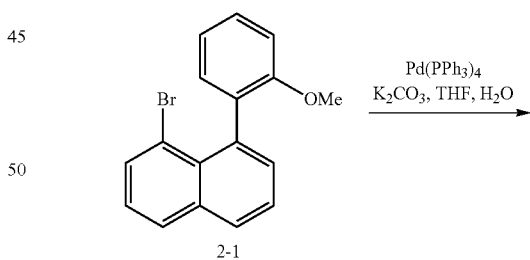

2-1

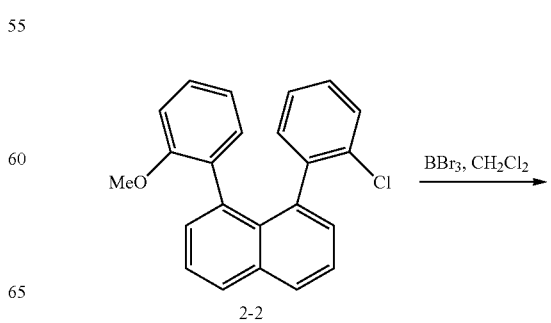

2-2

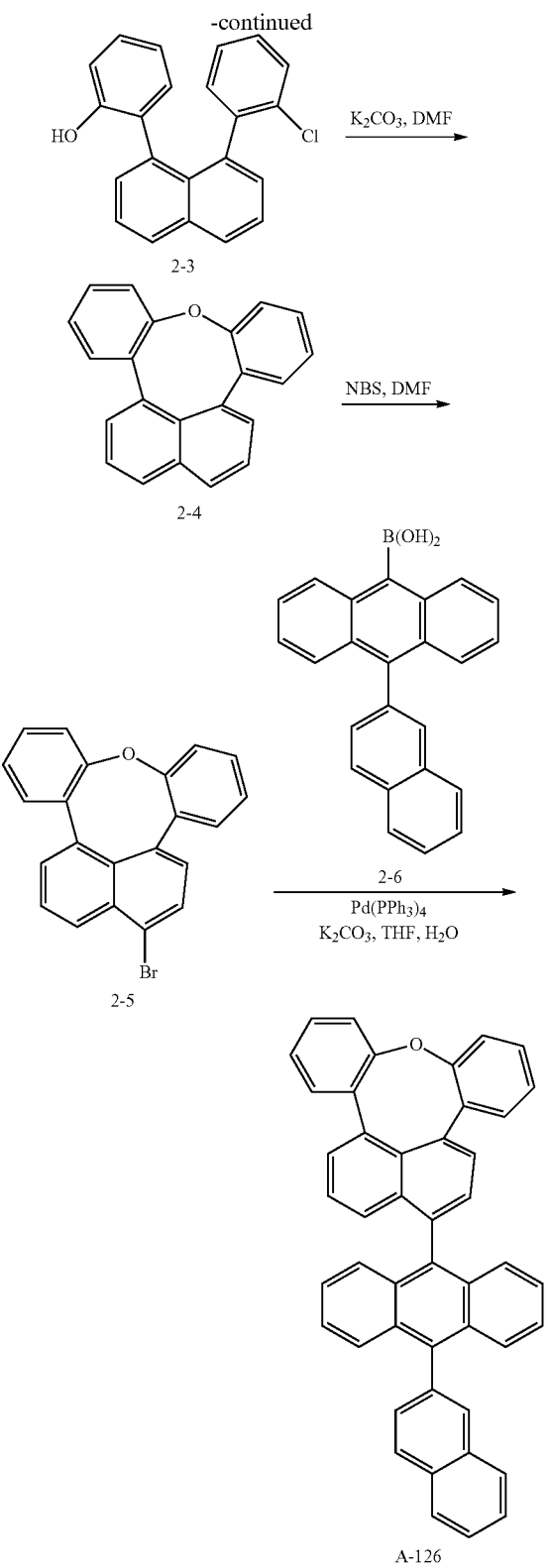

Preparation of Compound 2-1

50 g of 1,8-dibromonaphthalene (174.8 mmol), 24 g of (2-methoxyphenyl)boronic acid (157.3 mmol), 10 g of tetrakis(triphenylphosphine)palladium(0) (8.7 mmol), and 60 g of potassium carbonate (437.0 mmol) were dissolved in 880 mL of tetrahydrofuran and 200 mL of distilled water in a flask, and the mixture was refluxed at 100° C. for 18 hours. After completion of the reaction, an organic layer was extracted with ethyl acetate and residual moisture was removed using magnesium sulfate. The residue was dried and separated with column chromatography to obtain 55 g of compound 2-1 (yield: 100%).

Preparation of Compound 2-2

55 g of compound 2-1 (174.8 mmol), 31 g of (2-chlorophenyl)boronic acid (201.0 mmol), 10 g of tetrakis(triphenylphosphine)palladium(0) (8.7 mmol), and 60 g of potassium carbonate (437.0 mmol) were dissolved in 880 mL of tetrahydrofuran and 200 mL of distilled water in a flask, and the mixture was refluxed at 100° C. for 18 hours. After completion of the reaction, an organic layer was extracted with ethyl acetate and residual moisture was removed using magnesium sulfate. The residue was dried and separated with column chromatography to obtain 30 g of compound 2-2 (yield: 50%).

Preparation of Compound 2-3

3.3 g of compound 2-2 (9.57 mmol) was dissolved in 48 mL of methylene chloride in a flask, 11.5 mL of boron tribromide ($BBr_3$) (11.5 mmol) of methylene chloride 1.0 M was added thereto at 0° C., and the mixture was stirred at room temperature for 18 hours. The reaction solution was then diluted with methylene chloride and washed with distilled water. The extracted organic layer was dried with magnesium sulfate, and the solvent was removed with a rotary evaporator. The residue was separated with column chromatography to obtain 3 g of compound 2-3 (yield: 94%).

Preparation of Compound 2-4

3 g of compound 2-3 (9.1 mmol) and 1.9 g of potassium carbonate (13.7 mmol) were dissolved in 50 mL of dimethylformamide in a flask, and the mixture was refluxed at 160° C. for 18 hours. After completion of the reaction, an organic layer was extracted by introducing ethyl acetate and distilled water and residual moisture was removed using magnesium sulfate. The residue was dried and separated with column chromatography to obtain 2.2 g of compound 2-4 (yield: 81%).

Preparation of Compound 2-5

6 g of compound 2-4 (20.4 mmol) was dissolved in 102 mL of dimethylformamide in a flask, 4.4 g of N-bromosuccinimide (24.5 mmol) was added thereto, and the mixture was stirred at room temperature for 18 hours. The reaction solution was then diluted with ethyl acetate and washed with distilled water. The extracted organic layer was dried with magnesium sulfate, and the solvent was removed with a rotary evaporator. The precipitated solid was filtered and the residue was washed with cold methyl alcohol to obtain 5.5 g of compound 2-5 (yield: 72%).

Preparation of Compound A-126

5.5 g of compound 2-5 (14.7 mmol), 6.2 g of compound 2-6 (17.7 mmol), 0.86 g of tetrakis(triphenylphosphine) palladium(0) (0.74 mmol), and 5.1 g of potassium carbonate (36.9 mmol) were dissolved in 80 mL of tetrahydrofuran and 20 mL of distilled water in a flask, and the mixture was refluxed at 100° C. for 18 hours. After completion of the reaction, an organic layer was extracted with methylene chloride and residual moisture was removed using magnesium sulfate. The residue was dried and separated with column chromatography to obtain 2.8 g of compound A-126 (yield: 32%).

M.P.=344° C., Tg=190° C.

Device Examples 1 and 2: Production of an OLED According to the Present Disclosure An OLED comprising the organic electroluminescent compound of the present disclosure was produced as follows. A transparent electrode indium tin oxide (ITO) thin film (10 Ω/sq) on a glass substrate for an organic light-emitting diode (OLED) device (Geomatec, Japan) was subjected to an ultrasonic washing with acetone and isopropyl alcohol, sequentially, and was then stored in isopropyl alcohol. Next, the ITO substrate was mounted on a substrate holder of a vacuum vapor depositing apparatus. Compound HI-1 was introduced into a cell of said vacuum vapor depositing apparatus, and then the pressure in the chamber of said apparatus was controlled to $10^{-6}$ torr. Thereafter, an electric current was applied to the cell to evaporate the above-introduced material, thereby forming a first hole injection layer having a thickness of 90 nm on the ITO substrate. Compound HI-2 was then introduced into another cell of said vacuum vapor depositing apparatus, and was evaporated by applying an electric current to the cell, thereby forming a second hole injection layer having a thickness of 5 nm on the first hole injection layer. Compound HT-1 was introduced into another cell of said vacuum vapor depositing apparatus, and was evaporated by applying an electric current to the cell, thereby forming a first hole transport layer having a thickness of 10 nm on the second hole injection layer. The compounds listed in Table 1 below for a second hole transport layer (auxiliary layer) were introduced into another cell of said vacuum vapor depositing apparatus, and was evaporated by applying an electric current to the cell, thereby forming a second hole transport layer (or auxiliary layer) having a thickness of 60 nm on the first hole transport layer. After forming the hole injection layers and the hole transport layers (or auxiliary layer), a light-emitting layer was then deposited as follows. Compound H-1 was introduced into one cell of the vacuum vapor depositing apparatus as a host of the light-emitting layer, and compound D-39 was introduced into another cell as a dopant. The two materials were evaporated and were deposited in a doping amount of 2 wt % (the amount of dopant) based on the total amount of the host and dopant to form a light-emitting layer having a thickness of 40 nm on the second hole transport layer. Compound ET-1 and compound EI-1 were then introduced into another two cells, evaporated at the rate of 1:1, and deposited to form an electron transport layer having a thickness of 35 nm on the light-emitting layer. Next, after depositing compound EI-1 as an electron injection layer having a thickness of 2 nm on the electron transport layer, an Al cathode having a thickness of 80 nm was deposited by another vacuum vapor deposition apparatus on the electron injection layer. Thus, an OLED was produced.

Comparative Example: Production of an OLED Not According to the Present Disclosure An OLED was produced in the same manner as in Device Examples 1 and 2, except for using the compounds listed in Table 1 below for the second hole transport layer (or auxiliary layer).

The driving voltage, luminous efficiency, and CIE color coordinates at a luminance of 1,000 nit of the OLEDs produced in Examples 1 and 2 and the Comparative Example as above are provided in Table 1 below.

TABLE 1

| | Second Hole Transport Material (Auxiliary Material) | Host | Driving Voltage (V) (@1,000 nit) | Luminous Efficiency (cd/A) (@1,000 nit) | CIE (x, y) | |
|---|---|---|---|---|---|---|
| Device Example 1 | A-1 | H-1 | 2.7 | 20.0 | 0.665 | 0.333 |
| Device Example 2 | A-2 | | 5.1 | 28.5 | 0.669 | 0.331 |
| Comparative Example | Ref-1 | | 3.2 | 11.4 | 0.661 | 0.336 |

The compounds used in Device Examples 1 and 2, and the Comparative Example are as follows:

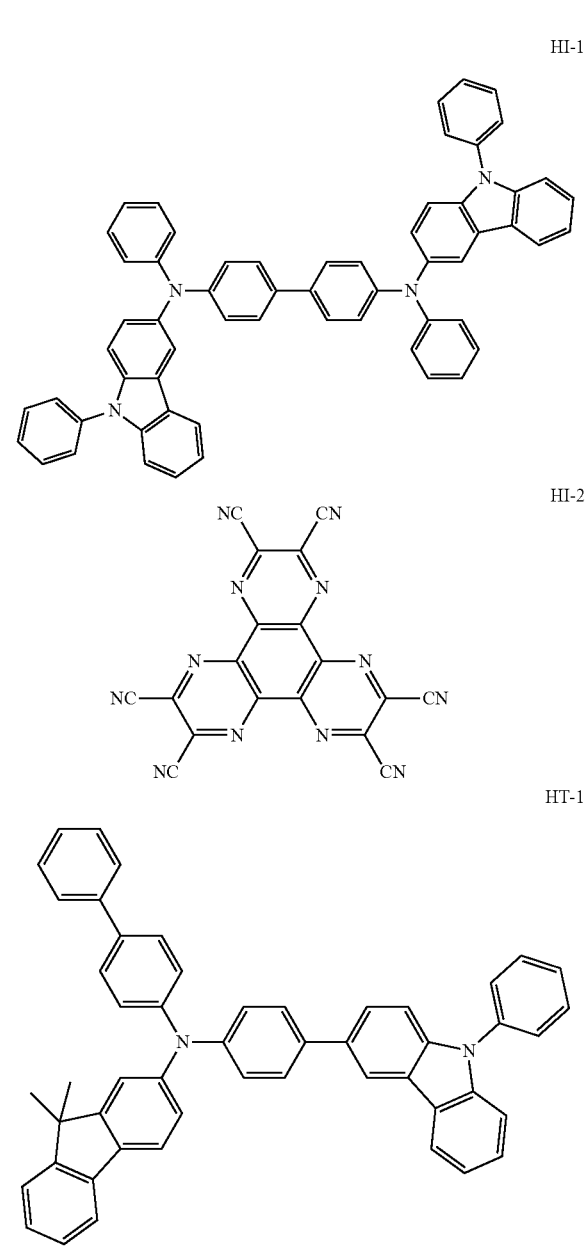

ET-1

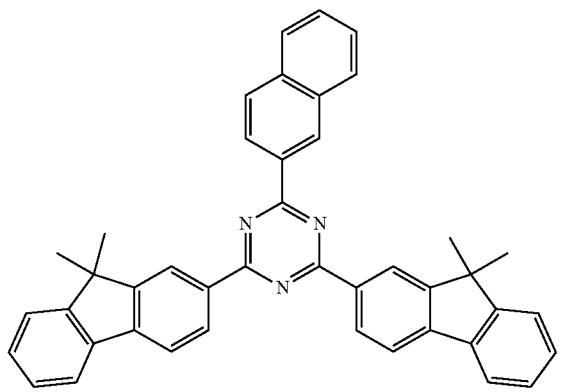

EI-1

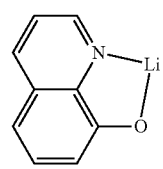

H-1

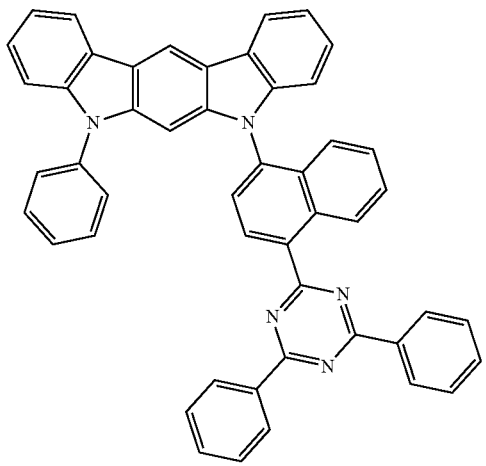

D-39

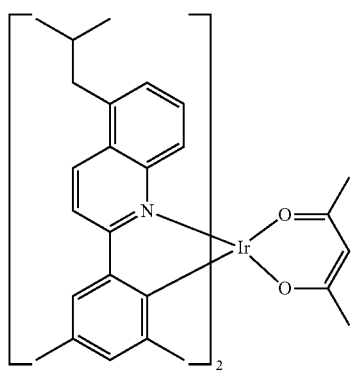

A-1

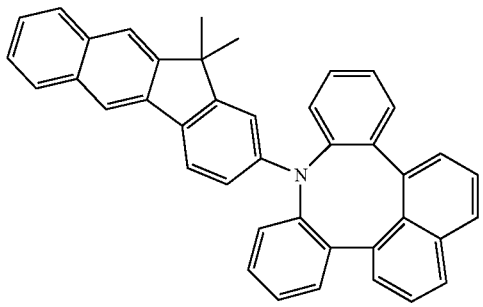

A-2

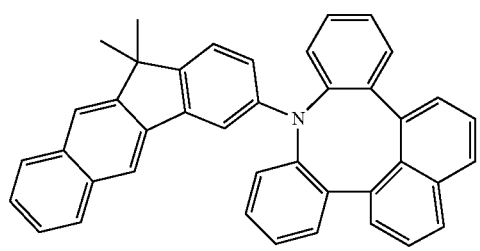

Ref-1

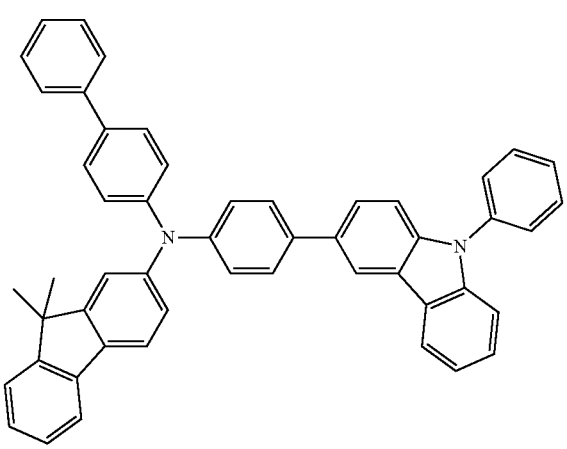

As confirmed in Table 1, the organic electroluminescent compound according to the present disclosure showed superior driving voltage and/or luminous efficiency characteristics, compared to the conventional organic electroluminescent compound, when used as a second hole transport material.

The invention claimed is:

1. An organic electroluminescent compound represented by the following formula 1:

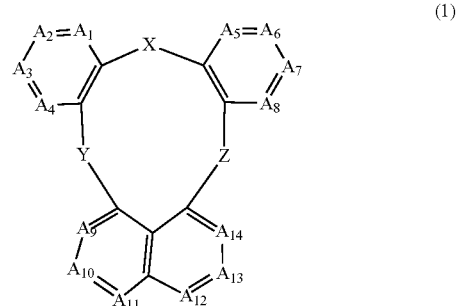

(1)

wherein

X, Y, and Z each independently represent a single bond, O, S, $NR_1$, or $CR_2R_3$, with a proviso that not all of X, Y, and Z are a single bond;

$R_1$ represents a substituted or unsubstituted (C6-C30)aryl, or a substituted or unsubstituted (3- to 30-membered) heteroaryl;

$R_2$ and $R_3$ each independently represent a substituted or unsubstituted (C1-C30)alkyl, a substituted or unsubstituted (C6-C30)aryl, or a substituted or unsubstituted (3- to 30-membered)heteroaryl; or $R_2$ and $R_3$ may be linked to each other to form a ring(s), where if a plurality of $R_2$ to $R_3$ is present, each of $R_2$, and each of $R_3$ may be the same or different;

$A_1$ to $A_4$, $A_5$ to $A_8$, $A_9$ to $A_{11}$ and $A_{12}$ to $A_{14}$ each independently represent $CR_4$ or N; and $R_4$ each independently represents hydrogen, deuterium, a halogen, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted mono- or di-(C6-C30)arylamino, or a substituted or unsubstituted (C1-C30)alkyl (C6-C30)arylamino; or two or more adjacent $R_4$'s may be linked to each other to form a ring(s)

wherein in $R_1$ to $R_4$, the substituents of the substituted alkyl, the substituted aryl, the substituted heteroaryl, the substituted cycloalkyl, the substituted mono- or di-arylamino, and the substituted alkylarylamino each independently are at least one selected from the group consisting of deuterium; a halogen; a cyano; a nitro; a (C1-C30)alkyl; a (C3-C30)cycloalkyl; a (3- to 7-membered)heterocycloalkyl; a (3- to 30-membered)heteroaryl unsubstituted or substituted with a (C6-C30) aryl(s); a (C6-C30)aryl unsubstituted or substituted with one or more of a (C1-C30)alkyl(s) and a (3- to 30-membered)heteroaryl(s); a (C6-C30)aryl(C1-C30) alkyl; and a (C1-C30)alkyl(C6-C30)aryl.

2. The organic electroluminescent compound according to claim 1, wherein formula 1 is represented by the following formula 2 or 3:

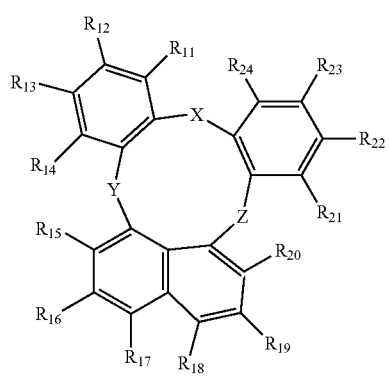

(2)

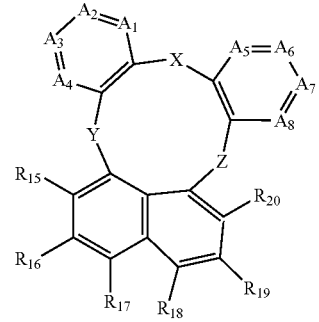

(3)

wherein

X, Y, Z, and $A_1$ to $A_8$ are as defined in claim 1, with a proviso that at least one of $A_1$ to $A_8$ is N; and $R_{11}$ to $R_{24}$ are identical to $R_4$ in claim 1.

3. The organic electroluminescent compound according to claim 1, wherein formula 1 is represented by any one of the following formulas:

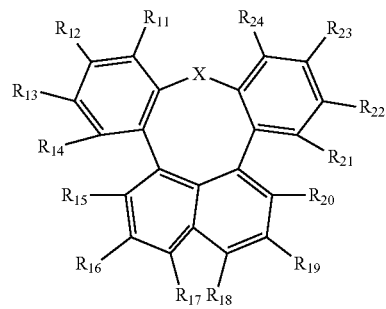

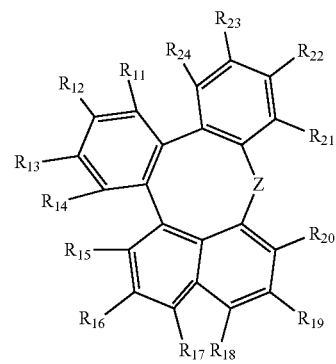

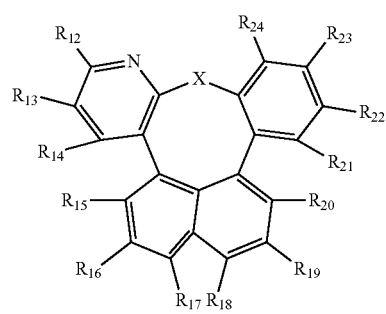

-continued

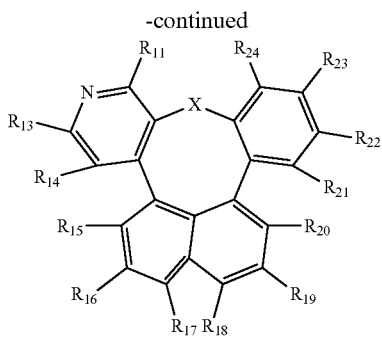

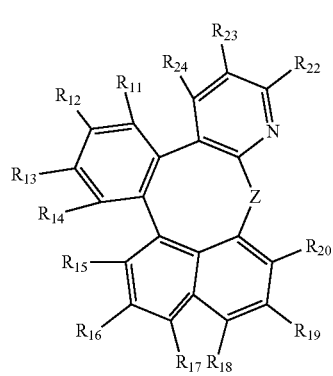

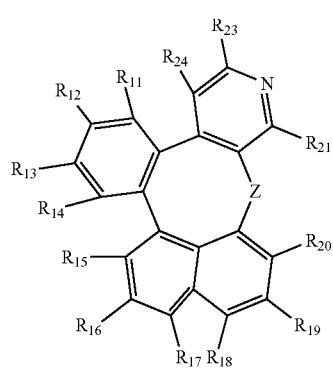

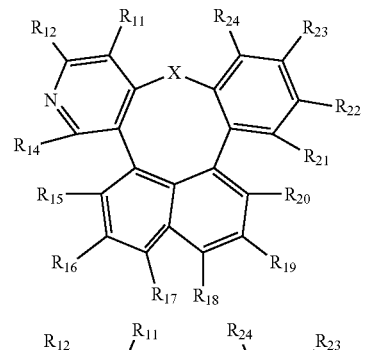

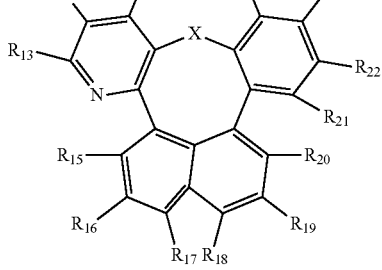

-continued

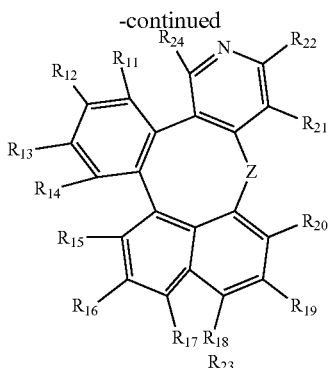

wherein
X and Z each independently represent O, S, NR$_1$, or CR$_2$R$_3$;
R$_1$ to R$_3$ are as defined in claim 1; and
R$_{11}$ to R$_{24}$ are identical to R$_4$ in claim 1.

4. The organic electroluminescent compound according to claim 1, wherein
R$_1$ represents a substituted or unsubstituted (C6-C30)aryl, or a substituted or unsubstituted (5- to 15-membered) heteroaryl;
R$_2$ and R$_3$ each independently represent a substituted or unsubstituted (C1-C6)alkyl, or a substituted or unsubstituted (C6-C12)aryl; and
R$_4$ each independently represents hydrogen, a substituted or unsubstituted (C6-C30)aryl, a substituted or unsubstituted (5- to 15-membered)heteroaryl, or a substituted or unsubstituted di(C6-C20)arylamino;
wherein in R$_1$ to R$_4$, the substituents of the substituted aryl, the substituted heteroaryl, the substituted alkyl, and the substituted di-arylamino each independently are at least one selected from the group consisting of deuterium; a halogen; a cyano; a nitro; a (C1-C30) alkyl; a (C3-C30)cycloalkyl; a (3- to 7-membered) heterocycloalkyl; a (3- to 30-membered)heteroaryl unsubstituted or substituted with a (C6-C30)aryl(s); a (C6-C30)aryl unsubstituted or substituted with one or more of a (C1-C30)alkyl(s) and a (3- to 30-membered) heteroaryl(s); a (C6-C30)aryl(C1-C30)alkyl; and a (C1-C30)alkyl(C6-C30)aryl.

5. The organic electroluminescent compound according to claim 1, wherein
R$_1$ represents a (C6-C30)aryl unsubstituted or substituted with one or more of a (C1-C6)alkyl(s), a (C6-C20) aryl(s), a (5- to 15-membered)heteroaryl(s), and a di(C6-C20)arylamino(s); or a (5- to 15-membered) heteroaryl unsubstituted or substituted with a (C6-C12) aryl(s),
R$_2$ and R$_3$ each independently represent an unsubstituted (C1-C6)alkyl, or an unsubstituted (C6-C12)aryl, and R₄ each independently represents hydrogen; a (C6-C30) aryl unsubstituted or substituted with one or more of a (C6-C12)aryl(s) and a (5- to 15-membered)heteroaryl(s); a (5- to 15-membered)heteroaryl unsubstituted or substituted with a (C6-C12)aryl(s); or a di(C6-C20) arylamino unsubstituted or substituted with a (C1-C6) alkyl(s).

6. The organic electroluminescent compound according to claim 1, wherein the compound represented by formula 1 is selected from the following compounds:

A-1
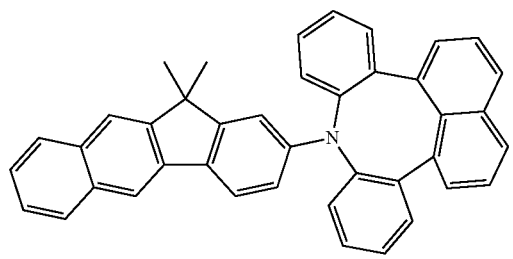

A-2
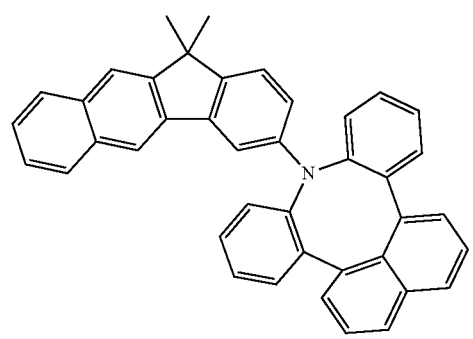

A-3
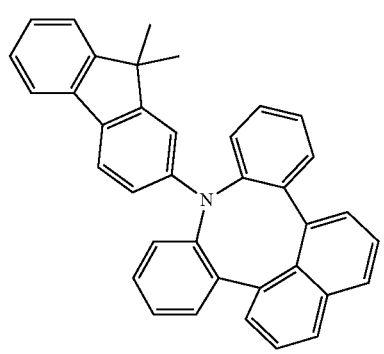

A-4
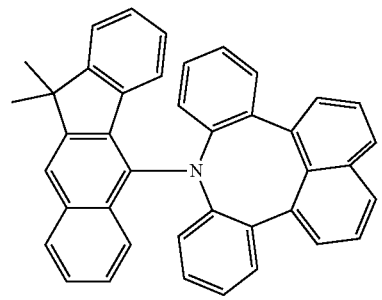

A-5
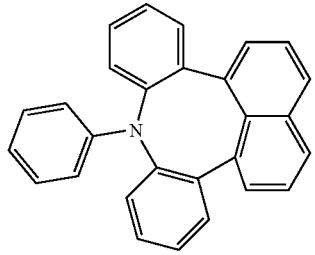

A-6
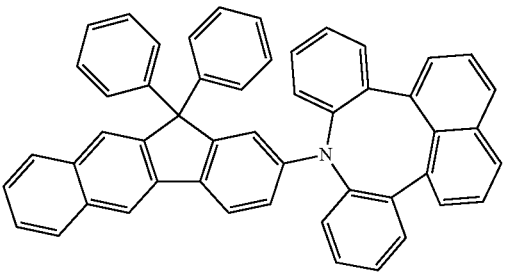

A-7
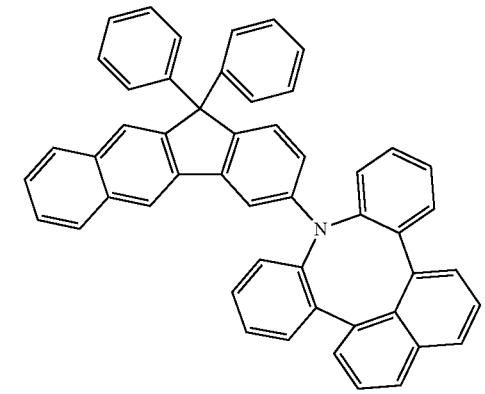

A-8
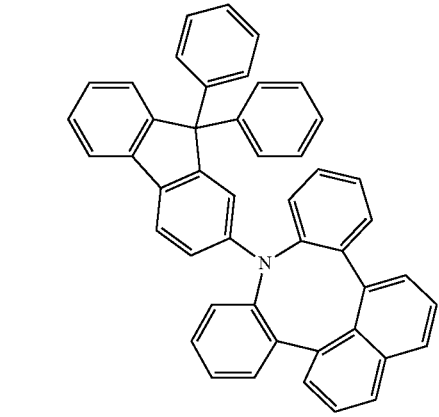

-continued
A-9
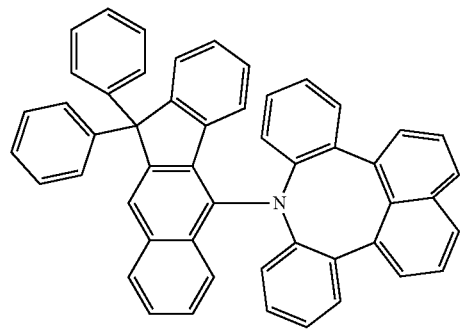
A-10
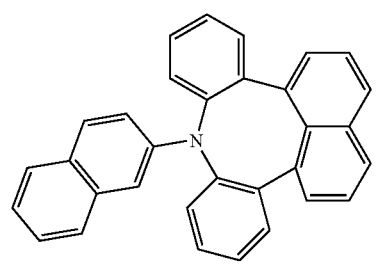
A-11
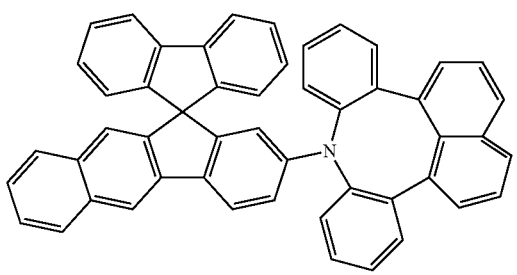
A-12
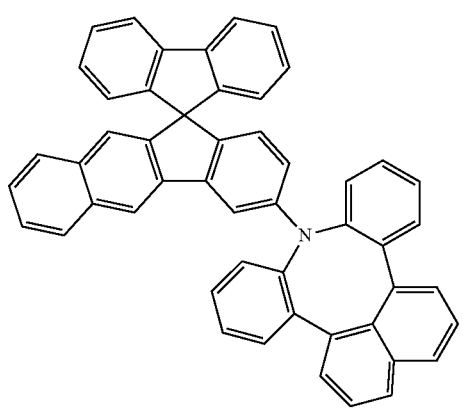
-continued
A-13
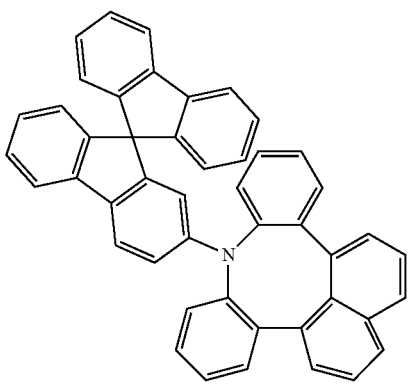
A-14
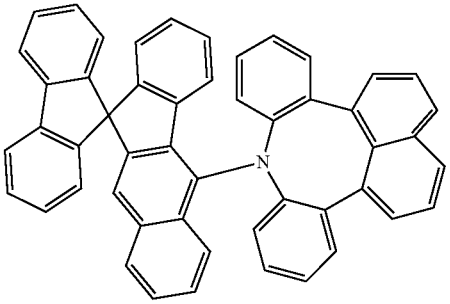
A-15
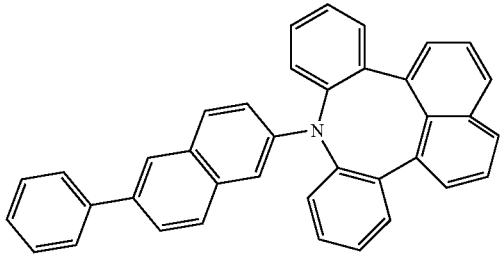
A-16
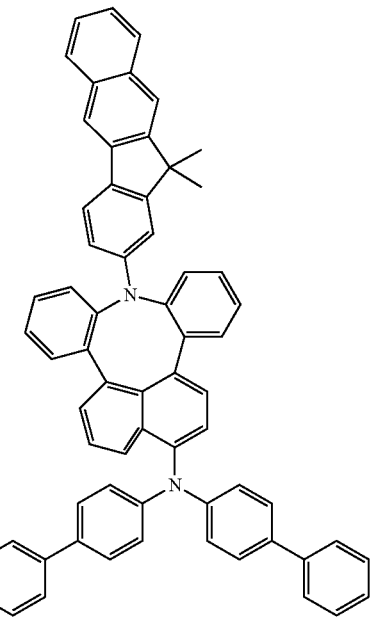

A-17
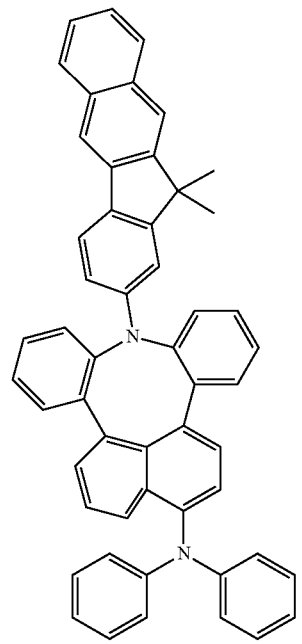
A-18
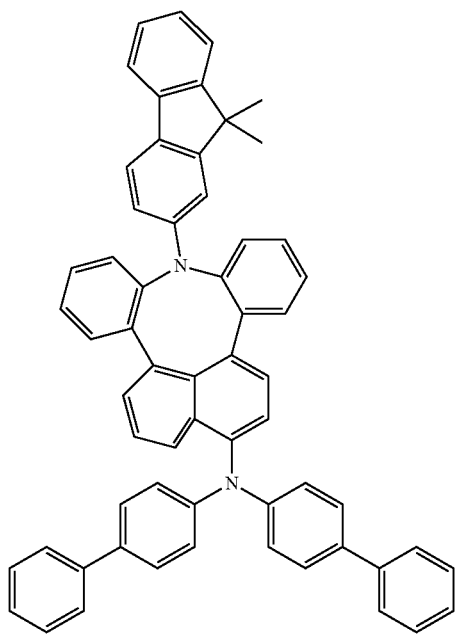
A-19
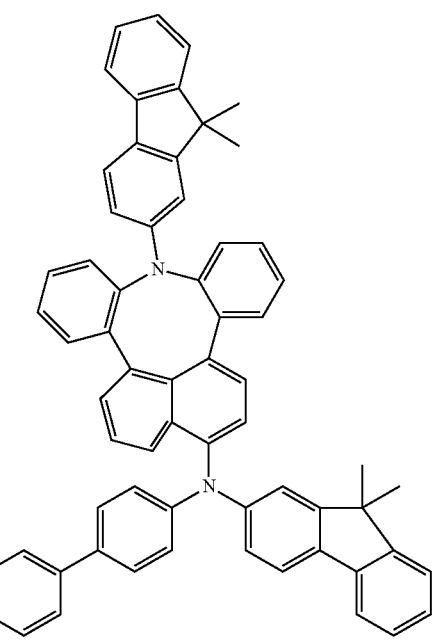
A-20
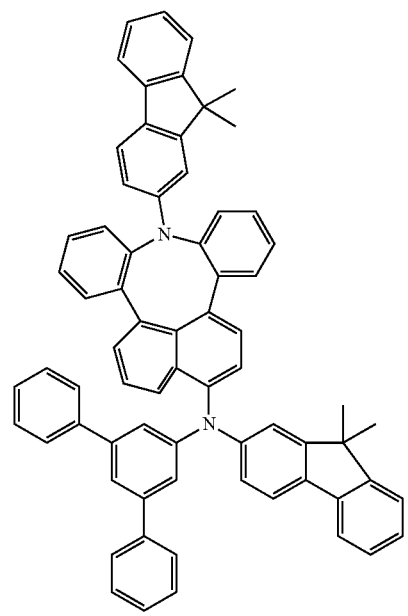

A-21
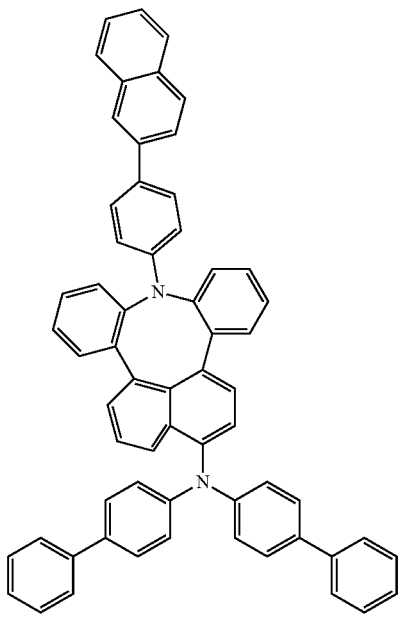
A-22
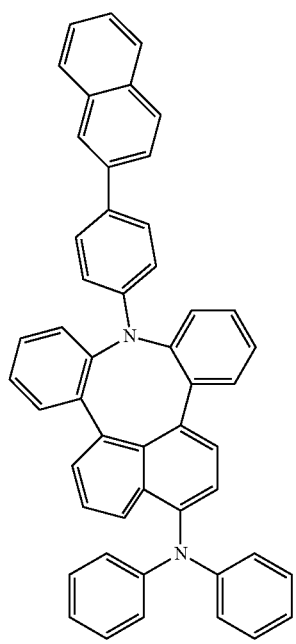
A-23
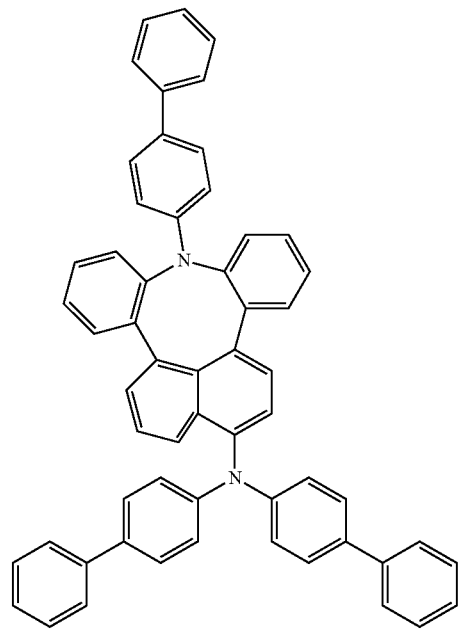
A-24
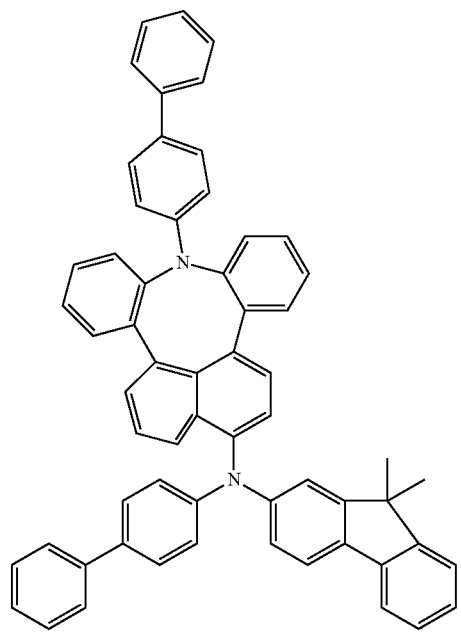

A-25
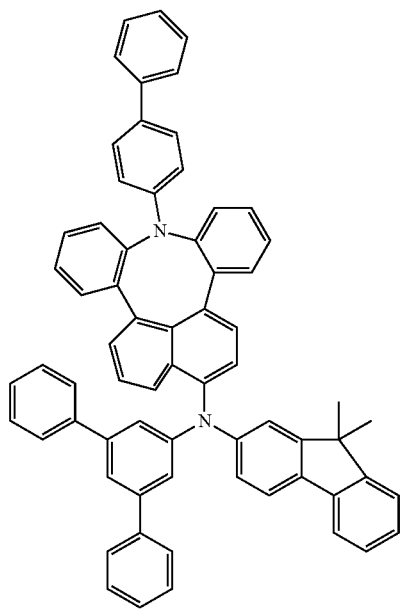
A-26
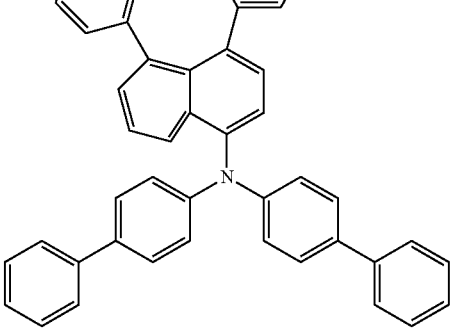
A-27
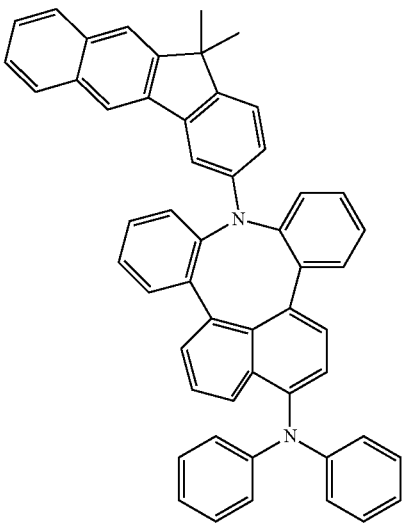
A-28
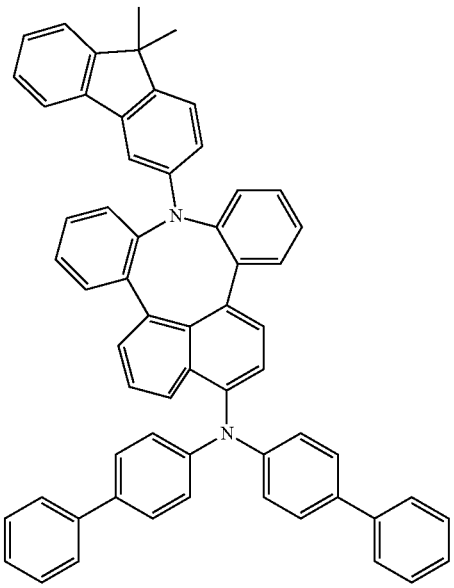

A-29
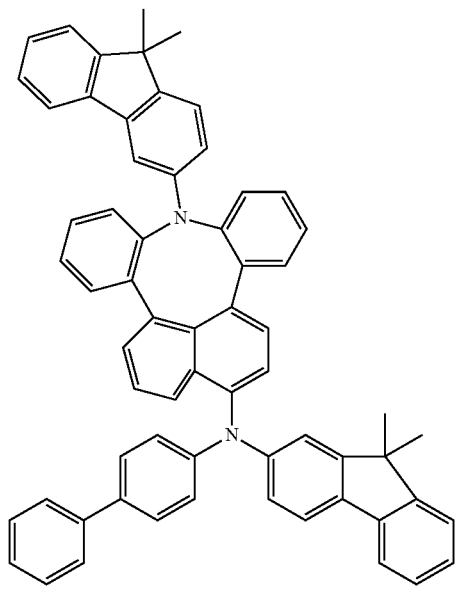
A-30
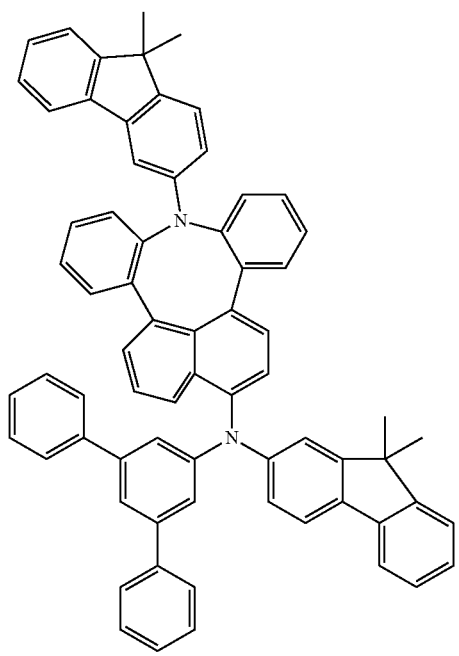
A-31
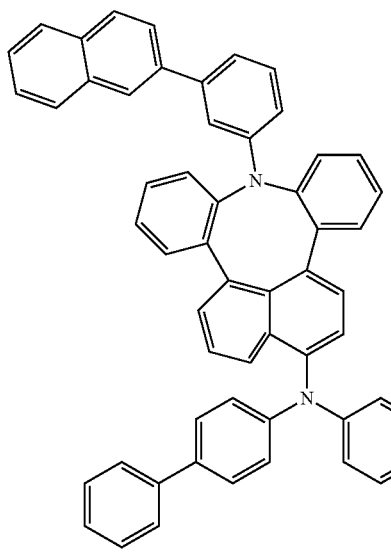
A-32
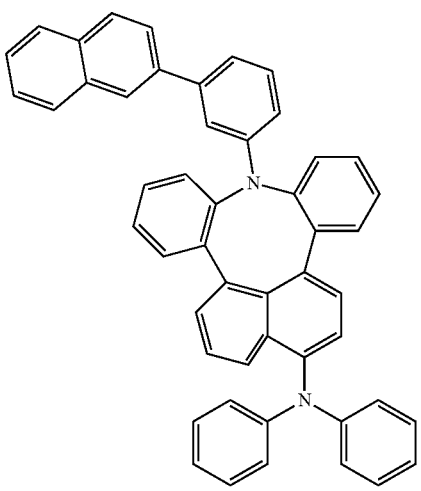
A-33
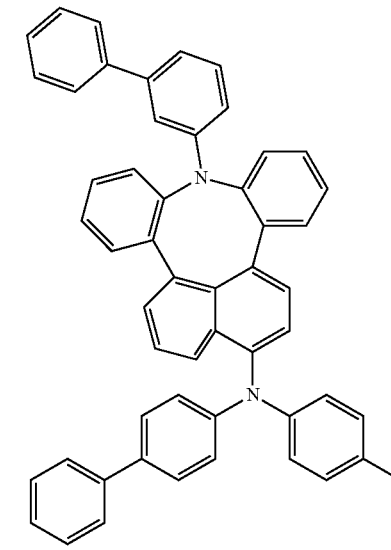

A-34
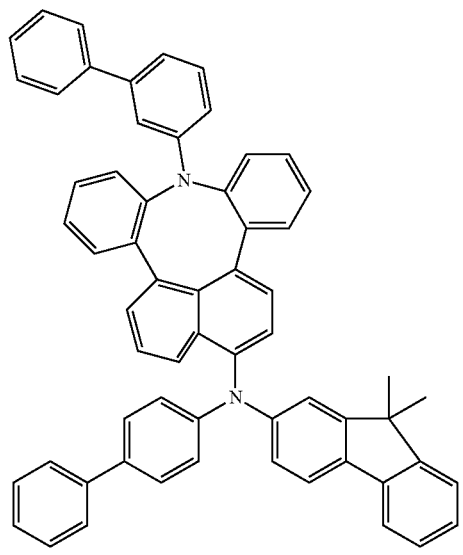
A-35
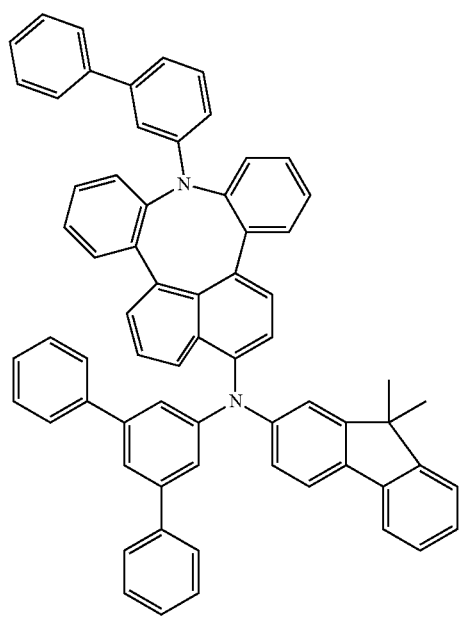
A-36
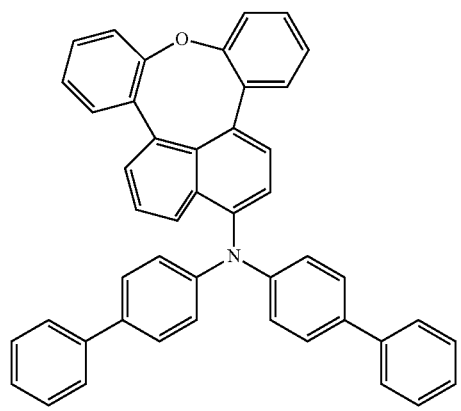
A-37
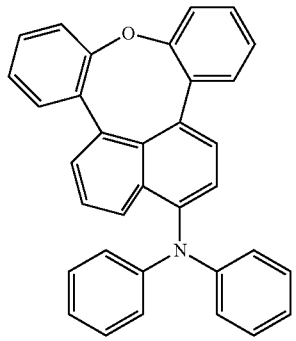
A-38
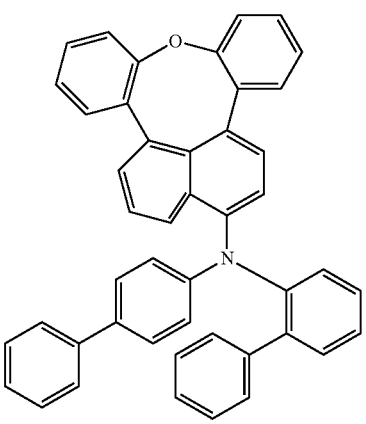
A-39
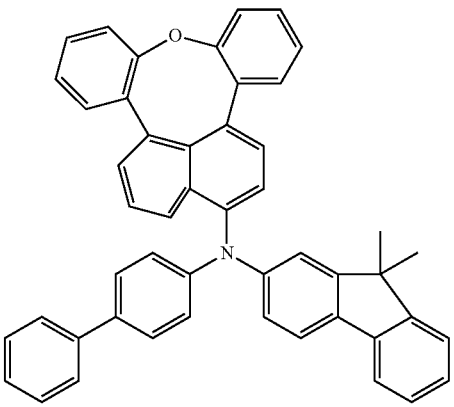
A-40
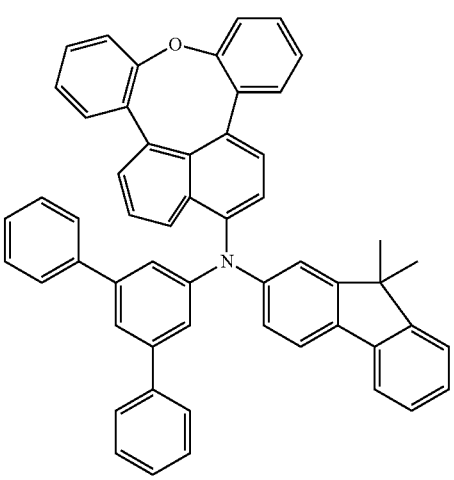

-continued
A-41
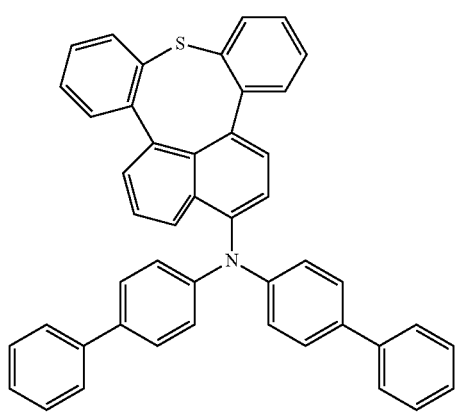
A-42
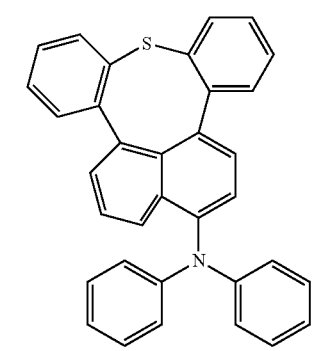
A-43
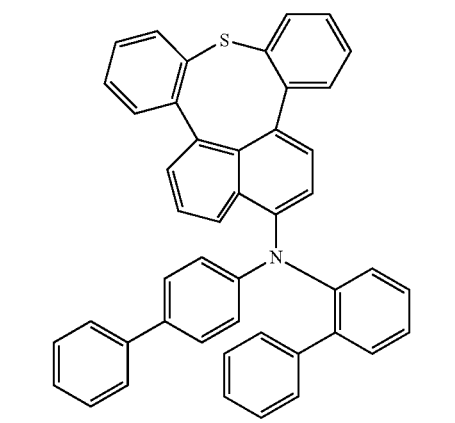
A-44
A-45
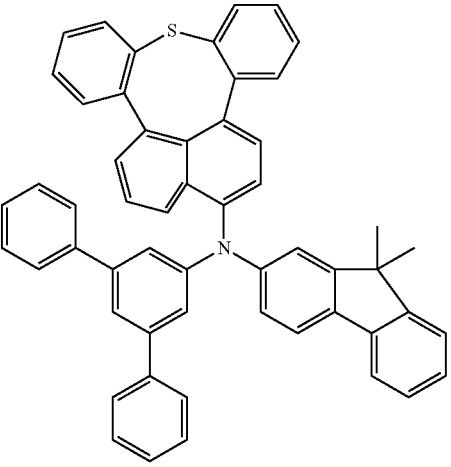
A-46
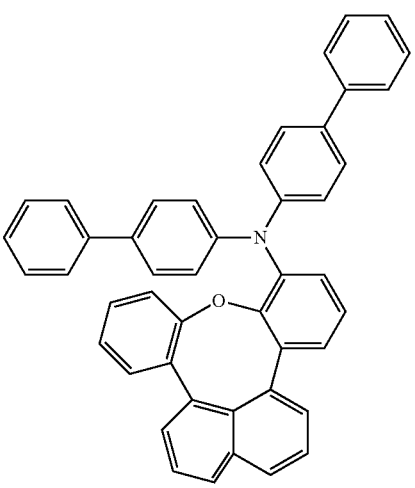
A-47
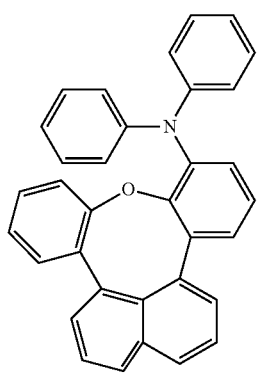

-continued
A-48
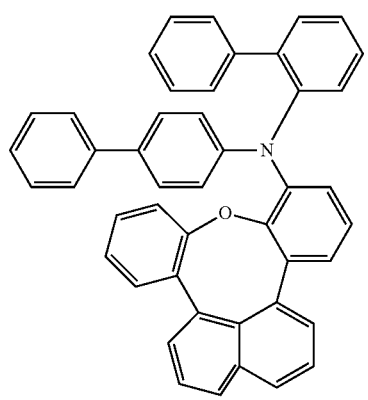
A-49
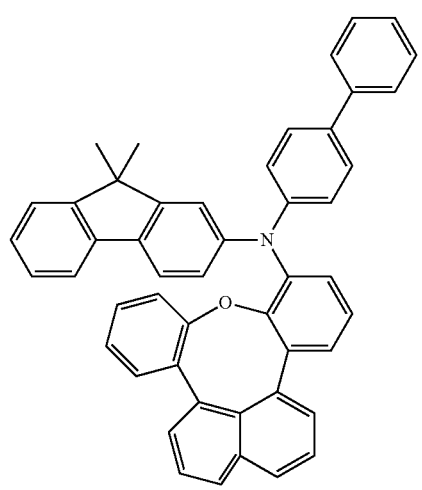
A-50
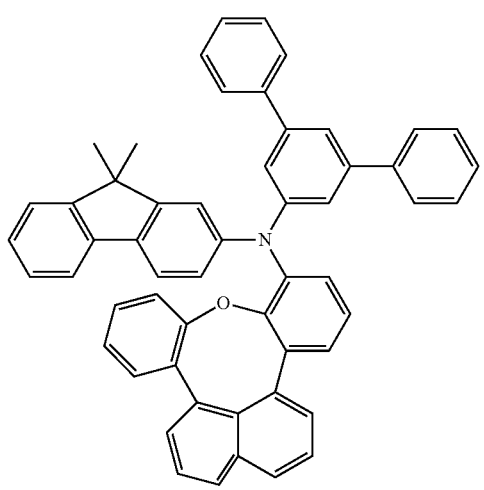
-continued
A-51
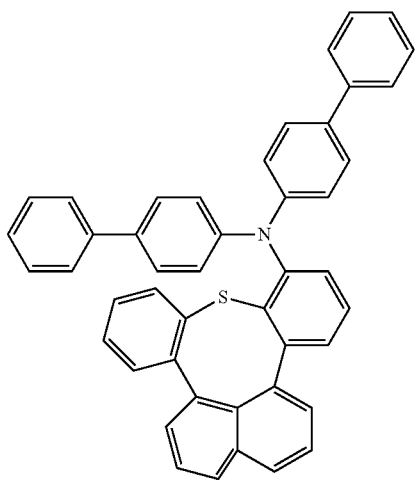
A-52
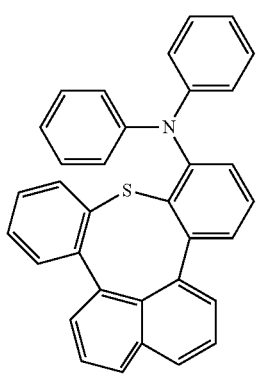
A-53
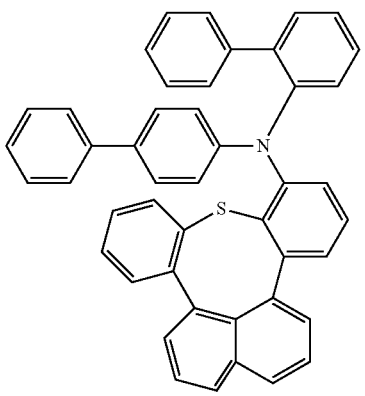

A-54
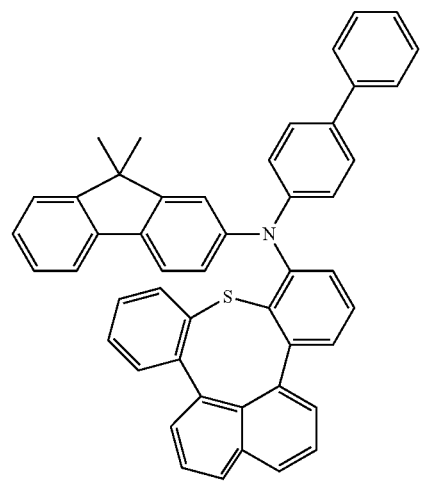
A-55
A-56
A-57
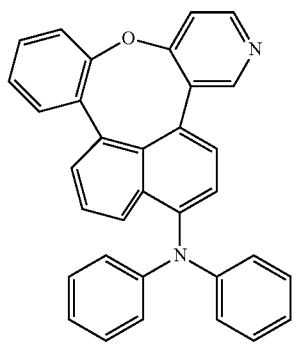
A-58
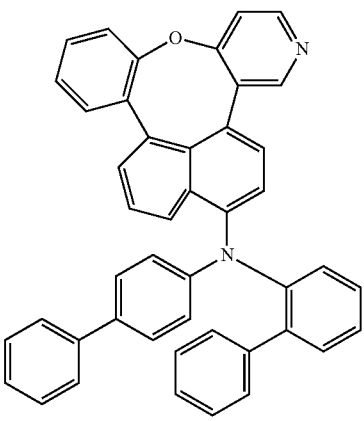
A-59
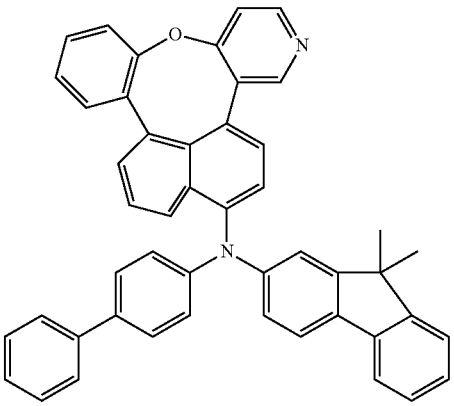
A-60
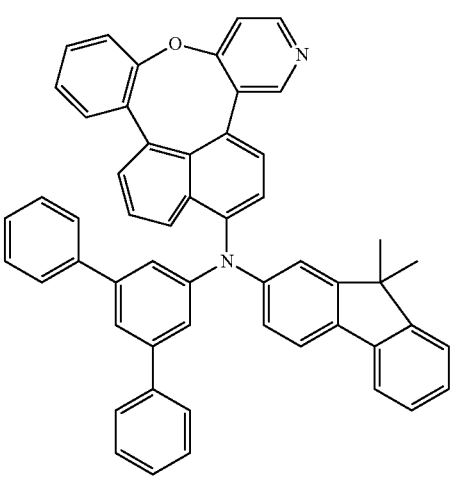

-continued
A-61
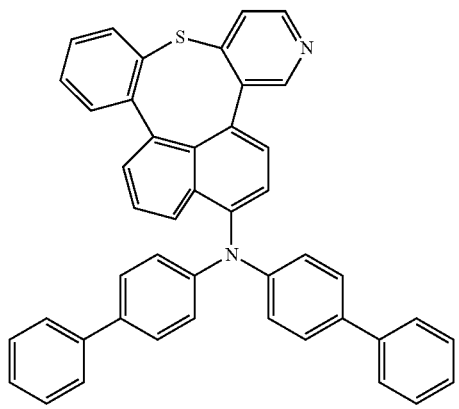
A-62
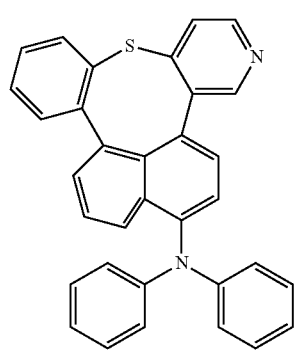
A-63
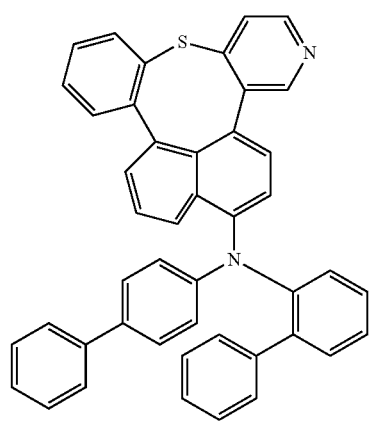
A-64
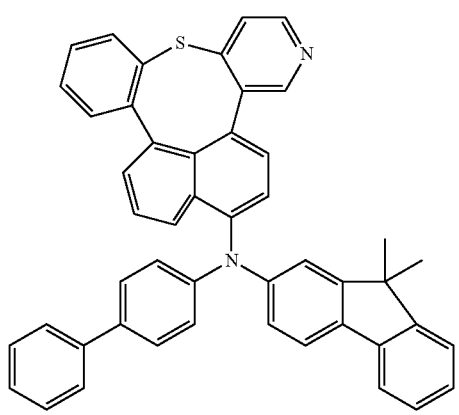
-continued
A-65
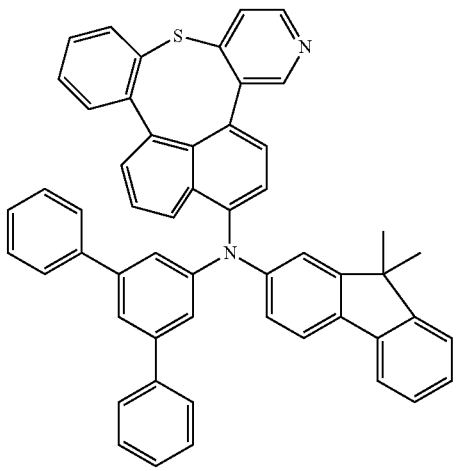
A-66
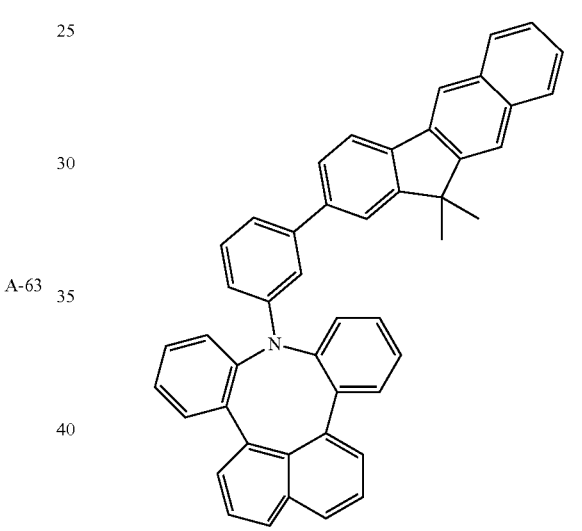
A-67
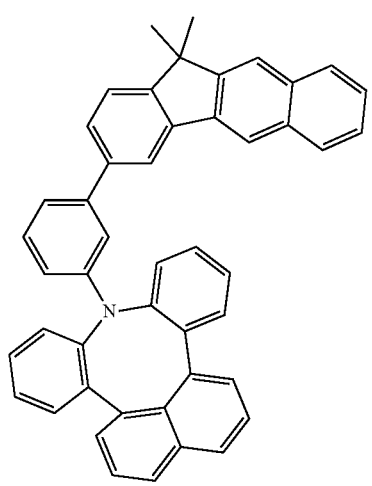

-continued
A-68
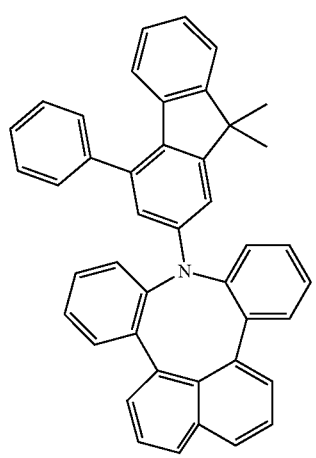
A-69
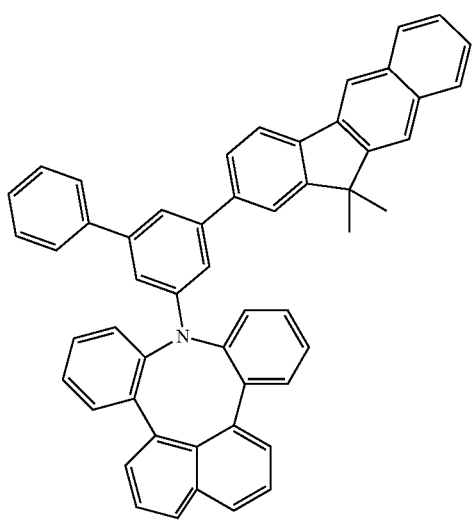
A-70
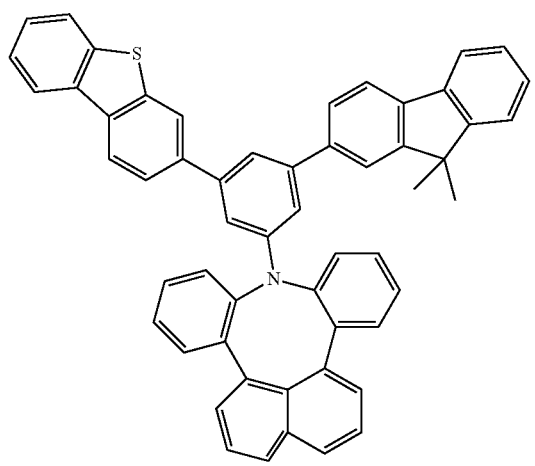
-continued
A-71
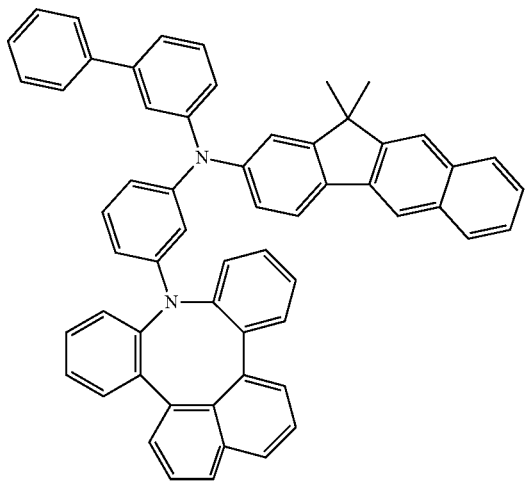
A-72
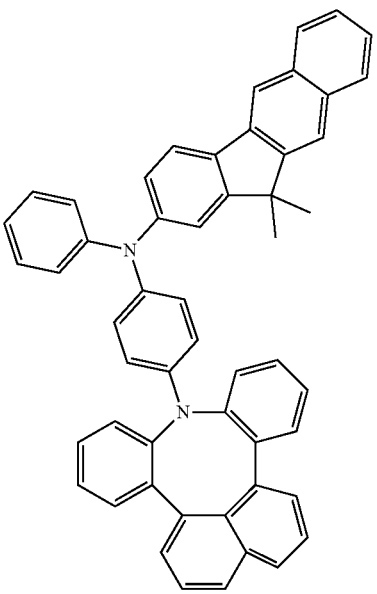
A-73
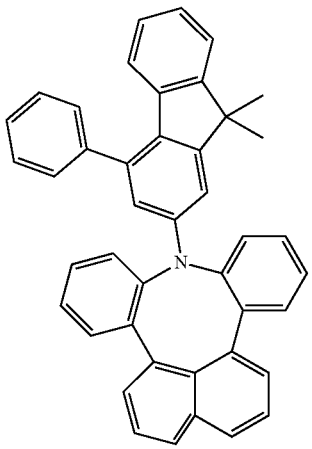

A-74
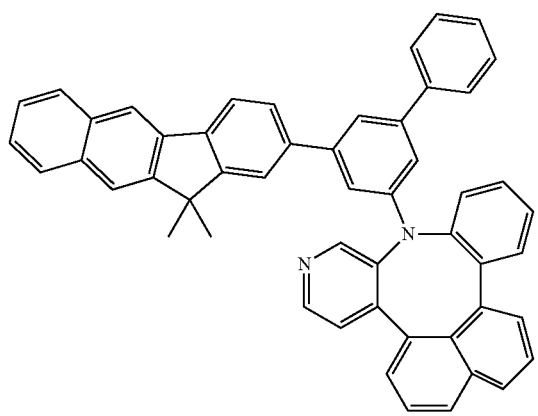
A-77
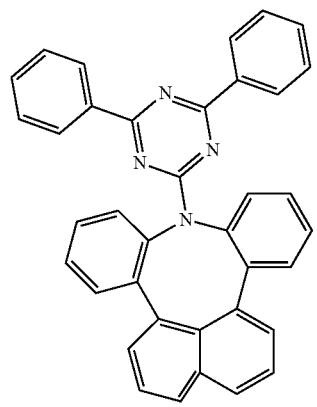
A-75
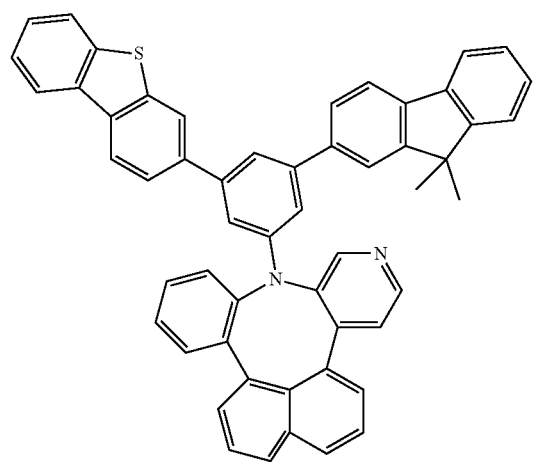
A-78
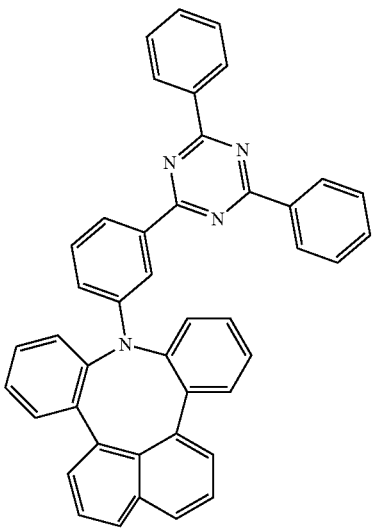
A-76
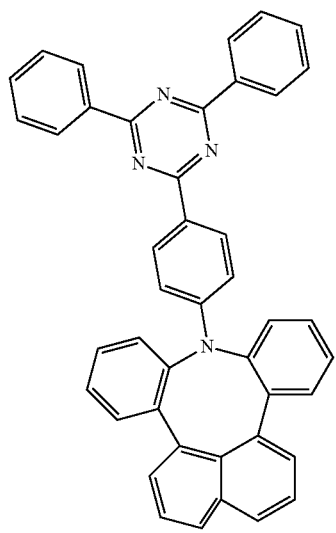
A-79
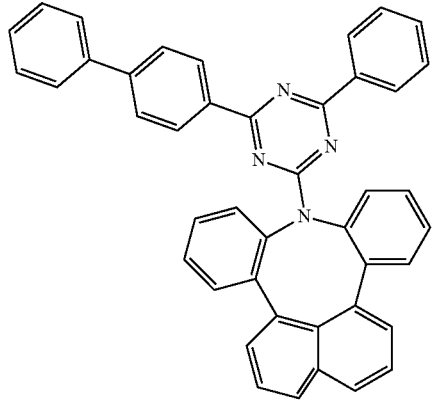

A-80
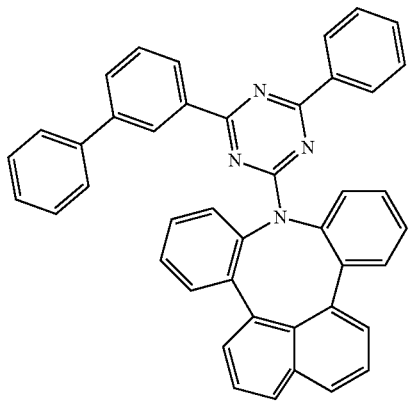
A-81
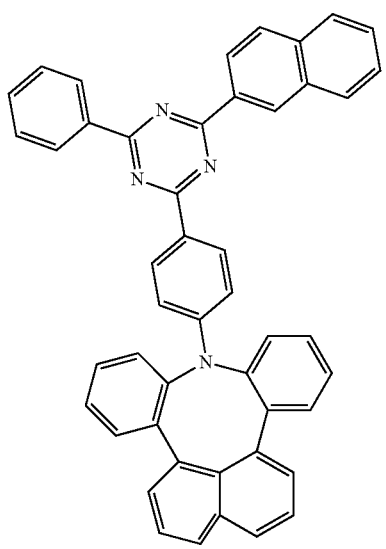
A-82
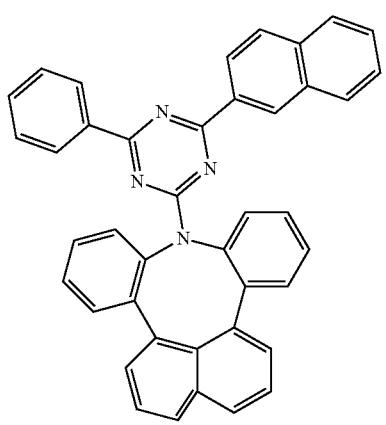
A-83
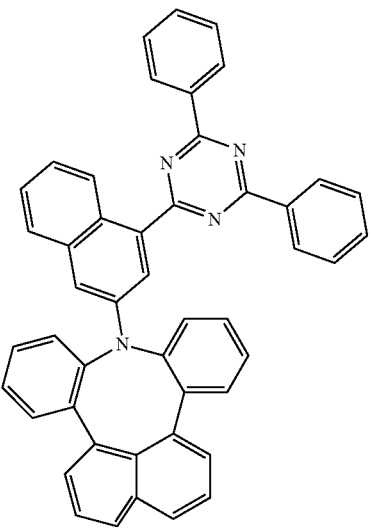
A-84
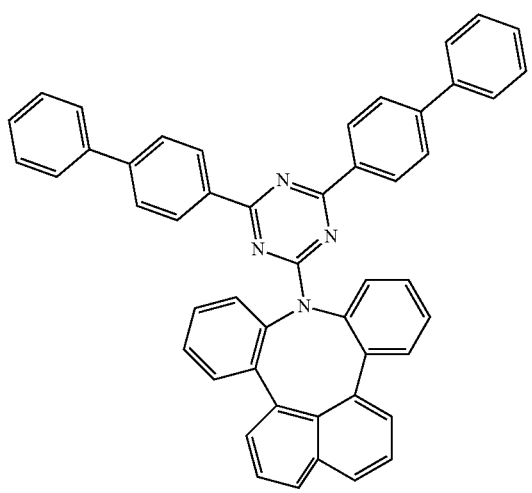
A-85
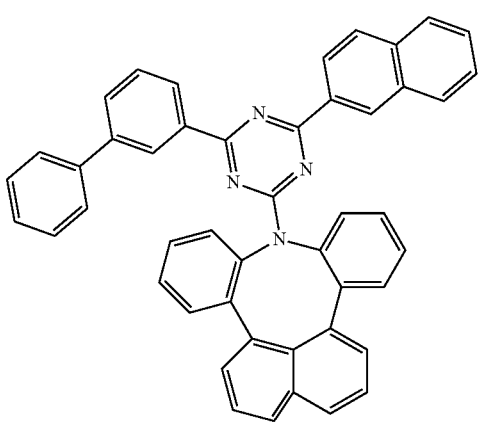

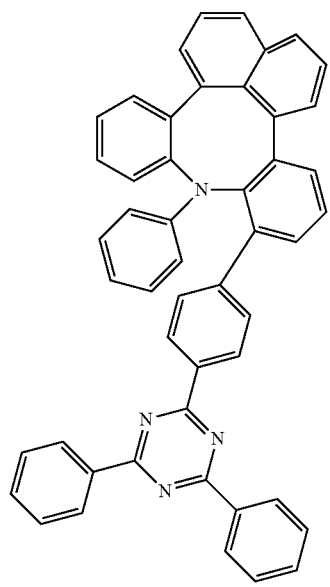
A-86
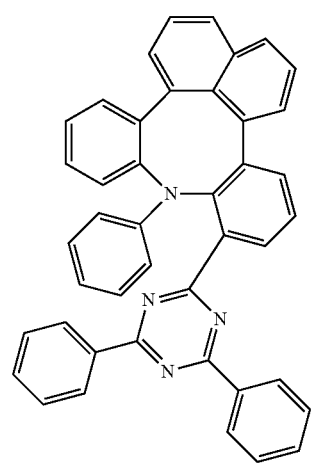
A-87
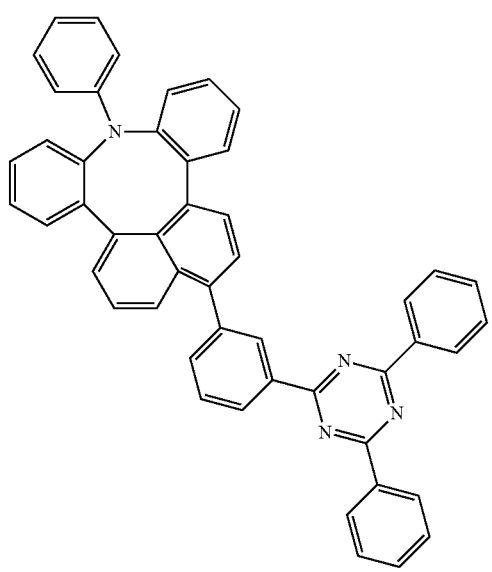
A-88
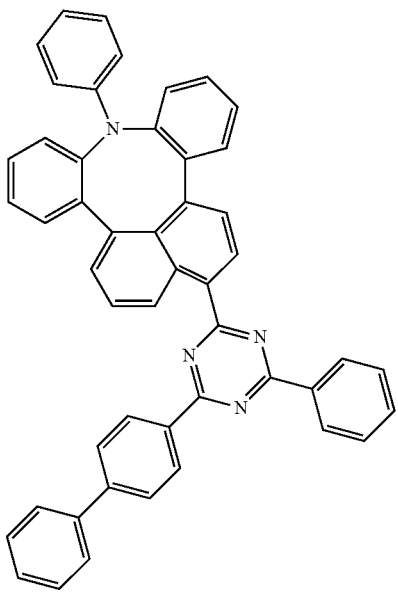
A-89
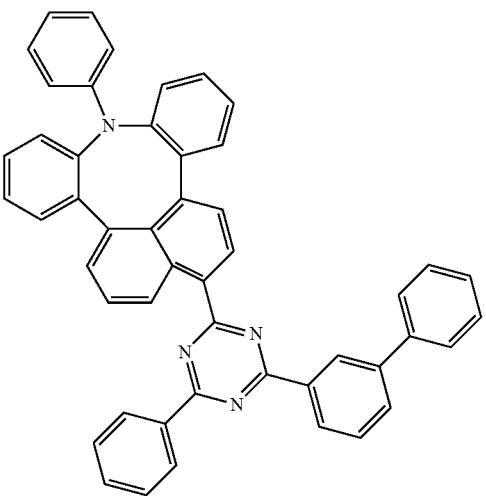
A-90

A-91
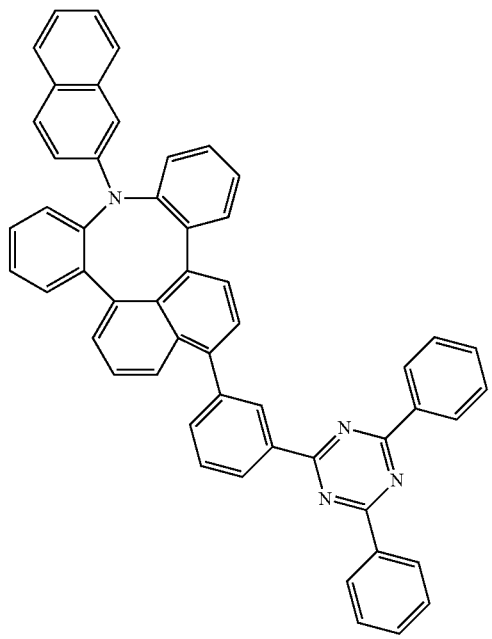
A-93
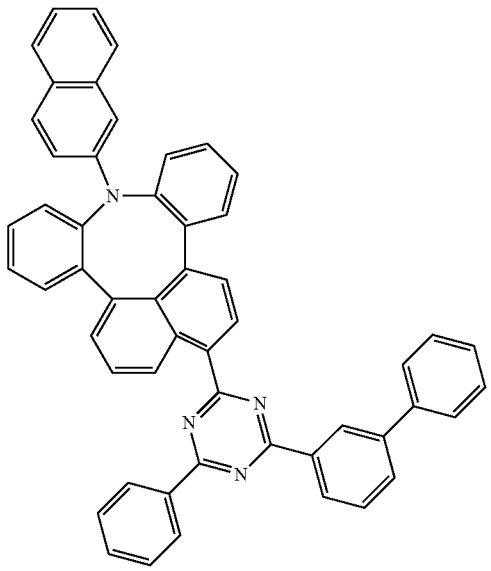
A-92
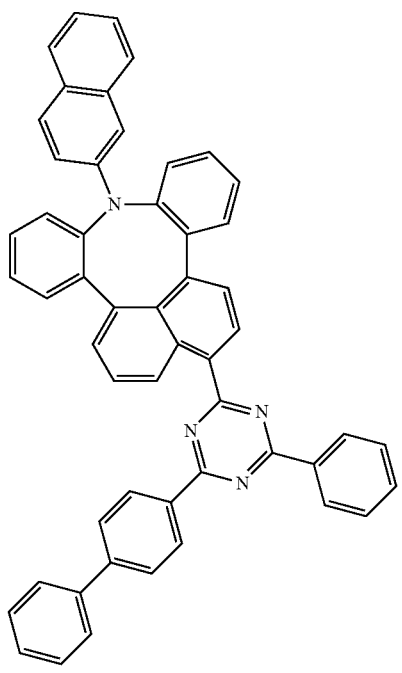
A-94
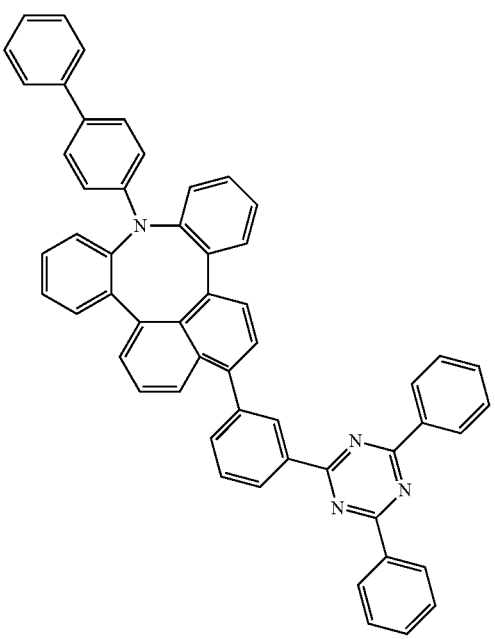

A-95
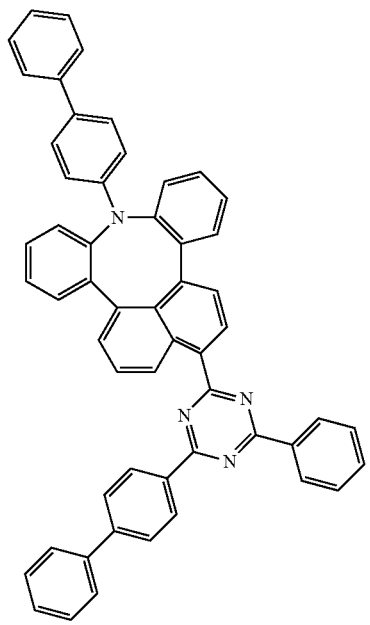
A-96
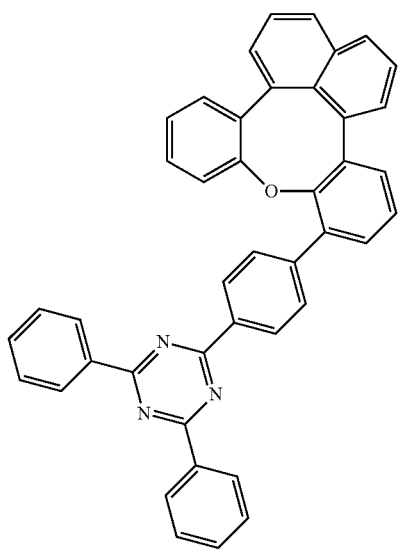
A-97
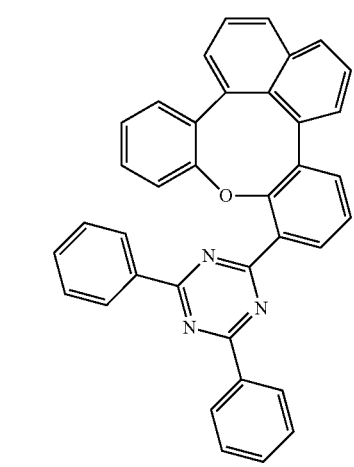
A-98
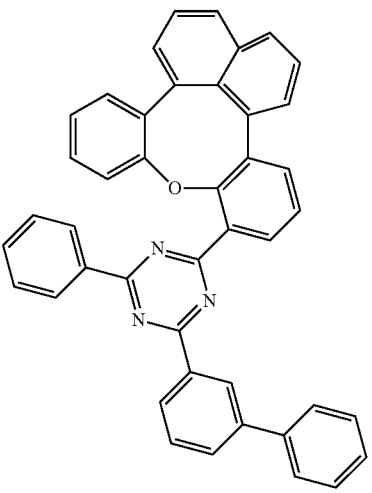
A-99
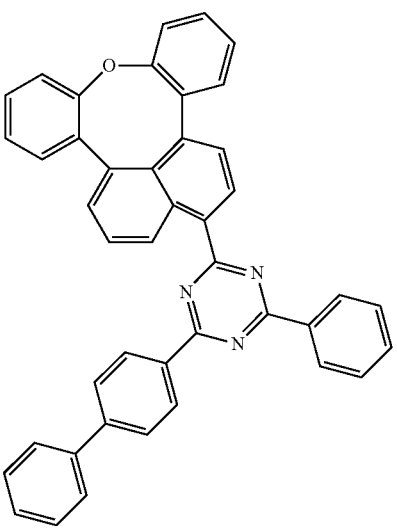
A-100
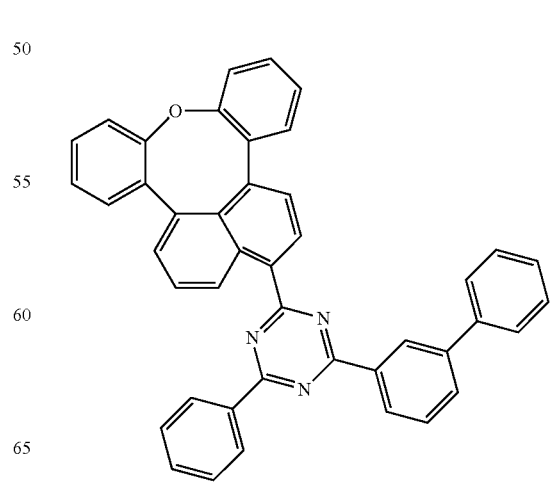

A-101
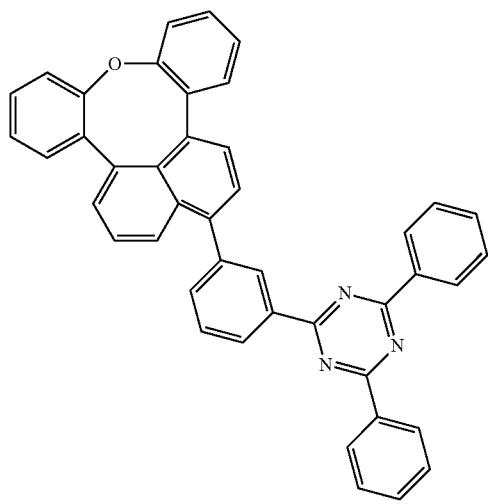
A-102
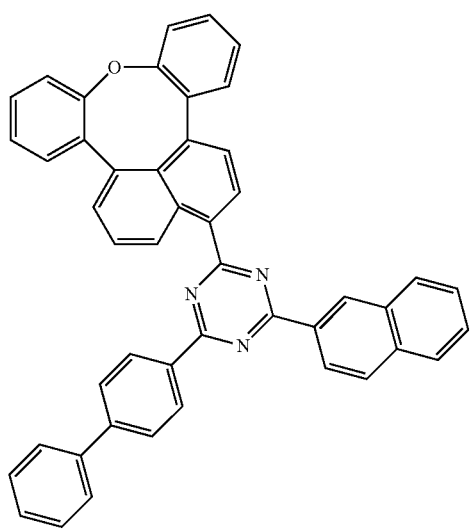
A-103
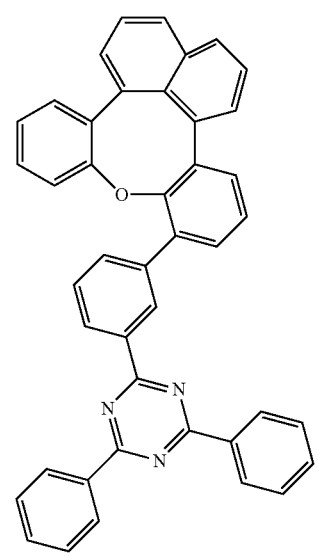
A-104
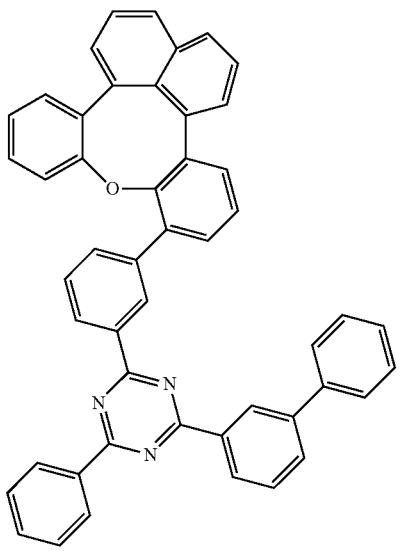
A-105
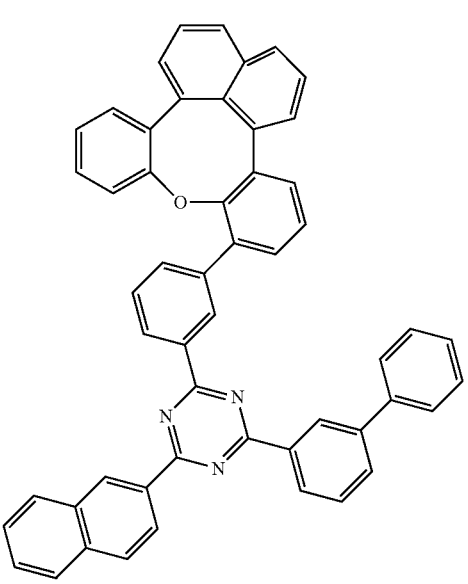
A-106
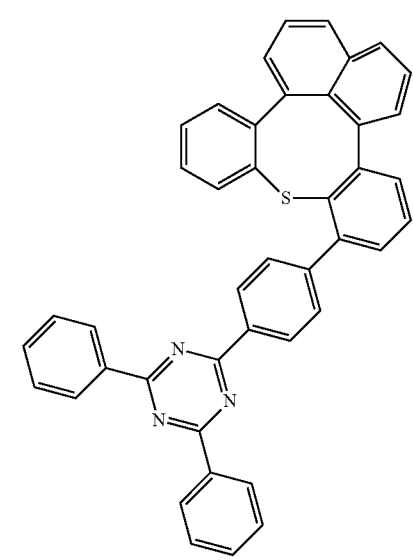

A-107
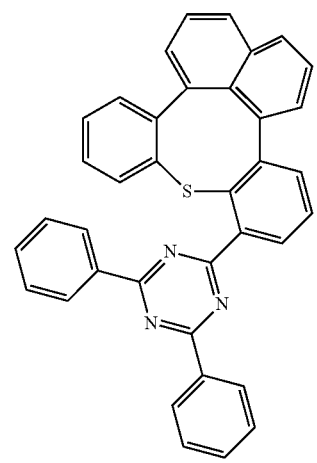
A-110
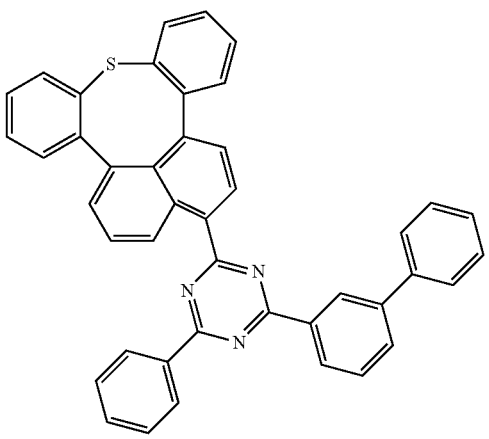
A-108
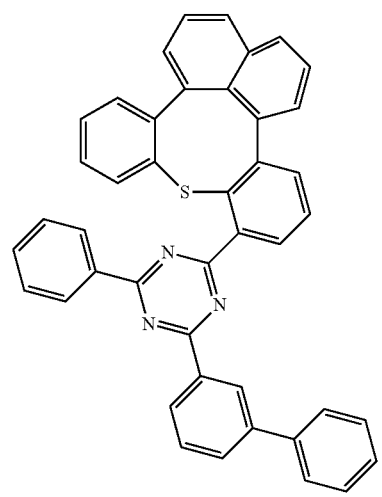
A-111
A-109
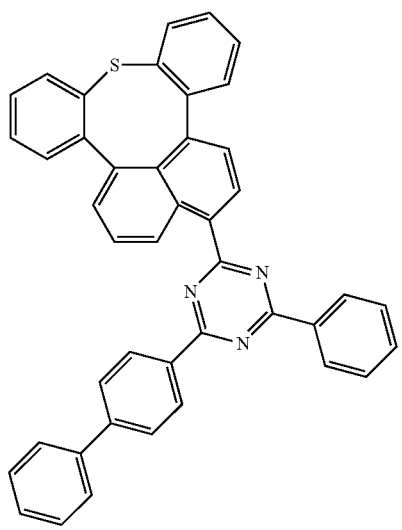
A-112
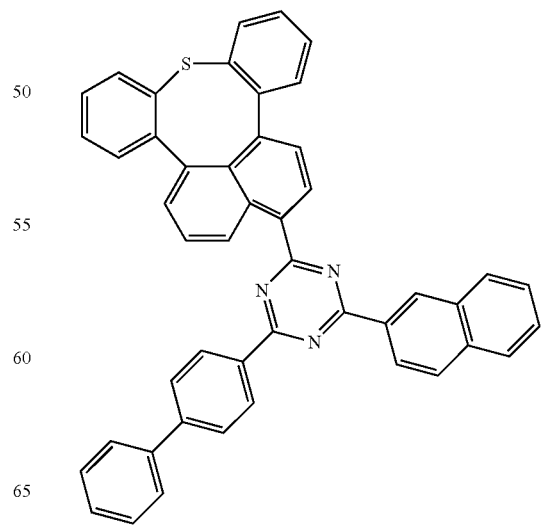

A-113
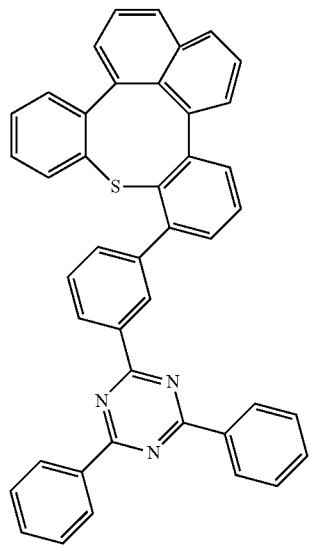
A-114
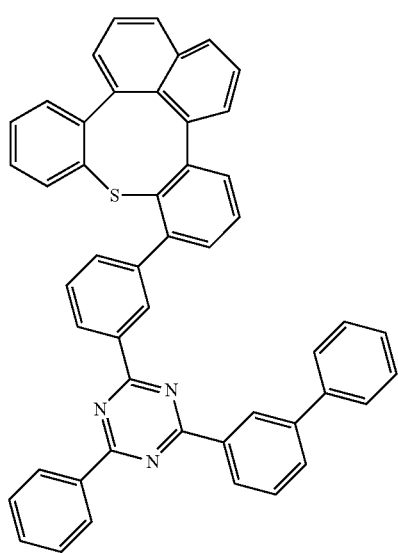
A-115
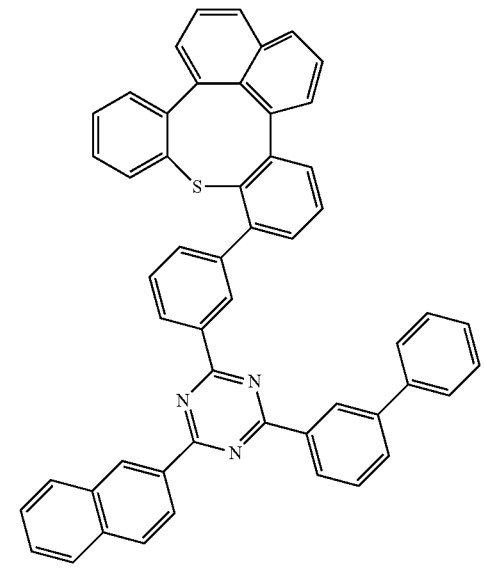
A-116
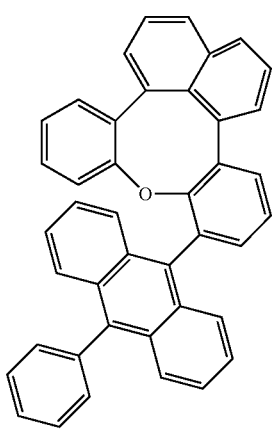
A-117
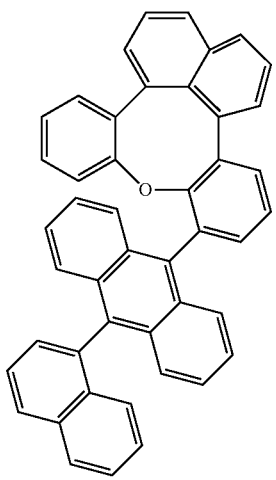

-continued
A-118
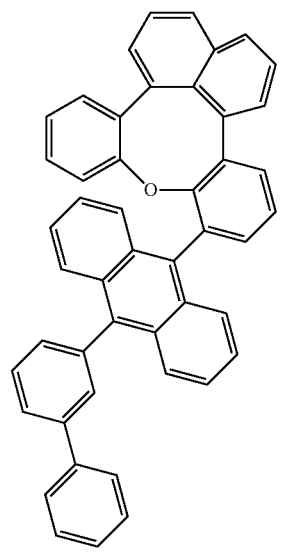
A-119
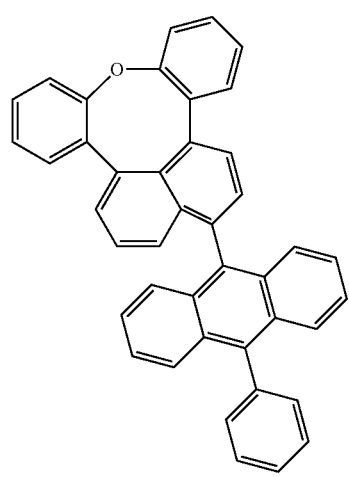
A-120
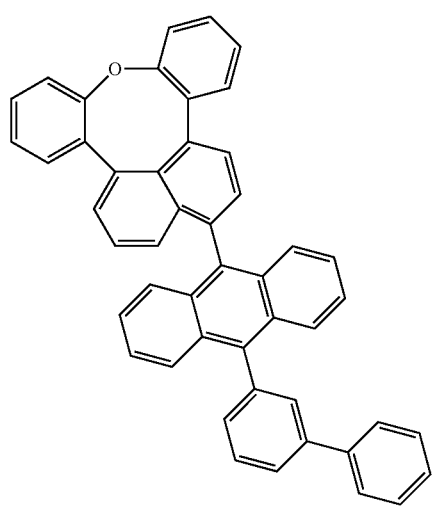
A-121
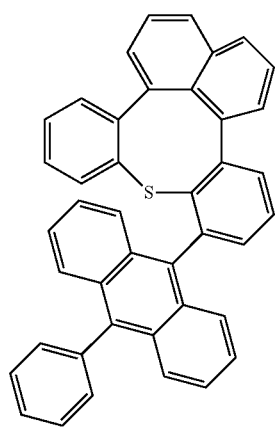
A-122
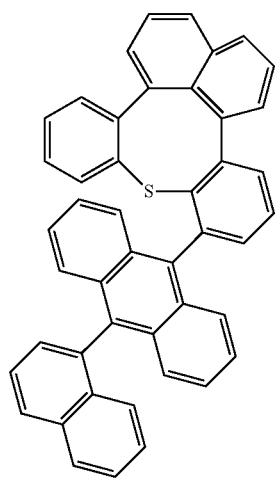
A-123
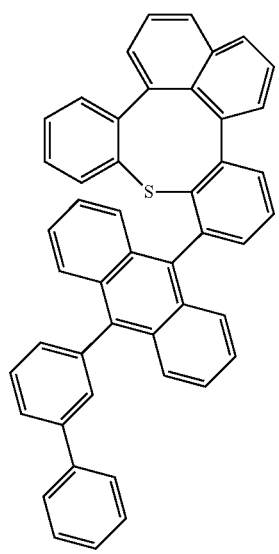

A-124
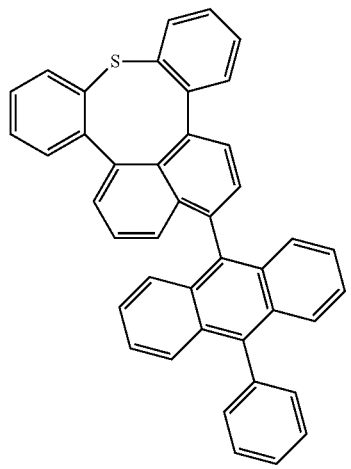
A-125
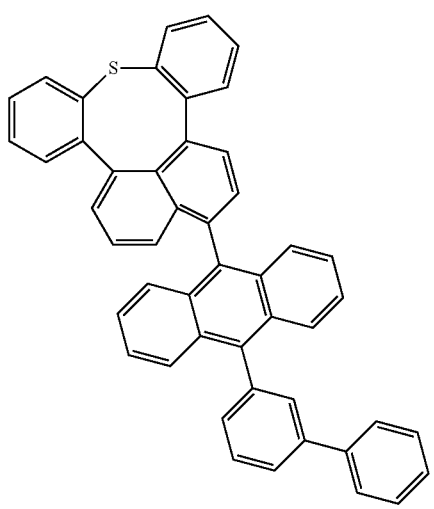
A-126
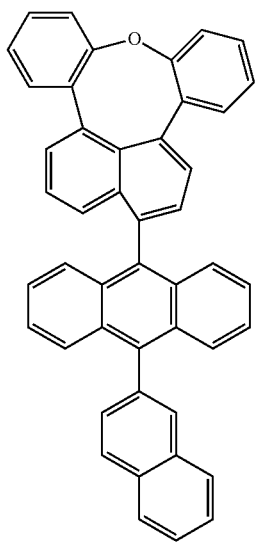
A-127
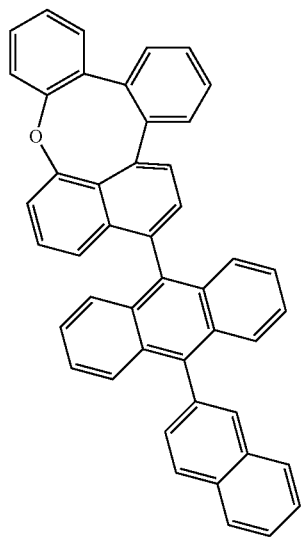
A-128
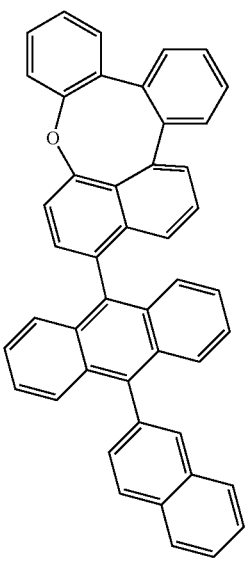
A-129
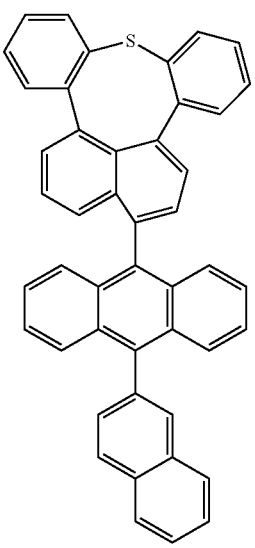

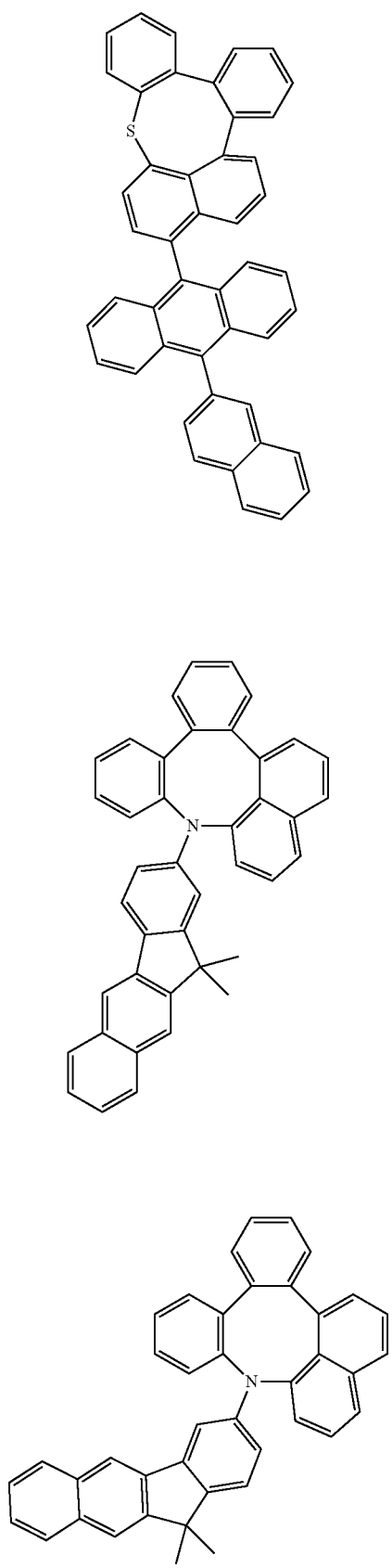

A-130

A-131

A-132

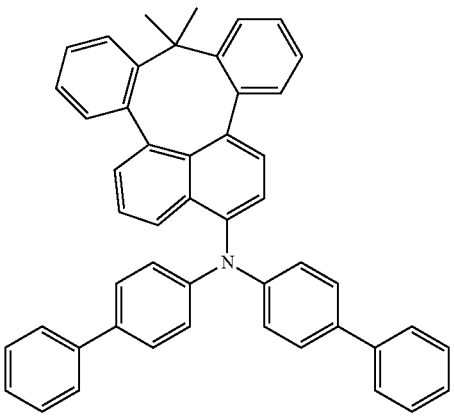

A-133

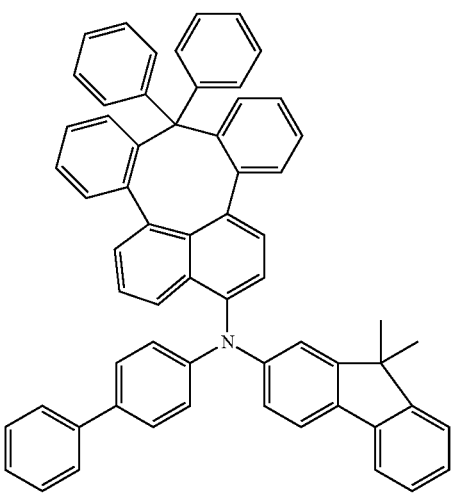

A-134 and

A-135

7. An organic electroluminescent material comprising the organic electroluminescent compound according to claim 1.

8. An organic electroluminescent device comprising the organic electroluminescent compound according to claim 1.

9. The organic electroluminescent device according to claim 8, wherein the organic electroluminescent compound is comprised in a hole transport zone.

* * * * *